United States Patent [19]

Moore

[11] Patent Number: 6,054,289
[45] Date of Patent: Apr. 25, 2000

[54] POLYNUCLEOTIDES ENCODING HUMAN ADA2

[75] Inventor: Paul A. Moore, Aberdeen, United Kingdom

[73] Assignee: Human Genome Sciences, Inc., Rockville, Md.

[21] Appl. No.: 08/705,771

[22] Filed: Aug. 30, 1996

Related U.S. Application Data

[60] Provisional application No. 60/002,993, Aug. 30, 1995.

[51] Int. Cl.[7] ............................ C12N 15/12; C12N 15/10; C12N 5/10; C07K 14/47
[52] U.S. Cl. ....................... 435/69.1; 530/350; 530/300; 536/23.1; 536/23.5; 435/320.1; 435/325; 435/252.3; 435/254.11
[58] Field of Search .................................. 536/23.5, 23.1; 530/350, 300; 435/69.1, 320.1, 325, 252.3, 254.11

[56] References Cited

U.S. PATENT DOCUMENTS 4,851,341  7/1989  Hopp et al. .............................. 435/68

FOREIGN PATENT DOCUMENTS

WO 94/01548  1/1994  WIPO .

OTHER PUBLICATIONS

Genbank Accession No. T91332 (Mar. 22, 1995).
Genbank Accession No. T91418 (Mar. 22, 1995).
Genbank Accession No. T86621 (Mar. 17, 1995).
GenBank Accession Number U13871, pT7T3D cloning vector complete sequence, Dec. 1994.
Ganong et al., Review of Medical Physiology, 17th ed., Appleton & Langeis Norwalk, CT, pp. 220 and 446, 1995.
Watson et al., Molecular Biology of the Gene, 4th Ed., Benjamin/Cummings:Menlo Park, CA, p. 965, 1987.

*Primary Examiner*—Lorraine Spector
*Assistant Examiner*—Claire M. Kaufman
*Attorney, Agent, or Firm*—Michele M. Wales

[57] ABSTRACT

Human polypeptides and DNA (RNA) encoding such polypeptides and a procedure for producing such polypeptides by recombinant techniques is disclosed. Also disclosed are methods for utilizing such polypeptide for therapeutic purposes. Antagonist against such polypeptides and their use as a therapeutic are also disclosed. Also disclosed are diagnostic methods for detecting disease which utilize the sequences and polypeptides.

56 Claims, 15 Drawing Sheets

Amyloid-like protein

```
              10                  30                  50
CACGAGCCACCATGGATGTTTTCAAGAAGGGCTTCTCCATCGCCAAGAAGGGCGTGGTGG
              M  D  V  F  K  K  G  F  S  I  A  K  K  G  V  V  G 70                  90                 110
GTGCGGTGGAAAAGACCAAGCAGGGGGTGACGGAAGCAGCTGAGAAGACCAAGGAGGGGG
    A  V  E  K  T  K  Q  G  V  T  E  A  A  E  K  T  K  E  G  V 130                 150                 170
TCATGTATGTGGGAGCCAAGACCAAGGAGAATGTTGTACAGAGCGTGACCTCAGTGGCCG
    M  Y  V  G  A  K  T  K  E  N  V  V  Q  S  V  T  S  V  A  E 190                 210                 230
AGAAGACCAAGGAGCAGGCCAACGCCGTGAGCAAGGCTGTGGTGAGCAGCGTCAACACTG
    K  T  K  E  Q  A  N  A  V  S  K  A  V  V  S  S  V  N  T  V 250                 270                 290
TGGCCACCAAGACCGTGGAGGAGGCGGAGAACATCGCGGTCACCTCCGGGGTGGTGCGCA
    A  T  K  T  V  E  E  A  E  N  I  A  V  T  S  G  V  V  R  K 310                 330                 350
AGGAGGACTTGAGGCCATCTGCCCCCCAACAGGAGGGTGAGGCATCCAAAGAGAAAGAGG
    E  D  L  R  P  S  A  P  Q  Q  E  G  E  A  S  K  E  K  E  E 370                 390                 410
AAGTGGCAGAGGAGGCCCAGAGTGGGGGAGACTAGAGGGCTACAGGCCAGCGTGGATGAC
    V  A  E  E  A  Q  S  G  G  D  *

430                 450                 470
CTGAAGAGCGCTCCTCTGCCTTGGACACCATCCCCTCCTAGCACAAGGAGTGCCCGCCTT 490                 510                 530
GAGTGACATGCGGGTGCCCACGCTCCTGCCCTCGTCTCCCTGGACACCCTTGGCCTGTCC

550
ACCTGTGCTG
```

FIG.1 hADA2

AATTCCTGGGGGGTCTCGGCGAGGGAGTCATCAAGCTTTGGTGTATGTgTTGGCCCGTTC
TGAAGTCTTGAAGAAGCTCTGcTGAGGAAGACCAAAGCAGCACTCGTTGCCAATTAGGGA

```
  M   D   R   L   G   S   F   S   N   D   P   S   D   K   P   P   C   R   G   C
ATGGACCGTTTGGGTTCCTTTAGCAATGATCCCTCTGATAAGCCACCTTGCCGAGGCTGC
```

```
  S   S   Y   L   M   E   P   Y   I   K   C   A   E   C   G   P   P   P   F   F
TcCTCCTACCTCATGGAGCCTTATATCAAGTGTGCTGAATGTGGGCCACCTCCTTTTTTC
```

```
  L   C   L   Q   C   F   T   R   G   F   E   Y   K   K   H   Q   S   D   H   T
CTCTGCTTGCAGTGTTTCACTCGAGGCTTTGAGTACAAGAAACATCAAAGCGATCATACT
```

```
  Y   E   I   M   T   S   D   F   P   V   L   D   P   S   W   T   A   Q   E   E
TATGAAATAATGACTTCAGATTTTCCTGTCCTTgATCCCAGCTGGACTGCTCAAGAAGAa
```

```
  M   A   L   L   E   A   V   M   D   C   G   F   G   N   W   Q   D   V   A   N
ATGGCCCTTTtAGAAGCTGTGATGGACTGTGGCTTTGGAAATTGGCAGGATGTAGCCAAT
```

```
  Q   M   C   T   K   T   K   E   E   C   E   K   H   Y   M   K   H   F   I   N
CAAATGTGCACCAAGACCAAGGAGGAGTGTGAGAAGCACTATATGAAGCATTTCATCAAT
```

```
  N   P   L   F   A   S   T   L   L   N   L   K   Q   A   E   E   A   K   T   A
AACCCTCTGTTTGCATCTACCCTGCTGAACCTGAAACAAGCAGAGGAAGCAAAAACTGCT
```

```
  D   T   A   I   P   F   H   S   T   D   D   P   P   R   P   T   F   D   S   L
GACACAGCCATTCCATTTCACTCTACAGATGACCCTCCCCGACCTACCTTTGACTCCTTG
```

```
  L   S   R   D   M   A   G   Y   M   P   A   R   A   D   F   I   E   E   F   D
CTTTCTCGGGACATGGCCGGGTACATGCCAGCTCGAGCAGATTTCATTGAGGAATTTGAC
```

```
  N   Y   A   E   W   D   L   R   D   I   D   F   V   E   D   D   S   D   I   L
AATTATGCAGAATGGGACTTGAGAGACATTGATTTTGTTGAAGATGACTCGGACATTTTA
```

FIG. 2A

```
H  A  L  K  M  A  V  V  D  I  Y  H  S  R  L  K  E  R  Q  R
CATGCTCTGAAGATGGCTGTGGTAGATATCTATCATTCCAGGTTAAAGGAGAGACAAAGA

R  K  K  I  I  R  D  H  G  L  I  N  L  R  K  F  Q  L  M  E
CGAAAAAAAATTATAAGAGACCATGGATTAATCAACCTTAGAAAGTTTCAATTAATGGAA

R  R  Y  P  K  E  V  Q  D  L  Y  E  T  M  R  R  F  A  R  I
CGGCGGTATCCCAAGGAGGTCCAGGACCTGTATGAAACAATGAGGCGATTTGCAAGAATT

V  G  P  V  E  H  D  K  F  I  E  S  H  A  L  E  F  E  L  R
GTGGGGCCAGTGGAACATGACAAATTCATTGAAAGCCATGCATTGGAATTTGAACTCCGA

R  E  I  K  R  L  Q  E  Y  R  T  A  G  I  T  N  F  C  S  A
AGGGAAATCAAGAGGCTCCAAGAATACAGGACAGCAGGCATTACCAATTTTTGTAGTGCC

R  T  Y  D  H  L  K  K  T  R  E  E  E  R  L  K  R  T  M  L
AGAACCTACGATCACCTCAAGAAGACACGGGAGGAAGAGCCGCCTTAAACGCACTATGCTC

S  E  V  L  Q  Y  I  Q  D  S  S  A  C  Q  Q  W  L  R  R  Q
TCAGAAGTTCTCCAGTATATCCAGGACAGTAGTGCTTGCCAGCAGTGGCTCCGCCGGCAA

A  D  I  D  S  G  L  S  P  S  I  P  M  A  S  N  S  G  R  R
GCTGACATTGATTCCGGCCTGAGTCCTTCCATTCCAATGGCTTCGAATTCAGGTAGACGG

S  A  P  P  L  N  L  T  G  L  P  G  T  E  K  L  N  E  K  E
AGTGCACCACCCTTGAACCTCACTGGCCTCCCTGGCACAGAGAAGCTGAATGAAAAAGAA

K  E  L  C  Q  M  V  R  L  V  P  G  A  Y  L  E  Y  K  S  A
AAGGAGCTCTGTCAGATGGTGAGGTTGGTCCCTGGAGCCTATTTAGAATACAAATCTGCT

L  L  N  E  C  N  K  Q  G  G  L  R  L  A  Q  A  R  A  L  I
CTATTGAACGAATGTAACAAGCAAGGAGGCTTAAGACTGGCGCAGGCAAGAGCACTCATC

K  I  D  V  N  K  T  R  K  I  Y  D  F  L  I  R  E  G  Y  I
AAGATAGATGTGAACAAAACCCGGAAAATCTATGATTTCCTCATCAGAGAAGGATACATC

T  K  G  *
ACTAAAGGCTAAGGCTCCAAGAGCTTGGGATCAGAAGTCAGAAGTTTGGAATGTGGTGGG
TCAAAGGACAATATGGGTGGGCATTCTGGAGAGTTtGTTTTTCAGCTGAATTCTCATGGT
GAAAACAGGGGAAAGGACAAAGGAAACCTTAAGTTGTATTGTCTACTTTCTTCTCCATCC
TGCTTTAAAACACTCCTGTTGTTGGTATTATGCTGCAGAGTTGTGTGCTACATAAGCTAT
TATTAAATGTGAGTGGGCATTCAAAAAAAAAAAAAAAAAAAA
```

FIG. 2B

TATA Related Factor (TRF)

```
                    GGCACGAGGCGCCCCCGGGGTCCCCCGGCCCCTGCAGGGCTACTTGGGCGCAGAG   60
CCGCGGAGGGTCTCCGTTCCTAGAGGTCCTCCTATCCCGGGCTGCCTGAGTCCTCGCCAG
CATCCGCCCTCTCCCACTCCCATCCTTCCTGGATCCGCCTCTCGGTTCCCGAGGGACAGT  180
CCCGACCGCAAACCCACGTAGAGTAAGGAATGTGGGACAGGCGACAGAAGTGGCATACGG
TCCTGCGTTATCCCTCCGTCTCGCCACACCTTGTGTCTCCATCTCTCCCCACTTCCTTCC  300
CTCCGTCTGTCATCTGTCATCCCCGGTCGCTCTAAGACCAGGATTCCAATTCGCCTAGTG
AGGAATCTCACTAGGGGAATTTATCGCGACATCATAAATTAACGGGTTCATTTTGACTGA  420
AAAAGCGAAGGACTTTTTTCAGGCAGAAAACAAGTCTCGTCTGGACGGATGTGATCTTCG

M  D  A  D  S  D  V  A  L  D
TGGTGGAAAAGCTAAATTTTAAAACCACCCCAATGGATGCAGACAGTGATGTTGCATTGGA   540

I  L  I  T  N  V  V  C  V  F  R  T  R  C  H  L  N  L  R  K
CATTCTAATTACAAATGTAGTCTGTGTTTTTAGAACAAGATGTCATTTAAACTTAAGGAA   600

I  A  L  E  G  A  N  V  I  Y  K  R  D  V  G  K  V  L  M  K
GATTGCTTTGGAAGGAGCAAATGTAATTTATAAACGTGATGTTGGAAAAGTATTAATGAA   660

L  R  K  P  R  I  T  A  T  I  W  S  S  G  K  I  I  C  T  G
GCTTAGAAAACCTAGAATTACAGCTACAATTTGGTCCTCAGGAAAAATTATTTGCACTGG   720

A  T  S  E  E  E  A  K  F  G  A  R  R  L  A  R  S  L  Q  K
AGCAACAAGTGAAGAAGAAGCTAAATTTGGTGCCAGACGCTTAGCCCGTAGTCTGCAGAA   780

L  G  F  Q  V  I  F  T  D  F  K  V  V  N  V  L  A  V  C  N
ACTAGGTTTTCAGGTAATATTTACAGATTTTAAGGTTGTTAACGTTCTGGCAGTGTGTAA   840

M  P  F  E  I  R  L  P  E  F  T  K  N  N  R  P  H  A  S  Y
CATGCCATTTGAAATCCGTTTGCCAGAATTCACAAAGAACAATAGACCTCATGCCAGTTA   900

E  P  E  L  H  P  A  V  C  Y  R  I  K  S  L  R  A  T  L  Q
CGAACCTGAACTTCATCCTGCTGTGTGCTATCGGATAAAATCTCTAAGAGCTACATTACA   960

I  F  S  T  G  S  I  T  V  T  G  P  N  V  K  A  V  A  T  A
GATTTTTTCAACAGGAAGTATCACAGTAACAGGGCCCAATGTAAAGGCTGTTGCTACTGC  1020

V  E  Q  I  Y  P  F  V  F  E  S  R  K  E  I  L  *
TGTGGAACAGATTTACCCATTTGTGTTTGAAAGCAGGAAAGAAATTTTATAATTCACCAC  1080
```

FIG. 3A

```
TTAATTGGTTAGAATCTCTAACTGAGCACCTTTTAAACCTGCTGCACATTGGACTCAAAA
GGAAAACTGGACCAACAATAATTGAGGAAATAGACTCTTTTATTCATTCACGGCTACAGT     1200
GTAAGCTCCAGTCCCTTTGGATTTTATTCCAAACCTTGCTGTAATATAAAAGGAAGTTTA
CAAGACATGATATTGCTGCTTTTACAAAAGGACATTCTATTTATTTTCGCAGTAATTCTC    1320
ATGTCCCCATAAGCAGAGCTGTCACAGTGTGCACTACCTTAGATTGTTTTATTGTCGTCA
TTGTTATTTTTTTCCATTTTGAGCTAATGTGTTTTATTTGTGAATAGTCTTTTACATTTT    1440
GGTATGCTGAATATGGGCACCAAAGAACCTGTAAAAGTTATCTTTTTCAATTGAATGTGC
ACAAATAAAAGTTTGGAAAGAAAAAAAAAAAAAAAAAAAAAAA                     1543
```

FIG. 3B hRPB11

```
              M   N   A   P   P   A   F   E   S   F   L   L   F
  1   ACGAGCAACGGCGGCGGGAGCATGAACGCCCCTCCAGCCTTCgAGTCGTTCTTGCTCTTC

E   G   E   K   K   I   T   I   N   K   D   T   K   V   P   N   A   C   L   F
 61   GAGGGCGAGAAGAagaTCACCATTAACAAGGACACCAAGGTACCCAATGCCTGTTTATTC T   I   N   K   E   D   H   T   L   G   N   I   I   K   S   Q   L   L   K   D
121   ACCATCAACAAAGAAGACCACACACTGGGAAACATCATTAAATCACAACTCCTAAAAGAC P   Q   V   L   F   A   G   Y   K   V   P   H   P   L   E   H   K   I   I   I
181   CCGCAAGTGCTATTTGCTGGcTACAAAGTCCCCCACCCCTTGGAGCACAAGATCATCATC R   V   Q   T   T   P   D   Y   S   P   Q   E   A   F   T   N   A   I   T   D
241   CGAGTGCAGACCACGcCGGACTACaGCCCCCAGGAAGCCTTTACCAACGCCATCACCGAC L   I   S   E   L   S   L   L   E   E   R   F   R   V   A   I   K   D   K   Q
301   CTCATCAGTGAGCTGTCCCTGCTGGAGGAGCGCTTTCGGGTGGCCATAAAAGACAAGCAG E   G   I   E   *
361   GAAGGAATTGAGTAGGGGCCAGAGGGGGCTCTGCTCGGCCTGTGAGCCCcGTTCCTACCT GTGCCTGACCCTCCGcTCCAGGTACCACACCGAGGAGAGCGGgCaGTCCCAGCCATGGCC
      CGCCTTGTGGcCACCCCTCAcCCTGACAcCGACGTGTCCTGTACATAGATTAGGTTTTAT
      ATTCCTAATAAAGTA  555
```

FIG.4

IRF3

```
                                                  M  G  T  P  K
GGTTCCAGCTGCCCGcACGCCCCGACCTTCCATCGTAGGCCCGGACCATGGGAACCCCAAA

P  R  X  L  P  W  L  V  S  Q  L  D  L  G  Q  L  E  G  V  A
GCCACGGnTCCTGCCCTGGCTGGTGTCGCAGCTGGACCTGGGGCAACTGGAGGGCGTGGC

W  V  N  K  S  R  T  R  F  R  I  P  W  K  H  G  L  R  Q  D
CTGGGTGAACAAGAGCCGCACGCGCTTCCGCATCCCTTGGAAGCACGGCCTACGGCAGGA

A  Q  Q  E  D  F  G  I  F  Q  A  W  A  E  A  T  G  A  Y  V
TGCACAGCAGGAGGATTTCGGAATCTTCCAGGCCTGGGCCGAGgCCACTGGTGCATATGT

P  G  R  D  K  P  D  L  P  T  W  K  R  N  F  R  S  A  L  N
TCCCGGGAGGGATAAGCCAGACCTGCCAACCTGGAAGAGGAATTTCCGCTCTGCCCTCAA

R  K  E  G  L  R  L  A  E  D  R  S  K  D  P  H  D  P  H  K
CCGCAAAGAAGGGTTGCGTTTAGCAGAGGACCGGAGCAAGGACCCTCACGACCCACATAA

I  Y  E  F  V  N  S  G  V  G  D  F  S  Q  P  D  T  S  P  D
AATCTACGAGTTTGTGAACTCAGGAGTTGGGGACTTTTCCCAGCCAGACACCTCTCCGGA

T  N  G  G  G  S  T  S  D  T  Q  E  D  I  L  D  E  L  L  G
CACCAATGGTGGAGGCAGTACTTCTGATACCCAGGAAGACATTCTGGATGAGTTACTGGG

N  M  V  L  A  P  L  P  D  P  G  P  P  S  L  A  V  A  P  E
TAACATGGTGTTGGCCCCACTCCCAGATCCGGGACCCCCAAGCCTGGCTGTAGCCCCTGA

P  C  P  Q  P  L  R  S  P  S  L  D  N  P  T  P  F  P  N  L
GCCCTGCCCTCAGCCCCTGCGGAGCCCCAGCTTGGACAATCCCACTCCCTTCCCAAACCT

G  P  S  E  N  P  L  K  R  L  L  V  P  G  E  E  W  E  F  E
GGGGCCCTCTGAGAACCCACTGAAGCGGCTGTTGGTGCCGGGGGAAGAGTGGGAGTTCGA

V  T  A  F  Y  R  G  R  Q  V  F  Q  Q  T  I  S  C  P  E  G
GGTGACAGCCTTCTACCGGGGCCGCCAAGTCTTCCAGCAGACCATCTCCTGCCCGGAGGG
```

FIG. 5A

```
  L   R   L   V   G   S   E   V   G   D   R   T   L   P   G   W   P   V   T   L
CCTGCCGGCTGGTGGGGTCCGAAGTGGGAGACAGGACGCTGCCTGGATGGCCAGTCACACT

P   D   P   G   M   S   L   T   D   R   G   V   M   S   Y   V   R   H   V   L
GCCAGACCCTGGCATGTCCCTGACAGACAGGGGAGTGATGAGCTACGTGAGGCATGTGCT

S   C   L   G   G   G   L   A   L   W   R   A   G   Q   W   L   W   A   Q   R
GAGCTGCCTGGGTGGGGGACTGGCTCTCTGGCGGGCCGGGCAGTGGCTCTGGGCCCAGCG

L   G   H   C   H   T   Y   W   A   V   S   E   E   L   L   P   N   S   G   H
GCTGGGGCACTGCCACACATACTGGGCAGTGAGCGAGGAGCTGCTCCCCAACAGCGGGCA

G   P   D   G   E   V   P   K   D   K   E   G   G   V   F   D   L   G   P   F
TGGGCCTGATGGCGAGGTCCCCAAGGACAAGGAAGGAGGCGTGTTTGACCTGGGGCCCTT

I   V   D   L   I   T   F   T   E   G   S   G   R   S   P   R   Y   A   L   W
CATTGTAGATCTGATTACCTTCACGGAAGGAAGCGGACGCTCACCACGCTATGCCCTCTG

F   C   V   G   E   S   W   P   Q   D   Q   P   W   T   K   R   L   V   M   V
GTTCTGTGTGGGGGAGTCATGgCCCCAGGACCAGCCGTGGACCAAGAGGCTCGTGATGGT

K   V   V   P   T   C   L   R   A   L   V   E   M   A   R   V   G   G   A   S
CAAGGTTGTGCCCACGTGCCTCAGGGCCTTGGTAGAAATGGCCCGGGTAGGGGGTGCCTC

S   L   E   N   T   V   D   L   H   I   S   N   S   H   P   L   S   L   T   S
CTCCCTGGAGAATACTGTGGACCTGCACATTTCCAACAGCCACCCACTCTCCCTCACCTC

D   Q   Y   K   A   Y   L   Q   D   L   V   E   G   M   D   F   Q   G   P   G
CGACCAGTACAAGGCCTACCTGCAGGACTTGGTGGAGGGCATGGATTTCCAGGGCCCTGG

E   S   *
GGAGAGCTGAGCCCTCGCTCCTCATGGTGTGCCTCCAACCCCCCTGTTCCCCACCACCTC
AACCAATAAACTGGTTCCTGCTATGAAAAAAAAAAAAAAAAAAAAAA
```

Full length sequence:

AATTCGGCAGAGGCAGTTCCTAGCCGAGGAGGCGCCCGCGCATTGCCGCTCTCTCGGTGAGCGCAGCCCGCTCTCCGGGCCGGGCCT
TCGCGGGCCACCGCGCCATGGGCCAGTGCGGCATCACCTCCTCCAAGACCGTGCTGGTCTTTCTCAACCTCATCTTCTGGGGGGC
AGCTGGCATTTTATGCTATGTGGGAGCCTATGTCTTCATCACTTATGATGACTATGACCACTTCTTTGAAGATGTGTACACGCTC
ATCCCTGCTGTAGTGATCATAGCTGTAGGAGCCCTGCTTTTCATCATTGGGCTAATTGGCTGCTGTGCCACAATCCGGGAAAGTC
GCTGTGGACTTGCCACGTTTGTCATCATCCTGCTCTTGGTTTTTGTCACAGAAGTTGTTGTAGTGGTTTTGGGATATGTTTACAG
AGCAAAGGTGGAAAATGAGGTTGATCGCAGCATTCAGAAAGTGTATAAGACCTACAATGGAACCAACCCTGATGCTGCTAGCCGG
GCTATTGATTATGTACAGAGACAGCTGCATTGTTGTGGAATTCACAACTACTCAGACTGGGAAAATACAGATTGGTTCAAAGAAA
CCAAAAACCAGAGTGTCCCTCTTAGCTGCTGCAGAGAGACTGCCAGCAATTGTAATGGCAGCTGGCCACCCTTCCGACTCTATGC
TGAGGGGTGTGAGGCTCTAGTTGTGAAGAAGCTACAAGAAATCATGATGCATGTGATCTGGGCCGCACTGGCATTTGCAGCTATT
CAGCTGCTGGGCATGCTGTGTGCTTGCATCGTGTTGTGCAGAAGGAGTAGAGATCCTGCTTACGAGCTCCTCATCACTGGCGGAA
CCTATGCATAGTTGACAACTCAAGCCTGAGCTTTTTGGTCTTGTTCTGATTTGGAAGGTGAATTGAGCAGGTCTGCTGCTGTTGG
CCTCTGGAGTTCATCTAGTTAAAGCACATGTACACTGGTGTTGGACAGAGCAGCTTGGCTTTTCAT coding sequence:
ATGGGCCAGTGCGGCATCACCTCCTCCAAGACCGTGCTGGTCTTTCTCAACCTCATCTTCTGGGGGGCAGCTGGCATTTTATGCT
ATGTGGGAGCCTATGTCTTCATCACTTATGATGACTATGACCACTTCTTTGAAGATGTGTACACGCTCATCCCTGCTGTAGTGAT
CATAGCTGTAGGAGCCCTGCTTTTCATCATTGGGCTAATTGGCTGCTGTGCCACAATCCGGGAAAGTCGCTGTGGACTTGCCACG
TTTGTCATCATCCTGCTCTTGGTTTTTGTCACAGAAGTTGTTGTAGTGGTTTTGGGATATGTTTACAGAGCAAAGGTGGAAAATG
AGGTTGATCGCAGCATTCAGAAAGTGTATAAGACCTACAATGGAACCAACCCTGATGCTGCTAGCCGGGCTATTGATTATGTACA
GAGACAGCTGCATTGTTGTGGAATTCACAACTACTCAGACTGGGAAAATACAGATTGGTTCAAAGAAACCAAAAACCAGAGTGTC
CCTCTTAGCTGCTGCAGAGAGACTGCCAGCAATTGTAATGGCAGCTGGCCACCCTTCCGACTCTATGCTGAGGGGTGTGAGGCTC
TAGTTGTGAAGAAGCTACAAGAAATCATGATGCATGTGATCTGGGCCGCACTGGCATTTGCAGCTATTCAGCTGCTGGGCATGCT
GTGTGCTTGCATCGTGTTGTGCAGAAGGAGTAGAGATCCTGCTTACGAGCTCCTCATCACTGGCGGAACCTATGCATAG The translation product from above sequence is as follows:
MGQCGITSSKTVLVFLNLIFWGAAGILCYVGAYVFITYDDYDHFFEDVYTLIPAVVIIAVGALLFIIGLIGCCATIRESRCGLAT
FVIILLLVFVTEVVVVVLGYVYRAKVENEVDRSIQKVYKTYNGTNPDAASRAIDYVQRQLHCCGIHNYSDWENTDWFKETKNQSV
PLSCCRETASNCNGSWPPFRLYAEGCEALVVKKLQEIMMHVIWAALAFAAIQLLGMLCACIVLCRRSRDPAYELLITGGTYA.

FIG.6

TNFR AF1, C1

Full length sequence:
GAGCCAGGACTCCACAAGGCTGGTCCCCTGCCCTGGAGCAACTTAAACAGGCCCTCTGGCCAGCCTGGAACCCTGAGATGGCCTC
CAGCTCAGGCAGCAGTCCTCGCCCGGCCCCTGATGAGAATGAGTTTCCCTTTGGGTGCCCTCCCACCGTCTGCCAGGACCCAAAG
GAGCCCAGGGCTCTCTGCTGTGCAGGCTGTCTCTCTGAGAACCCGAGGAATGGCGAGGATCAGATCTGCCCCAAATGCAGAGGGG
AAGACCTCCAGTCTATAAGCCCAGGAAGCCGTCTTCCAACTCAGGAGAAGGTTCAGGCGGAGGTCGCTGAGGCTGGGATTGGGTG
CCCCTTTGCTGTTGTCGGCTGCTCCTTCAAGGGAAGCCCACAGTTTGTGGAAGAGCATGAGGTCACCTCCCAGACCTCCCACCTA
AACCTGCTGTTGGGGTTCATGAAACAGTGGAAGGCCCGGCTGGGCTGTGGCCTGGATTCTGGGCCCATGGCCCTGGAGCAGAACC
TGTCAGACCTGCAGCTGCAGGCAGCCGTGGAAGTGGCGGGGGACCTGGAGGTCGATTGCTACCGGGCACCCTGCTCCGAGAGCCA
GGAGGAGCTGGCCCTGCAGCACTTCATGAAGGAGAAGCTTCTGGCTGAGCTGGAGGGGAAGCTGCCGTGTGTTTGAGAACAATGTT
GCTGTCCTCAACAAGGAGGTGGAGGCCTCCCACCTGGCCCTGGCCACCTCTATCCACCAGAGCCAGCTGGACCGTGAGCGCATCC
TGAGCTTGGAGCAGAGGGTGGTGCAGGTTCAGCAGACCCTGGCCCAGAAAGACCAGGCCCTGGGCAAGCTGGAGCAGAGCTTGCG
CCTCATGGAGGAGGCCTCCTTCGATGGCACTTTCCTGTGGAAGATCACCAGTGTCACCAGGCGGTGCCATGAGTCGGCCTGTGGC
AGGACCGTCAGCCTCTTCTCCCCAGCCTTCTACACTGCCAAGTATGGCTACAAGTTGTGCCTGCGGCTGTACCTGATTGGAGATG
GCACTGGAAAGAGAACCCATCTTTCGCTCTTCATCGTGATCATGAGAGGGGAGTATGATGCGCTGCTGCCCGTGGCCTTTCCGGAA
CAAGGTCACCTTCATGCTGCTGGACCAGAACAACCGTGAGCACGCCATTGACGCCTTCCGGCCTGACCTAAGCTCAGCGTCCTTC
CAGAGGCCCCAGAGTGAAACCAACGTGGCCAGTGGATGCCCACTCTTCTTCCCCCTCAGCAAACTGCAGTCACCCAAGCACGCCT
ACGTWAAGGACGACACAATGTTCCTCAAGTGCATTGTGGAGACCAGCACTTAGGGTGGGCGGGGCTCCTGAGGGAGTTCCAACTC
AGAAGGGAGCTAGCCAGAGGACTGTGATGCCCTGCCCTTGGCACCCAAGAACTCAGGGCACAAAGATGGGTGAAGGCTGGCATGA
TCCAAGCAAGAYTGAGGGGTCGAYTTCGGGYTGGCCATCTGGTTARGATGGCAGGACGTGGGYTGGGCCCACAAAGGCAAAGGGT
CCAGAAGGAGACAGGCAGAGCTGCTCCCCTCTGCACGGACCATGCGACACTGGGAGGCCAGTGAGCCACTCCGGCCCCGAATGTT
GAGGTGGACTCTCACCAAATGAGAAGAAAATGGAACCAGGCTTGGAACCGTAGGACCCAAGCAGAGAAGCTCTCGGGCTAGGAAG
ATCTCTGCAGGGCCGCCAGGGAGACCTGGACACAGGCCTGCTCTCTTTTTCTCCAGGGTCAGAAACAGGACCGGGTGGAAGGGAT
GGGGTGCCAGTTTGAATGCAGTCTGTCCAGGCTCGTCATTGGAGGTGAACAAGCAAACCCAGACGGCTCCACTAGGACTTCAAAT
TGGGGGTTGGATTTGAAGACTTTTAAGTTTCCTTCCAGCCCAGAAAGTCTCTCATTCTAGCCTCCTGGCCCAGGTGAGTCCTAGA
GCTACAGGGGTTCTGGAAACATTCAGGAGCTTCCTGTCCTCCCAGCTCCTCACTCACCTTCAGTAACCCCCACTGGACTGACCTG
GTCCACAGGGCACCTGCCACCCTGGGCCTGGCAGCTCAGCTTCCCAACACGCAGGAGCACACCCAGCCCCCACATCCTGTGCCTC
CATCAGCTAAACACCACGTCACTTCATGCAGGTGAAACCCAGTCACTGTGAGCTCCCAGGTGCAGCCAGAGGCACCTCAAGAAGA
AGAGGGGCATAAACTTTCCTCTTCCTGCCTAGAGGCCCCACCTTTGGTGCTTTCCAGAATCCCGTAACACCTGATTAACTGAGGC
ATCCACTTCTTTCAGCAGACTGATCAGGACCTCCAAGCCACTGAGCAATGTATAACCCCAAAGGGAATTCAA

FIG. 7A

Coding sequence:
ATGGCCTCCAGCTCAGGCAGCAGTCCTCGCCCGGCCCCTGATGAGAATGAGTTTCCCTTTGGGTGCCCTCCCACCGTCTGCCAGG
ACCCAAAGGAGCCCAGGGCTCTCTGCTGTGCAGGCTGTCTCTCTGAGAACCCGAGGAATGGCGAGGATCAGATCTGCCCCAAATG
CAGAGGGGAAGACCTCCAGTCTATAAGCCCAGGAAGCCGTCTTCGAACTCAGGAGAAGGTTCAGGCGGAGGTCGCTGAGGCTGGG
ATTGGGTGCCCCTTTGCTGTTGTCGGCTGCTCCTTCAAGGGAAGCCCACAGTTTGTGGAAGAGCATGAGGTCACCTCCCAGACCT
CCCACCTAAACCTGCTGTTGGGGTTCATGAAACAGTGGAAGGCCCGGCTGGGCTGTGGCCTGGATTCTGGGCCCATGGCCCTGGA
GCAGAACCTGTCAGACCTGCAGCTGCAGGCAGCCGTGGAAGTGGCGGGGGACCTGGAGGTCGATTGCTACCGGGCACCCTGCTCC
GAGAGCCAGGAGGAGCTGGCCCTGCAGCACTTCATGAAGGAGAAGCTTCTGGCTGAGCTGGAGGGGAAGCTGCGTGTGTTTGAGA
ACAATGTTGCTGTCCTCAACAAGGAGGTGGAGGCCTCCCACCTGGCCCTGGCCACCTCTATCCACCAGAGCCAGCTGGACCGTGA
GCGCATCCTGAGCTTGGAGCAGAGGGTGGTGCAGGTTCAGCAGACCCTGGCCCAGAAAGACCAGGCCCTGGGCAAGCTGGAGCAG
AGCTTGCGCCTCATGGAGGAGGCCTCCTTCGATGGCACTTTCCTGTGGAAGATCACCAGTGTCACCAGGCGGTGCCATGAGTCGG
CCTGTGGCAGGACCGTCAGCCTCTTCTCCCCAGCCTTCTACACTGCCAAGTATGGCTACAAGTTGTGCCTGCGGCTGTACCTGAT
TGGAGATGGCACTGGAAAGAGAACCCATCTTTCGCTCTTCATCGTGATCATGAGAGGGGAGTATGATGCGCTGCTGCCGTGGCCT
TTCCGGAACAAGGTCACCTTCATGCTGCTGGACCAGAACAACCGTGAGCACGCCATTGACGCCTTCCGGCCTGACCTAAGCTCAG
CGTCCTTCCAGAGGCCCCAGAGTGAAACCAACGTGGCCAGTGGATGCCCACTCTTCTTCCCCCTCAGCAAACTGCAGTCACCCAA
GCACGCCTACGTWAAGGACGACACAATGTTCCTCAAGTGCATTGTGGAGACCAGCACTTAG Protein:
MASSSGSSPRPAPDENEFPFGCPPTVCQDPKEPRALCCAGCLSENPRNGEDQICPKCRGEDLQSISPGSRLRTQEKVQAEVAEAG
IGCPFAVVGCSFKGSPQFVEEHEVTSQTSHLNLLLGFMKQWKARLGCGLDSGPMALEQNLSDLQLQAAVEVAGDLEVDCYRAPCS
ESQEELALQHFMKEKLLAELEGKLRVFENNVAVLNKEVEASHLALATSIHQSQLDRERILSLEQRVVQVQQTLAQKDQALGKLEQ
SLRLMEEASFDGTFLWKITSVTRRCHESACGRTVSLFSPAFYTAKYGYKLCLRLYLIGDGTGKRTHLSLFIVIMRGEYDALLPWP
FRNKVTFMLLDQNNREHAIDAFRPDLSSASFQRPQSETNVASGCPLFFPLSKLQSPKHAYVKDDTMFLKCIVETST.

FIG. 7B

TM4SF (Transmembrane 4 superfamily), CD53

Full length sequence:
GGCGAGGCTGCTGGTGGCTGTGGAGAGCTTGGGGCTTCCTTGGTCGCACCCACCACCTGCCTGCCCACTGGTCAGCCTTCAGGGA
ACCCTGAGCACCGCCTGGTCTCTTTCCTGTGGCCAGCCCAGAACTGAAGCGCTGCCGGCATGGCGCGCGCCCTGCCTCCAGGCCGTC
AAGTACCTCATGTTCGCCTTCAACCTGCTCTTCTGGCTGGGAGGCTGTGGCCGTGCTGGGTGTCGGCATCTGGCTGGCCGCACAAC
AGGGGAGCTTTGCCACGCTGTCCTCTTCCTTCCCGTCCCTGTGGGCTGCCAACCTGCTCATCATCACCGGCGCCTTTGTCATGGC
CATCGGCTTCGTGGGCTGCCTGGGTGCCATCAAGGAGAACAAGTGCCTCCTGCTCACTTTCTTCCTGCTGCTGCTGCTGGTGTTC
CTGCTGGAGGGCACCATCGCCATCCTCTTCTTCGCCTACACGGACAAGATTGACAGGTATGCCCAGCAAGACCTGAAGAAAGGCT
TGCACCTGTACGGCACGCAGGGCAACGTGGGCCTCACCAACGCCTGGAGCATCATCCAGACCGACTTCCGCTGCTGTGGCGTCTC
CAACTACACTGACTGGTTCGAGGTGTACAACGCCACGCGGGTACCTGACTCCTGCTGCTTGGAGTTCAGTGAGAGCTGTGGGCTG
CACGCCCCGGCACTGGTGGAGGGCCGTGCTACGAGAGGTGAAGGTGTGGCTTCAGGAGAACTGCTGGCTGTGGGCATCTTTGGGC
TGTGCACGGCGCTGGTGCAGATCCTGGGCCTGAACTTCGCCATGACCATGTACTGGCAAGTGGTCAAGGCAGACACCTACTGTGC
GTAGGCCCCCCACCGCCCGCTTCTCTTTCAAAAGGACGCCCACGGGGAGATGGCCGCACCCACAGAGTGTCTTTCCCACCACCAG
CCTCGGTGCTCTTTCCCATGCTGGGAGGAGGGAGGGAGGGAAAGTTGCCTGGAGCCCCCGGAACCCTGTTTCTGGAAGGCCCTAG
CTCAGGTGGCTTTCAGGGCCTCCGGACCCCCCCTGGGAAGGGTGGCCACGTGCTGGCTTCGGAACCCAGGGCAGGGGTGGGAGGG
GCCTCCAGCACTTTTTATATTTACGTATTCTCCAAAACAGTGTTCACACGGGAGCCAACCTGTGGCCCCCAGCCTCCTGGAAAAA
AGGTTGGCGCTGGAGGAACCGGGTCTTGGCATCCTGGAGGTGGCCCCACTGGTCCTGGTGCTCCAGGCGGGGCCGTGGACCCCTC
ACCTACATTCCATAGTGGGCCCGTGGGGCTCCTGGTGCATCTTAATAAAGTGTGAGCAGCAAAAAAAAAA coding sequence:
ATGGCGCGCGCCCTGCCTCCAGGCCGTCAAGTACCTCATGTTCGCCTTCAACCTGCTCTTCTGGCTGGGAGGCTGTGGCCGTGCTGG
GTGTCGGCATCTGGCTGGCCGCACAACAGGGGAGCTTTGCCACGCTGTCCTCTTCCTTCCCGTCCCTGTGGGCTGCCAACCTGCT
CATCATCACCGGCGCCTTTGTCATGGCCATCGGCTTCGTGGGCTGCCTGGGTGCCATCAAGGAGAACAAGTGCCTCCTGCTCACT
TTCTTCCTGCTGCTGCTGCTGGTGTTCCTGCTGGAGGGCACCATCGCCATCCTCTTCTTCGCCTACACGGACAAGATTGACAGGT
ATGCCCAGCAAGACCTGAAGAAAGGCTTGCACCTGTACGGCACGCAGGGCAACGTGGGCCTCACCAACGCCTGGAGCATCATCCA
GACCGACTTCCGCTGCTGTGGCGTCTCCAACTACACTGACTGGTTCGAGGTGTACAACGCCACGCGGGTACCTGACTCCTGCTGC
TTGGAGTTCAGTGAGAGCTGTGGGCTGCACGCCCCGGCACTGGTGGAGGGCCGTGCTACGAGAGGTGAAGGTGTGGCTTCAGGAG
AACTGCTGGCTGTGGGCATCTTTGGGCTGTGCACGGCGCTGGTGCAGATCCTGGGCCTGAACTTCGCCATGACCATGTACTGGCA
AGTGGTCAAGGCAGACACCTACTGTGCGTAG Protein MARACLQAVKYLMFAFNLLFWLGGCGVLGVGIWLAAQQGSFATLSSSFPSLWAANLLIITGAFVMAIGFVGCLGAIKENKCLLLT
FFLLLLLVFLLEGTIAILFFAYTDKIDRYAQQDLKKGLHLYGTQGNVGLTNAWSIIQTDFRCCGVSNYTDWFEVYNATRVPDSCC
LEFSESCGLHAPALVEGRATRGEGVASGELLAVGIFGLCTALVQILGLNFAMIMYWQVVKADTYCA.

FIG. 8

Retinoid X receptor gamma

Full length DNA:
AGCCCAAGTTGAAGAAAGCCGGGCTGTGCCTGGAAGCCGAGAGAGGCGGTAATATTTAGAAGCTGCACAGGAGAGGAACA
TGAACTGACGAGTAAACATGTATGGAAATTATTCTCACTTCATGAAGTTTCCCGCAGGCTATGGAGGCTCCCCTGGCCAC
ACTGGCTCTACATCCATGAGCCCATCAGCAGCCTTGTCCACAGGGAAGCCAATGGACAGCCACCCCAGCTACACAGATAC
CCCAGTGAGTGCCCCACGGACTCTGAGTGCAGTGGGGACCCCCCTCAATGCCCTGGGCTCTCCATATCGAGTCATCACCT
CTGCCATGGGCCCACCCTCAGGAGCACTTGCAGCGCCTCCAGGAATCAACTTGGTTGCCCCACCCAGCTCTCAGCTAAAT
GTGGTCAACAGTGTCAGCAGTTCAGAGGACATCAAGCCCTTACCAGGGCTTCCCGGGATTGGAAACATGAACTACCCATC
CACCAGCCCCGGATCTCTGGTTAAACACATCTGTGCTATCTGTGGAGACAGATCCTCAGGAAAGCACTACGGGGTATACA
GTTGTGAAGGCTGCAAAGGGTTCTTCAAGAGGACGATAAGGAAGGACCTCATCTACACGTGTCGGGATAATAAAGACTGC
CTCATTGACAAGCGTCAGCGCAACCGCTGCCAGTACTGTCGCTATCAGAAGTGCCTTGTCATGGGCATGAAGAGGGAAGC
TTGTGCAAAGAAGGAAAGACAGAGGAGCCGAGAGCGAGCTGAGAGTGAGGCAGAATGTGCTACCAGTGGTCATGAAGACA
TGCCTGTGGAGAGGATTCTAGAAGCTGAACTTGCTGTTGACCCAAAGACAGAATCCTATGGTGACATGAATATGGAGAAC
TCGACAAATGACCCTGTTACCAACATATGTCATGCTGCTGACAAGCAGCTTCACACCCTCGGTGAATGGGCCAAGCGTAT
TCCCCACTTCTCTGACCTCACCTTGGAGGACCAGGTCATTGTGCTTCGGACAGGGTGGAATGAATTGCTGATTGCCTCTT
TCTCCCACCGCTCAGTTTCCGTGGAGGATGGCATCCCTCTGGCCACGGGTTTACATGTCCACCGGAGCAGTGCCCACAGT
GCTGGGGTCGGCTCCATCTTTGACAGAGCTCTAACTGAGCTGGTTTCCAAACTGAAAGACATGCAGGTGGACAAGTCGGA
ACTGGGATGCCTGCGAGCCATTGTTCTCTTTCAACCCCAGATGCCCAAGGGCCTGCCCACCCCCTTTGAGGTGGAGACTC
TGCGAAAGAAGGTTTATGCCACCCTTGAGGCCCACCACCAAGCAGAATATCCGGAACAGCCAGGCAAGGTTTGCCAAGCT
GCTGTGCGCCTCCCAGCTCTGCGTTCCATTGGCTTGAAATGCCTGGAGCACCTCTTCTTCTTCAAGCTCATCGGGGACAC
CCCCATTGACACCTTCCTCATGGAGATGTTGGAGACCCCGCTGCAGATCACCTGAGCCCCACCAGCCAAAGCCTCCCCAC
CCAGGATGACCCCTGGGCAGGTGTGTGTGGACCCCCACCCTGCACTTTCCTCCACCTCCCACCCTGACCCCCTTCCTGTC
CCCAAAATGTGATGCTTATAATAAAGAAAACCTTTCTACAA Protein MYGNYSHFMKFPAGYGGSPGHTGSTSMSPSAALSTGKPMDSHPSYTDTPVSAPRTLSAVGTPLNALGSPYRVITSAMGPPSGALA
APPGINLVAPPSSQLNVVNSVSSSEDIKPLPGLPGIGNMNYPSTSPGSLVKHICAICGDRSSGKHYGVYSCEGCKGFFKRTIRKD
LIYTCRDNKDCLIDKRQRNRCQYCRYQKCLVMGMKREACAKKERQRSRERAESEAECATSGHEDMPVERILEAELAVDPKTESYG
DMNMENSTNDPVTNICHAADKQLHTLGEWAKRIPHFSDLTLEDQVIVLRTGWNELLIASFSHRSVSVEDGIPLATGLHVHRSSAH
SAGVGSIFDRALTELVSKLKDMQVDKSELGCLRAIVLFQPQMPKGLPTPFEVETLRKKVYATLEAHHQAEYPEQPGKVCQAAVRL
PALRSIGLKCLEHLFFFKLIGDTPIDTFLMEMLETPLQIT

FIG.9

Cytosolic resiniferatoxin binding protein RBP-26

The full length nucleotide sequence (1237 bp) is tentatively determined as follows:

ATGGCGTTGGAGGTCGGCGATATGGAAGATGGGCAGCTTTCCGACTCGGATTCCGACATGACGGTCGCACCCAGCGACAGGCCGC
TGCAATTGCCAAAAGTGCTAGGTGGCGACAGTGCTATGAGGGCCTTCCAGAACACGGCAACTGCATGTGCACCAGTATCACATTA
TCGAGCTGTTGAAAGTGTGGATTCAACTGAAGAAAGTTTTTCTGATTCAGATGATGATAGCTGTCTTTGGAAACGCAAACGACAG
AAATGTTTTAACCCTCCTCCCAAACCAGAGCCTTTTCAGTTTGGCCAGAGCAGTCAGAAACCACCTGTTGCTGGAGGAAAGAAGA
TTAACAACATATGGGGTGCTGTGCTGCAGGAACAGAATCAAGATGCAGTGGCCACTGAACTTGGTATCTTGGGAATGGAGGGCAC
TATTGACAGAAGCAGACAATCCGAGACCTACAATTATTTGCTTGCCAAGAAACTTAGGAAGGAATCTCAAGAGCATACAAAAGAT
CTAGACAAGGAACTAGATGAATATATGCATGGTGGCAAAAAAATGGGATCAAAGGAAGAGGAAAATGGGCAAGGTCATCTCAAAA
GGAAACGACCTGTCAAAGACAGGCTAGGGAACAGACCAGAAATGAACTATAAAGGTCGATACGAGATCACAGCGGAAGATTCTCA
AGAGAAAGTGGCTGATGAAATTTCATTCAGGTTACAGGAACCAAAGAAAGACCTGATAGCCCCGAGTAGTGAGGATTATTGGTAAC
AAAAAGGCAATTGAACTTCTGATGGAAACCGCTGAAGTTGAACAAAATGGTGGTCTCTTTATAATGAATGGTAGTCGAAGAAGAA
CACCAGGTGGAGTTTTTCTGAATCTCTTGAAAAACACTCCTAGTATCAGCGAGGAACAAATTAAGGACATTTTCTACATTGAAAA
CCAAAAGGAATATGAAAATAAAAAAGCTGCTAGGAAGAGGAGAACACAAGTGTTGGGGAAAAAGATGAAACAAGCTATTAAAAGT
CTAAATTTTCAAGAAGATGATGATACATCACGAGAAACTTTTGCAAGTGACACGAATGAGGCCTTGGCCTCTCTTGATGAGTCAC
AGGAAGGACATGCAGAAGCCAAGTTGGAGGCAGAGGAAGCCATTGAAGTTGATCATTCTCATGATTTGGACATCTTTTAA

The translation product (412 amino acids) from above sequence is as follows:
MALEVGDMEDGQLSDSDSDMTVAPSDRPLQLPKVLGGDSAMRAFQNTATACAPVSHYRAVESVDSSEESFSDSDDDSCLWKRKRQ
KCFNPPPKPEPFQFGQSSQKPPVAGGKKINNIWGAVLQEQNQDAVATELGILGMEGTIDRSRQSETYNYLLAKKLRKESQEHTKD
LDKELDEYMHGGKKMGSKEEENGQGHLKRKRPVKDRLGNRPEMNYKGRYEITAEDSQEKVADEISFRLQEPKKDLIARVVRIIGN
KKAIELLMETAEVEQNGGLFIMNGSRRRTPGGVFLNLLKNTPSISEEQIKDIFYIENQKEYENKKAARKRRTQVLGKKMKQAIKS
LNFQEDDDTSRETFASDTNEALASLDESQEGHAEAKLEAEFAIEVDHSHDLDIF.

FIG.10

Protein kinase c inhibitor protein

Human PKCI sequence

```
  1 CACCTGCGCA GGCTTGGCTG CGCCTCTCGC GCCGCACGCT CTGGGGTTCC
 51 TCCCTTCTTC CGAGCCTCTC CTCTGGCCGC CGCGCGGGAG AGAGGCCGAG
101 ATGGCAGATG AGATTGCCAA GGCTCAGGTC GCTCGGCCTG GTGGCGACAC
151 GATCTTTGGG AAGATCATCC GCAAGGAAAT ACCAGCCAAA ATCATTTTTG
201 AGGATGACCG GTGCCTTGCT TTCCATGACA TTTCCCCTCA AGCACCAACA
251 CATTTTCTGG TGATACCCAA GAAACATATA TCCCAGATTT CTGTGGCAGA
301 AGATGATGAT GAAAGTCTTC TTGGACACTT AATGATTGTT GGCAAGAAAT
351 GTGCTGCTGA TCTGGGCCTG AATAAGGGTT ATCGAATGGT GGTGAATGAA
401 GGTTCAGATG GTGGACAGTC TGTCTATCAC GTTCATCTCC ATGTTCTTGG
451 AGGTCGGCAA ATGCATTGGC CTCCTGGTTA AGCACGTTTT GGGGATAATT
501 TTCTCTTCTT TAGGCAATGA TTAAGTTAGG CAATTTCCAG TATGTTAAGT
551 AACACNCTTA TTTTTGCCTG TGTATGGAGA GATTCAAGAA ATAATTTTAA
601 AACCGCATAC ATAATAAAAG ACATTGTTGC ATGGCTTAT
```

POLYNUCLEOTIDES ENCODING HUMAN ADA2

This is a Continuation-in-Part Application of U.S. Provisional Application Ser. No. 60/002,993, filed Aug. 30, 1995 (now abandoned), which is entitled to priority under 35 U.S.C. §120.

This invention relates to newly identified polynucleotides, polypeptides encoded by such polynucleotides, the use of such polynucleotides and polypeptides, as well as the production of such polynucleotides and polypeptides. The invention also relates to inhibiting the action of such polypeptides.

Identification and sequencing of human genes is a major goal of modern scientific research. For example, by identifying genes and determining their sequences, scientists have been able to make large quantities of valuable human "gene products." These include human insulin, interferon, Factor VIII, tumor necrosis factor, human growth hormone, tissue plasminogen activator, and numerous other compounds. Additionally, knowledge of gene sequences can provide the key to treatment or cure of genetic diseases (such as muscular dystrophy and cystic fibrosis).

In accordance with one aspect of the present invention, there are provided novel mature polypeptides, as well as biologically active and diagnostically or therapeutically useful fragments, analogs and derivatives thereof. The polypeptides of the present invention are of human origin.

In accordance with another aspect of the present invention, there are provided isolated nucleic acid molecules encoding the polypeptides, including mRNAs, DNAs, cDNAs, genomic DNAs as well as analogs and biologically active and diagnostically or therapeutically useful fragments thereof.

In accordance with yet a further aspect of the present invention, there is provided a process for producing such polypeptides by recombinant techniques comprising culturing recombinant prokaryotic and/or eukaryotic host cells, containing a nucleic acid sequence of the present invention, under conditions promoting expression of said proteins and subsequent recovery of said proteins.

In accordance with yet a further aspect of the present invention, there is provided a process for utilizing such polypeptides, or polynucleotides encoding such polypeptide for therapeutic and diagnostic purposes.

In accordance with yet a further aspect of the present invention, there is also provided nucleic acid probes comprising nucleic acid molecules of sufficient length to specifically hybridize to the nucleic acid sequences.

In accordance with yet a further aspect of the present invention, there are provided antibodies against such polypeptides.

In accordance with another aspect of the present invention, there are provided agonists to the polypeptides.

In accordance with yet another aspect of the present invention, there are provided antagonists to such polypeptides, which may be used to inhibit the action of such polypeptides, for therapeutic and diagnostic purposes.

In accordance with still another aspect of the present invention, there are provided diagnostic assays for detecting diseases related to the under-expression of the polypeptides of the present invention and mutations in the nucleic acid sequences encoding such polypeptides.

In accordance with yet a further aspect of the present invention, there is provided a process for utilizing such polypeptides, or polynucleotides encoding such polypeptides, for in vitro purposes related to scientific research, synthesis of DNA and manufacture of DNA vectors.

In the case where the polypeptides of the present invention are receptors, there are provided processes for using the receptor to screen for receptor antagonists and/or agonists and/or receptor ligands.

These and other aspects of the present invention should be apparent to those skilled in the art from the teachings herein.

Table 1 sets forth information regarding identifying polynucleotide clone numbers, identification of the polynucleotide sequence which corresponds to the putative identification of the polypeptide encoded by the polynucleotide, and cross-referencing to the SEQ ID NOS. as set forth in the sequence listing.

Table 2 includes information regarding identifying polypeptide numbers, identification of the SEQ ID NOS. of the polypeptides, and cross-reference to the SEQ ID NO. which sets forth the amino acid sequence which corresponds to a given polypeptide in the sequence listing.

BRIEF DESCRIPTION OF THE DRAWINGS

FIG. 1 shows the full length polynucleotide sequence (SEQ ID NO:1) of the HBGBA67X clone and correlates the coding region with the derived amino acids (127 amino acids whose entire sequence (SEQ ID NO:12) is also shown for the full length amyloid-like protein present in breast tissue.

FIGS. 2A–2B show the complete nucleotide (SEQ ID NO:2) and amino acid sequence (SEQ ID NO:13) of the hADA2 gene and protein.

FIGS. 3A–3B show the full length sequence of the TFIId homolog clone (SEQ ID NO:3) including the full length sequence of the polynucleotide coding for TATA related factor (TRF) (SEQ ID NO:14).

FIG. 4 shows full length cDNA (SEQ ID NO:4) and deduced amino acid sequence (SEQ ID NO:15) of hRPB 11.

FIGS. 5A–5B show the full nucleotide sequence (SEQ ID NO:5) of the IRF3 gene and amino acid sequence (SEQ ID NO:16) resulting protein. The predicted molecular weight of IRF3 is 47,087; the predicted isoelectric is 5.06; and the net charge equals −14.

FIG. 6 shows individually the full length sequence (SEQ ID NO:6) of the TM4SF gene, the coding region sequence portion and the amino acid sequence (SEQ ID NO:17) of the translation product TM4SF.

FIGS. 7A–7B show the full length nucleotide sequence (SEQ ID NO:7) of TNFR AF1 C1, the complete coding sequence region of the full length sequence and the derived amino acid sequence (SEQ ID NO:18) of the resulting protein.

FIG. 8 shows the full length sequence (SEQ ID NO:8), the coding region sequence and the derived amino acid sequence (SEQ ID NO:19) of the expression product protein of TM4SF (transmembrane 4 super family) CD53.

FIG. 9 shows the full length cDNA (SEQ ID NO:9) and the resulting expression of the product protein (SEQ ID NO:20) of its coding region for retenoid receptor gamma.

FIG. 10 shows the full length nucleotide sequence (SEQ ID NO:10) (1237 bp) and the translation product (412 amino acid) resulting from the nucleotide sequence for the cytosolic resiniferatoxin binding protein RBP-26.

FIG. 11 shows the nucleotide sequence (SEQ ID NO:11) for the human protein (SEQ ID NO:22) kinase C inhibitor protein.

In accordance with an aspect of the present invention, there are provided isolated nucleic acids (polynucleotides)

which code for mature polypeptides having the deduced amino acid sequences shown in the FIGS. 1–11 or for the mature polypeptides encoded by the cDNA of the clone deposited as ATCC Deposit No. 97242 on Aug. 15, 1995 with ATCC, 10801 University Boulevard, Manassas, Va. 20110-2209.

The polynucleotides of the present invention may be in the form of RNA or in the form of DNA, which DNA includes cDNA, genomic DNA, and synthetic DNA. The DNA may be double-stranded or single-stranded, and if single stranded may be the coding strand or non-coding (anti-sense) strand. The coding sequence which encodes the mature polypeptide may be identical to the coding sequence shown in SEQ ID NOS:1–11) or that of the deposited clone or may be a different coding sequence which coding sequence, as a result of the redundancy or degeneracy of the genetic code, encodes the same mature polypeptide as the DNA of SEQ ID NOS:1–11 or the deposited cDNA.

The polynucleotides which code for the mature polypeptides of FIGS. 1–11 or for the mature polypeptides encoded by the deposited cDNA may include, but are not limited to: only the coding sequence for the mature polypeptide; the coding sequence for the mature polypeptide and additional coding sequence such as a leader or secretory sequence or a proprotein sequence; the coding sequence for the mature polypeptide (and optionally additional coding sequence) and non-coding sequence, such as introns or non-coding sequence (SEQ ID NO:1) 5' and/or 3' of the coding sequence (SEQ ID NO:2) for the mature polypeptide.

Thus, the term "polynucleotide encoding a polypeptide" encompasses a polynucleotide which includes only coding sequence for the polypeptide as well as a polynucleotide which includes additional coding and/or non-coding sequence.

The present invention further relates to variants of the hereinabove described polynucleotides which code for fragments, analogs and derivatives of the polypeptide having the deduced amino acid sequences of FIGS. 1–11 or the polypeptides encoded by the cDNA of the deposited clone. The variant of the polynucleotide may be a naturally occurring allelic variant of the polynucleotide or a non-naturally occurring variant of the polynucleotide.

Thus, the present invention includes polynucleotides encoding the same mature polypeptides as shown in FIG. 1 or the same mature polypeptides encoded by the cDNA of the deposited clone as well as variants of such polynucleotides which variants code for a fragment, derivative or analog of the polypeptides of FIGS. 1–11 or the polypeptides encoded by the cDNA of the deposited clone. Such nucleotide variants include deletion variants, substitution variants and addition or insertion variants.

As hereinabove indicated, the polynucleotides may have a coding sequence which is a naturally occurring allelic variant of the coding sequences shown in FIGS. 1–11 or of the coding sequences of the deposited clone. As known in the art, an allelic variant is an alternate form of a polynucleotide sequence which may have a substitution, deletion or addition of one or more nucleotides, which does not substantially alter the function of the encoded polypeptide.

The present invention also includes polynucleotides, wherein the coding sequence for the mature polypeptide may be fused in the same reading frame to a polynucleotide sequence which aids in expression and secretion of a polypeptide from a host cell, for example, a leader sequence which functions as a secretory sequence for controlling transport of a polypeptide from the cell. The polypeptide having a leader sequence is a preprotein and may have the leader sequence cleaved by the host cell to form the mature form of the polypeptide. The polynucleotides may also code for a proprotein which is the mature protein plus additional 5' amino acid residues. A mature protein having a prosequence is a proprotein and is an inactive form of the protein. Once the prosequence is cleaved an active mature protein remains.

Thus, for example, the polynucleotide of the present invention may code for a mature protein, or for a protein having a prosequence or for a protein having both a prosequence and a presequence (leader sequence).

The polynucleotides of the present invention may also have the coding sequence fused in frame to a marker sequence which allows for purification of the polypeptide of the present invention. The marker sequence may be a hexa-histidine tag supplied by a pQE-9 vector to provide for purification of the mature polypeptide fused to the marker in the case of a bacterial host, or, for example, the marker sequence may be a hemagglutinin (HA) tag when a mammalian host, e.g. COS-7 cells, is used. The HA tag corresponds to an epitope derived from the influenza hemagglutinin protein (Wilson et al., *Cell*, 37:767 (1984)).

The term "gene" means the segment of DNA involved in producing a polypeptide chain; it includes regions preceding and following the coding region (leader and trailer) as well as intervening sequences (introns) between individual coding segments (exons).

Fragments of the full length genes of the present invention may be used as hybridization probes for a cDNA library to isolate the full length cDNA and to isolate other cDNAs which have a high sequence similarity to the gene or similar biological activity. Probes of this type preferably have at least 30 bases and may contain, for example, 50 or more bases. The probe may also be used to identify a cDNA clone corresponding to a full length transcript and a genomic clone or clones that contain the complete gene including regulatory and promotor regions, exons and introns. An example of a screen comprises isolating the coding region of one of the genes by using the known DNA sequence to synthesize an oligonucleotide probe. Labeled oligonucleotides having a sequence complementary to that of the gene of the present invention are used to screen a library of human cDNA, genomic DNA or mRNA to determine which members of the library the probe hybridizes to.

The present invention further relates to polynucleotides which hybridize to the hereinabove-described sequences if there is at least 70%, preferably at least 90%, and more preferably at least 95% identity between the sequences. The present invention particularly relates to polynucleotides which hybridize under stringent conditions to the hereinabove-described polynucleotides. As herein used, the term "stringent conditions" means hybridization will occur only if there is at least 95% and preferably at least 97% identity between the sequences. The polynucleotides which hybridize to the hereinabove described polynucleotides in a preferred embodiment encode polypeptides which either retain substantially the same biological function or activity as the mature polypeptide encoded by the cDNAs of FIGS. 1–11 (SEQ ID NOS:1–11) or the deposited cDNA(s).

Alternatively, the polynucleotides may have at least 20 bases, preferably 30 bases, and more preferably at least 50 bases which hybridize to a polynucleotide of the present invention and which have an identity thereto, as hereinabove described, and which may or may not retain activity. For example, such polynucleotides may be employed as probes for the polynucleotides any of SEQ ID NOS:1–11, for example, for recovery of the polynucleotide or as a diagnostic probe or as a PCR primer.

Thus, the present invention is directed to polynucleotides having at least a 70% identity, preferably at least 90% and more preferably at least a 95% identity to polynucleotides which encode the polypeptides of SEQ ID NOS: 12–22, as well as fragments thereof, which fragments have at least 30 bases and preferably at least 50 bases and to polypeptides encoded by such polynucleotides.

The deposit(s) referred to herein will be maintained under the terms of the Budapest Treaty on the International Recognition of the Deposit of Micro-organisms for purposes of Patent Procedure. These deposits are provided merely as convenience to those of skill in the art and are not an admission that a deposit is required under 35 U.S.C. §112. The sequence of the polynucleotides contained in the deposited materials, as well as the amino acid sequence of the polypeptides encoded thereby, are incorporated herein by reference and are controlling in the event of any conflict with any description of sequences herein. A license may be required to make, use or sell the deposited materials, and no such license is hereby granted.

The present invention further relates to polypeptides which have the deduced amino acid sequence of SEQ ID NOS. 12–22 or which have the amino acid sequences encoded by the deposited cDNAs, as well as fragments, analogs and derivatives of such polypeptides.

The terms "fragment", "derivative" and "analog" when referring to the polypeptides of SEQ ID NOS. 12–22 or those encoded by the deposited cDNA, means polypeptides which retain essentially the same biological function or activity as such polypeptide. Thus, an analog and derivative includes a proprotein which can be activated by cleavage of the proprotein portion to produce an active mature polypeptide.

The polypeptides of the present invention may be recombinant polypeptides, natural polypeptides or synthetic polypeptides, preferably recombinant polypeptides.

The fragments, derivatives or analogs of the polypeptides of SEQ ID NOS. 12–22 or those encoded by the deposited cDNAs may be (i) those in which one or more of the amino acid residues are substituted with a conserved or non-conserved amino acid residue (preferably a conserved amino acid residue) and such substituted amino acid residue may or may not be one encoded by the genetic code, (ii) those in which one or more of the amino acid residues includes a substituent group, (iii) those in which the mature polypeptide is fused with another compound, such as a compound to increase the half-life of the polypeptide (for example, polyethylene glycol) or (iv) those in which the additional amino acids are fused to the mature polypeptide, such as a leader or secretory sequence or a sequence which is employed for purification of the mature polypeptide or a proprotein sequence. Such fragments, derivatives and analogs are deemed to be within the scope of those skilled in the art from the teachings herein.

The polypeptides and polynucleotides of the present invention are preferably provided in an isolated form, and preferably are purified to homogeneity.

The term "isolated" means that the material is removed from its original environment (e.g., the natural environment if it is naturally occurring). For example, a naturally-occurring polynucleotide or polypeptide present in a living animal is not isolated, but the same polynucleotide or polypeptide, separated from some or all of the coexisting materials in the natural system, is isolated. Such polynucleotides could be part of a vector and/or such polynucleotides or polypeptides could be part of a composition, and still be isolated in that such vector or composition is not part of its natural environment.

The polypeptides of the present invention include the polypeptides of SEQ ID NOS: 12–22 (in particular the mature polypeptides) as well as polypeptides which have at least 70% similarity (preferably a 70% identity) to the polypeptides of SEQ ID NOS: 12–22 and more preferably a 90% similarity (more preferably a 90% identity) to the polypeptides of SEQ ID NOS: 12–22 and still more preferably a 95% similarity (still more preferably a 90% identity) to the individual polypeptides of SEQ ID NOS: 12–22 and also include portions of such polypeptides with such portion of the polypeptide generally containing at least 30 amino acids and more preferably at least 50 amino acids.

As known in the art "similarity" between two polypeptides is determined by comparing the amino acid sequence and its conserved amino acid substitutes of one polypeptide to the sequence of a second polypeptide.

Fragments or portions of the polypeptides of the present invention may be employed for producing the corresponding full-length polypeptide by peptide synthesis; therefore, the fragments may be employed as intermediates for producing the full-length polypeptides. Fragments or portions of the polynucleotides of the present invention may be used to synthesize full-length polynucleotides of the present invention.

The present invention also relates to vectors which include polynucleotides of the present invention, host cells which are genetically engineered with vectors of the invention and the production of polypeptides of the invention by recombinant techniques.

Host cells are genetically engineered (transduced or transformed or transfected) with the vectors of this invention which may be, for example, a cloning vector or an expression vector. The vector may be, for example, in the form of a plasmid, a viral particle, a phage, etc. The engineered host cells can be cultured in conventional nutrient media modified as appropriate for activating promoters, selecting transformants or amplifying the genes of the present invention. The culture conditions, such as temperature, pH and the like, are those previously used with the host cell selected for expression, and will be apparent to the ordinarily skilled artisan.

The polynucleotides of the present invention may be employed for producing polypeptides by recombinant techniques. Thus, for example, the polynucleotides may be included in any one of a variety of expression vectors for expressing the corresponding polypeptide. Such vectors include chromosomal, nonchromosomal and synthetic DNA sequences, e.g., derivatives of SV40; bacterial plasmids; phage DNA; baculovirus; yeast plasmids; vectors derived from combinations of plasmids and phage DNA, viral DNA such as vaccinia, adenovirus, fowl pox virus, and pseudorabies. However, any other vector may be used as long as it is replicable and viable in the host.

The appropriate DNA sequence may be inserted into the vector by a variety of procedures. In general, the DNA sequence is inserted into an appropriate restriction endonuclease site(s) by procedures known in the art. Such procedures and others are deemed to be within the scope of those skilled in the art.

The DNA sequence in the expression vector is operatively linked to an appropriate expression control sequence(s)

(promoter) to direct mRNA synthesis. As representative examples of such promoters, there may be mentioned: LTR or SV40 promoter, the *E. coli.* lac or trp, the phage lambda $P_L$ promoter and other promoters known to control expression of genes in prokaryotic or eukaryotic cells or their viruses. The expression vector also contains a ribosome binding site for translation initiation and a transcription terminator. The vector may also include appropriate sequences for amplifying expression.

In addition, the expression vectors preferably contain one or more selectable marker genes to provide a phenotypic trait for selection of transformed host cells such as dihydrofolate reductase or neomycin resistance for eukaryotic cell culture, or such as tetracycline or ampicillin resistance in *E. coli.*

The vector containing the appropriate DNA sequence as hereinabove described, as well as an appropriate promoter or control sequence, may be employed to transform an appropriate host to permit the host to express the protein.

As representative examples of appropriate hosts, there may be mentioned: bacterial cells, such as *E. coli,* Streptomyces, *Salmonella typhimurium;* fungal cells, such as yeast; insect cells such as Drosophila S2 and Spodoptera Sf9; animal cells such as CHO, COS or Bowes melanoma; adenoviruses; plant cells, etc. The selection of an appropriate host is deemed to be within the scope of those skilled in the art from the teachings herein.

More particularly, the present invention also includes recombinant constructs comprising one or more of the sequences as broadly described above. The constructs comprise a vector, such as a plasmid or viral vector, into which a sequence of the invention has been inserted, in a forward or reverse orientation. In a preferred aspect of this embodiment, the construct further comprises regulatory sequences, including, for example, a promoter, operably linked to the sequence. Large numbers of suitable vectors and promoters are known to those of skill in the art, and are commercially available. The following vectors are provided by way of example; Bacterial: pQE70, pQE60, pQE-9 (Qiagen), pBS, pD10, phagescript, psiX174, pbluescript SK, pbsks, pNH8A, pNH16a, pNH18A, pNH46A (Stratagene); ptrc99a, pKK223-3, pKK233-3, pDR540, pRIT5 (Pharmacia); Eukaryotic: pWLNEO, pSV2CAT, pOG44, pXT1, pSG (Stratagene) pSVK3, pBPV, pMSG, pSVL (Pharmacia). However, any other plasmid or vector may be used as long as they are replicable and viable in the host.

Promoter regions can be selected from any desired gene using CAT (chloramphenicol transferase) vectors or other vectors with selectable markers. Two appropriate vectors are pKK232-8 and pCM7. Particular named bacterial promoters include lacI, lacZ, T3, T7, gpt, lambda $P_R$, $P_L$ and trp. Eukaryotic promoters include CMV immediate early, HSV thymidine kinase, early and late SV40, LTRs from retrovirus, and mouse metallothionein-I. Selection of the appropriate vector and promoter is well within the level of ordinary skill in the art.

In a further embodiment, the present invention relates to host cells containing the above-described constructs. The host cell can be a higher eukaryotic cell, such as a mammalian cell, or a lower eukaryotic cell, such as a yeast cell, or the host cell can be a prokaryotic cell, such as a bacterial cell. Introduction of the construct into the host cell can be effected by calcium phosphate transfection, DEAE-Dextran mediated transfection, or electroporation (Davis, Dibner and Battey, Basic Methods in Molecular Biology, (1986)).

The constructs in host cells can be used in a conventional manner to produce the gene product encoded by the recombinant sequence. Alternatively, the polypeptides of the invention can be synthetically produced by conventional peptide synthesizers.

Mature proteins can be expressed in mammalian cells, yeast, bacteria, or other cells under the control of appropriate promoters. Cell-free translation systems can also be employed to produce such proteins using RNAs derived from the DNA constructs of the present invention. Appropriate cloning and expression vectors for use with prokaryotic and eukaryotic hosts are described by Sambrook et al., Molecular Cloning: A Laboratory Manual, Second Edition, Cold Spring Harbor, N.Y., (1989), the disclosure of which is hereby incorporated by reference.

Transcription of the DNA encoding the polypeptides of the present invention by higher eukaryotes is increased by inserting an enhancer sequence into the vector. Enhancers are cis-acting elements of DNA, usually about from 10 to 300 bp that act on a promoter to increase its transcription. Examples including the SV40 enhancer on the late side of the replication origin bp 100 to 270, a cytomegalovirus early promoter enhancer, the polyoma enhancer on the late side of the replication origin, and adenovirus enhancers.

Generally, recombinant expression vectors will include origins of replication and selectable markers permitting transformation of the host cell, e.g., the ampicillin resistance gene of *E. coli* and *S. cerevisiae* TRP1 gene, and a promoter derived from a highly-expressed gene to direct transcription of a downstream structural sequence. Such promoters can be derived from operons encoding glycolytic enzymes such as 3-phosphoglycerate kinase (PGK), α-factor, acid phosphatase, or heat shock proteins, among others. The heterologous structural sequence is assembled in appropriate phase with translation initiation and termination sequences, and preferably, a leader sequence capable of directing secretion of translated protein into the periplasmic space or extracellular medium. Optionally, the heterologous sequence can encode a fusion protein including an N-terminal identification peptide imparting desired characteristics, e.g., stabilization or simplified purification of expressed recombinant product.

Useful expression vectors for bacterial use are constructed by inserting a structural DNA sequence encoding a desired protein together with suitable translation initiation and termination signals in operable reading phase with a functional promoter. The vector will comprise one or more phenotypic selectable markers and an origin of replication to ensure maintenance of the vector and to, if desirable, provide amplification within the host. Suitable prokaryotic hosts for transformation include *E. coli, Bacillus subtilis, Salmonella typhimurium* and various species within the genera Pseudomonas, Streptomyces, and Staphylococcus, although others may also be employed as a matter of choice.

As a representative but nonlimiting example, useful expression vectors for bacterial use can comprise a selectable marker and bacterial origin of replication derived from commercially available plasmids comprising genetic elements of the well known cloning vector pBR322 (ATCC 37017). Such commercial vectors include, for example, pKK223-3 (Pharmacia Fine Chemicals, Uppsala, Sweden) and GEM1 (Promega Biotec, Madison, Wis., USA). These pBR322 "backbone" sections are combined with an appropriate promoter and the structural sequence to be expressed.

Following transformation of a suitable host strain and growth of the host strain to an appropriate cell density, the selected promoter is induced by appropriate means (e.g., temperature shift or chemical induction) and cells are cultured for an additional period.

Cells are typically harvested by centrifugation, disrupted by physical or chemical means, and the resulting crude extract retained for further purification.

Microbial cells employed in expression of proteins can be disrupted by any convenient method, including freeze-thaw cycling, sonication, mechanical disruption, or use of cell lysing agents, such methods are well know to those skilled in the art.

Various mammalian cell culture systems can also be employed to express recombinant protein. Examples of mammalian expression systems include the COS-7 lines of monkey kidney fibroblasts, described by Gluzman, Cell, 23:175 (1981), and other cell lines capable of expressing a compatible vector, for example, the C127, 3T3, CHO, HeLa and BHK cell lines. Mammalian expression vectors will comprise an origin of replication, a suitable promoter and enhancer, and also any necessary ribosome binding sites, polyadenylation site, splice donor and acceptor sites, transcriptional termination sequences, and 5' flanking nontranscribed sequences. DNA sequences derived from the SV40 splice, and polyadenylation sites may be used to provide the required nontranscribed genetic elements.

The polypeptides can be recovered and purified from recombinant cell cultures by methods including ammonium sulfate or ethanol precipitation, acid extraction, anion or cation exchange chromatography, phosphocellulose chromatography, hydrophobic interaction chromatography, affinity chromatography, hydroxylapatite chromatography and lectin chromatography. Protein refolding steps can be used, as necessary, in completing configuration of the mature protein. Finally, high performance liquid chromatography (HPLC) can be employed for final purification steps.

The polypeptides of the present invention may be a naturally purified product, or a product of chemical synthetic procedures, or produced by recombinant techniques from a prokaryotic or eukaryotic host (for example, by bacterial, yeast, higher plant, insect and mammalian cells in culture). Depending upon the host employed in a recombinant production procedure, the polypeptides of the present invention may be glycosylated or may be non-glycosylated. Polypeptides of the invention may also include an initial methionine amino acid residue.

The amyloid-like gene and gene product may be employed as part of a diagnostic process for the early detection of pre-cancerous growth or cancer in the breast. The amyloid protein forms amyloid fibrils which in turn are capable of attracting calcium molecules leading to calcium deposition and calcification. Micro-fibrils and micro-calcification caused by microinjury in the breast tissue result in densified breast tissue which is an early symptom detectable by mammography. The amyloid-like protein gene according to the invention was isolated and recovered as a full length gene by computer-assisted analysis of expression sequence tag data basis from a primary breast cancer library, a normal breast library, an activated monocyte library and an embryonic library. The assembly of ESTs represents a full length gene which is illustrated in FIG. 1. Full length human ADA2 nucleotide sequence was isolated from a 12 week old early stage human primary testes lambda library.

The expression levels of the amyloid-like protein according to the invention may be detectable in the serum and/or ductal fluid of the breast due to its secretory nature, thus the amyloid-like protein may be employed as a target for detection in such breast fluids. Further, examination of tissue samples from the breast for increased levels of the amyloid protein according to the invention may be helpful as part of an overall diagnostic regimen to screen for abnormal breast tissue growth or for breast cancer.

The amyloid-like protein according to the invention is toxic to surrounding breast cells which leads to apoptosis. The deposition of this protein in the breast tissue may be an early lesion for cancerous growth in the breast. Thus, this gene may be a target for breast cancer diagnosis.

Human transcriptional regulator hADA2 is the human homolog of a yeast factor identified as being important for mediating the transcriptional activation properties of the Herpes Simplex transactivator VP16. It is possible that being able to control the activity of this factor (perhaps through anti-sense or screened antagonists) will allow the regulation of specific viral and human genes whose expression is controlled by this factor. This could lead to the controlled regulation of certain medically important genes. Furthermore, it is possible that disruption of this gene cold result in unregulated transcription leading to cancer, in which case gene therapy would be medically important. Administration of HADA2 via gene therapy may be employed to treat cancer since disruption of the HADA2 gene results in unregulated transcription. We have recently mapped the chromosomal location of this gene to 17q12-21. The gene encoding the HADA2 protein was isolated from a 12 week old human primary testes library.

Modulating the activity of the human transcription regulator HADA2 may be employed to enhance or reduce the amount of a particular gene product produced. For example, in the case of an elevated level of a polypeptide the gene responsible may be down-regulated by inhibiting HADA2. Likewise, if an up-regulation of a gene product is desired, e.g., growth hormone, HADA2 may be stimulated.

Human transcription regulator factor (hTRF) is a homolog of the TATA Box Binding protein which plays a pivotal role in the expression of all genes. The full length cDNA of TRF was isolated by screening a human testes library. The hRPB11 gene was isolated from a subtracted human pituitary library. It is possible that lack or overexpression of this gene could lead to unregulated transcription leading to cancer. The human transcription factor hTRF may play a pivotal role in the expression of nearly all human genes since it is thought to bind to the "TATA box" upstream of all translated genes. Accordingly, modulation of hTRF, via gene therapy, stimulation and antagonism may be employed to control gene expression. Lack of hTRF may cause unregulated transcription which may lead to cancer. Accordingly administration of hTRF protein, or administration of the hTRF gene via gene therapy may be employed to treat cancer.

The human RNA polymerase subunits hRPB8, hRPB10 and hRPB11 play vital roles in mRNA synthesis since they possess the catalytic machinery for the formation of the 3'-5' phosphodiester bonds between ribonucleoside triphosphates and respond to signals from the multiple factors involved in regulating their function during initiation and elongation of mRNA synthesis. These subunits are able to support normal yeast cell growth in vivo. The coding region in some flanking 5' and 3' UTR have been sequenced. The protein has a predicted molecular weight of 13,293; an isoelectric point of 5.73 and is 117 residues long.

Accordingly, since the subunits are vital to mRNA synthesis, their administration may be employed to up-regulate the expression of certain genes and to down-regulate others as needed. Administration may be via gene therapy. Abnormal cellular proliferation, e.g., cancer, may be treated with the subunits since lack of expression of these genes may lead to unregulated transcription.

The human interferon regulatory factor IRF3 gene shows strong homology to a group of transcription factors including IRF1 (Interferon Regulatory factor 1) and IRF2 (interferon Regulatory factor 2) which are important in mediating the transcriptional activation of interferon-alpha and -beta induced genes. It is possible that this gene also is important in mediating the transcriptional activation properties of interferon and that this factor may have some of the properties associated with interferon such as anti-viral activity. The human interferon regulatory factor IRF3 is potentially important in regulating the transcriptional activation of interferon-α and -β genes. IRF3 may also be important in mediating the transcriptional activation properties of interferon. The IRF3 polypeptide may be employed as an anti-viral agent. The administration of the IRF3 gene and its gene product may be employed to enhance the expression of interferon which has many medically important uses. The IRF3 gene was isolated from a human adult retina library.

The TM4SF gene may be employed as a target for the development of compounds to treat human T-cell leukemia virus type I since several monoclonal-antibodies inhibitory to syncytium formation targeted this TM4SF molecule.

The TM4SF gene may also be employed in the regulation of cell growth. This gene may also be employed as an immunogen or target to implement active and passive immunotherapy in patients with cancer. The gene encoding TM4SF was isolated from a human T-cell lymphoma library.

The TNFR-AF1, C1 gene and gene product may be employed to regulate B-lymphocyte proliferation, immunoglobulin class-switching and apoptosis. The TNFR-AF1 may also be employed to up-regulate the biological activity of TNF which is known to regress tumors. The gene encoding TNFR-AF1 C1 was isolated from an activated human nutrophil library.

The TM4SF, CD53 gene and gene product may be employed to regulate lymphoma cell growth and may also be employed to regulate cell growth. The gene encoding TM4SF (transmembrane 4 super family), CD53 was isolated from a human tumor pancreas library.

The retinoid X receptor γ may be employed to treat psoriasis and recalcitrincystic acne and cancer. This retinoid X receptor γ may also be employed to prevent a variety of pre-malignant lesions of skin and mucous membranes. The receptor may also be employed as a tumor suppressor. The receptor may also be employed to stimulate cell proliferation, differentiation and keratinization. The receptor may also be employed to treat X linked adrenal hypoplasia and hypogonatropic hypoglonatism. The gene encoding retinoid X receptor gamma was isolated from a human fetal lung III library.

The cytosolic resiniferatoxin binding protein (RBP-26) may be employed to reduce pain sensation due to its ability to selectively block mechanoheat nociceptors and warm receptors of the skin that are known to play a significant role in sensation of pain. The gene encoding RBP-26 was isolated from a human osteoclastoma stromal cell library.

The protein kinase C inhibitor protein has siginificant medical application uses such as inhibiting tumor cell growth and in regulating the many physiological functions that are mediated by the activation of protein kinase C. The gene encoding the protein kinase C inhibitor protein was isolated from a human corpus colosum library.

The polynucleotides and polypeptides of the present invention may be employed as research reagents and materials for discovery of treatments and diagnostics to human disease.

This invention provides a method for identification of the receptors for the polypeptides listed in Table 1. The gene encoding the receptor can be identified by numerous methods known to those of skill in the art, for example, ligand panning and FACS sorting (Coligan, et al., Current Protocols in Immun., 1(2), Chapter 5, (1991)). Preferably, expression cloning is employed wherein polyadenylated RNA is prepared from a cell responsive to the respective polypeptide, and a cDNA library created from this RNA is divided into pools and used to transfect COS cells or other cells that are not responsive to the proteins. Transfected cells which are grown on glass slides are exposed to labeled protein. The protein can be labeled by a variety of means including iodination or inclusion of a recognition site for a site-specific protein kinase. Following fixation and incubation, the slides are subjected to auto-radiographic analysis. Positive pools are identified and sub-pools are prepared and re-transfected using an iterative sub-pooling and re-screening process, eventually yielding a single clone that encodes the putative receptor.

As an alternative approach for receptor identification, labeled protein can be photoaffinity linked with cell membrane or extract preparations that express the receptor molecule. Cross-linked material is resolved by PAGE and exposed to X-ray film. The labeled complex containing the protein-receptor can be excised, resolved into peptide fragments, and subjected to protein microsequencing. The amino acid sequence obtained from microsequencing would be used to design a set of degenerate oligonucleotide probes to screen a cDNA library to identify the gene encoding the putative receptor.

This invention provides a method of screening compounds to identify those which enhance (agonists) or block (antagonists) interaction of protein to receptor. An agonist is a compound which increases the natural biological functions, while antagonists eliminate such functions. As an example, a mammalian cell or membrane preparation expressing the receptor would be incubated with labeled protein in the presence of the drug. The ability of the drug to enhance or block this interaction could then be measured.

Alternatively, the response of a known second messenger system following interaction of protein and receptor would be measured and compared in the presence or absence of the drug. Such second messenger systems include but are not limited to, cAMP guanylate cyclase, ion channels or phosphoinositide hydrolysis.

In the case where the polypeptides of the present invention are receptor polypeptides, the present invention also relates to methods for determining whether a ligand can bind to the receptor which comprises transfecting a cell population (one presumed not to contain a receptor) with the appropriate vector expressing the receptor, such that the cell will now express the receptor. A suitable response system is obtained by transfection of the DNA into a suitable host containing the desired second messenger pathways including cAMP, ion channels, psosphoinositide kinase, or calcium response. Such a transfection system provides a response system to analyze the activity of various ligands exposed to the cell. Ligands chosen could be identified through a rational approach by taking known ligands that interact with similar types of receptors or using small molecules, cell supernatants or extracts or natural products.

The present invention also relates to an assay for identifying potential antagonists. An example of such an assay combines the protein and a potential antagonist with membrane-bound receptors or recombinant receptors under appropriate conditions for a competitive inhibition assay. The protein can be labeled, such as by radio activity, such that the number of molecules bound to the receptor can determine the effectiveness of the potential antagonist.

The polypeptides listed in Table 1 of the present invention which have putatively been identified as receptors may be employed in a process for screening for antagonists and/or agonists for the receptor.

In general, such screening procedures involve providing appropriate cells which express the receptor on the surface thereof. In particular, a polynucleotide encoding the receptor of the present invention is employed to transfect cells to thereby express the receptor. Such transfection may be accomplished by procedures as hereinabove described.

One such screening procedure involves the use of melanophores which are transfected to express the receptor of the present invention. Such a screening technique is described in PCT WO 92/01810 published Feb. 6, 1992.

Thus, for example, such assay may be employed for screening for a receptor antagonist by contacting the melanophore cells which encode the receptor with both the receptor ligand and a compound to be screened. Inhibition of the signal generated by the ligand indicates that a compound is a potential antagonist for the receptor, i.e., inhibits activation of the receptor.

The screen may be employed for determining an agonist by contacting such cells with compounds to be screened and determining whether such compound generates a signal, i.e., activates the receptor.

Other screening techniques include the use of cells which express the receptor (for example, transfected CHO cells) in a system which measures extracellular pH changes caused by receptor activation, for example, as described in Science, volume 246, pages 181–296 (October 1989). For example, potential agonists or antagonists may be contacted with a cell which expresses the receptor and a second messenger response, e.g. signal transduction or pH changes, may be measured to determine whether the potential agonist or antagonist is effective.

Another such screening technique involves introducing RNA encoding the receptor into xenopus oocytes to transiently express the receptor. The receptor oocytes may then be contacted in the case of antagonist screening with the receptor ligand and a compound to be screened, followed by detection of inhibition of a calcium signal.

Another screening technique involves expressing the receptor in which the receptor is linked to a phospholipase C or D. As representative examples of such cells, there may be mentioned endothelial cells, smooth muscle cells, embryonic kidney cells, etc. The screening for an antagonist or agonist may be accomplished as hereinabove described by detecting activation of the receptor or inhibition of activation of the receptor from the phospholipase second signal.

Another method involves screening for antagonists by determining inhibition of binding of labeled ligand to cells which have the receptor on the surface thereof. Such a method involves transfecting a eukaryotic cell with DNA encoding the receptor such that the cell expresses the receptor on its surface and contacting the cell with a potential antagonist in the presence of a labeled form of a known ligand. The ligand can be labeled, e.g., by radioactivity. The amount of labeled ligand bound to the receptors is measured, e.g., by measuring radioactivity of the receptors. If the potential antagonist binds to the receptor as determined by a reduction of labeled ligand which binds to the receptors, the binding of labeled ligand to the receptor is inhibited.

The present invention also provides a method for determining whether a ligand not known to be capable of binding to a receptor can bind to such receptor which comprises contacting a mammalian cell which expresses a receptor with the ligand under conditions permitting binding of ligands to the receptor, detecting the presence of a ligand which binds to the receptor and thereby determining whether the ligand binds to the receptor. The systems hereinabove described for determining agonists and/or antagonists may also be employed for determining ligands which bind to the receptor.

In general, antagonists for receptors which are determined by screening procedures may be employed for a variety of therapeutic purposes. For example, such antagonists have been employed for treatment of hypertension, angina pectoris, myocardial infarction, ulcers, asthma, allergies, psychoses, depression, migraine, vomiting, and benign prostatic hypertrophy.

Agonists for receptors are also useful for therapeutic purposes, such as the treatment of asthma, Parkinson's disease, acute heart failure, hypotension, urinary retention, and osteoporosis.

Potential antagonists against the polypeptides of the present invention include an antibody, or in some cases, an oligopeptide, which binds to the polypeptide. Alternatively, a potential antagonist may be a closely related protein which binds to the receptors of the polypeptide, however, they are inactive forms of the polypeptide and thereby inhibit the action of the polypeptides.

Another potential antagonist is an antisense construct prepared using antisense technology. Antisense technology can be used to control gene expression through triple-helix formation or antisense DNA or RNA, both of which methods are based on binding of a polynucleotide to DNA or RNA. For example, the 5' coding portion of the polynucleotide sequence, which encodes for the mature polypeptides of the present invention, is used to design an antisense RNA oligonucleotide of from about 10 to 40 base pairs in length. A DNA oligonucleotide is designed to be complementary to a region of the gene involved in transcription (triple helix—see Lee et al., Nucl. Acids Res., 6:3073 (1979); Cooney et al, Science, 241:456 (1988); and Dervan et al., Science, 251: 1360 (1991)), thereby preventing transcription and the production of the polypeptide. The antisense RNA oligonucleotide hybridizes to the mRNA in vivo and blocks translation of the mRNA molecule into the polypeptide (Antisense—Okano, J. Neurochem., 56:560 (1991); Oligodeoxynucleotides as Antisense Inhibitors of Gene Expression, CRC Press, Boca Raton, Fla. (1988)). The oligonucleotides described above can also be delivered to cells such that the antisense RNA or DNA may be expressed in vivo to inhibit production of the protein.

Potential antagonists include a small molecule which binds to and occupies the active site of the polypeptide or to the receptor where the polypeptide of the present invention is a receptor, thereby making it inaccessible to substrate such that normal biological activity is prevented. Examples of small molecules include but are not limited to small peptides or peptide-like molecules.

Another potential antagonist includes a soluble form of the receptor polypeptides, e.g. a fragment of the receptor, which binds to the ligand and prevents the ligand from interacting with membrane bound receptors.

Antagonists to the human transcription regulator hADA2 may be employed to regulate the expression of Herpes simplex transactivator VP16, since hADA2 mediates its transcriptional activation properties. Many medically important genes may also be regulated by the antagonism of hADA2.

Antagonists to TATA related factor (TRF) may be employed to control general protein expression and for the regulation of the expression of specific important gene groups.

Antagonists to RNA polymerase subunits HRPB8, HRPB10 and HRPB11 may be employed to treat cancer since over expression of these subunits may lead to unregulated transcription.

Antagonists to interferon related factor-3 (IRF-3) may be employed to down regulate the overexpression of interferon with its adverse effects.

Antagonists to TM4SF may be employed to inhibit tumor growth.

Antagnoists to TNFR AF1, C1 may be employed to inhibit inflammation and apoptosis.

Antagnoists to TM4SF (transmembrane 4 super family) CD53 may be employed to inhibit certain leukemias.

Antagonists to the retinoid X receptor γ may be employed to treat psoriasis and inflammation. The antagonists may also be employed to prevent and/or treat hyperplasia and tumors in the lung, breast and other tissues.

Antagonists to protein kinase C inhibitor protein may be employed to inhibit the activation function of protein kinase C.

The antagonists may be employed therapeutically in a composition with a pharmaceutically acceptable carrier, e.g., as hereinafter described.

The polypeptides of the present invention and agonists and antagonists may be employed in combination with a suitable pharmaceutical carrier. Such compositions comprise a therapeutically effective amount of the polypeptide or agonist or antagonist, and a pharmaceutically acceptable carrier or excipient. Such a carrier includes but is not limited to saline, buffered saline, dextrose, water, glycerol, ethanol, and combinations thereof. The formulation should suit the mode of administration.

The invention also provides a pharmaceutical pack or kit comprising one or more containers filled with one or more of the ingredients of the pharmaceutical compositions of the invention. Associated with such container(s) can be a notice in the form prescribed by a governmental agency regulating the manufacture, use or sale of pharmaceuticals or biological products, which notice reflects approval by the agency of manufacture, use or sale for human administration. In addition, the polypeptides of the present invention or agonists or antagonists may be employed in conjunction with other therapeutic compounds.

The pharmaceutical compositions may be administered in a convenient manner such as by the oral, topical, intravenous, intraperitoneal, intramuscular, subcutaneous, intranasal or intradermal routes. The pharmaceutical compositions are administered in an amount which is effective for treating and/or prophylaxis of the specific indication. In general, they are administered in an amount of at least about 10 μg/kg body weight and in most cases they will be administered in an amount not in excess of about 8 mg/Kg body weight per day. In most cases, the dosage is from about 10 μg/kg to about 1 mg/kg body weight daily, taking into account the routes of administration, symptoms, etc.

The polypeptides and agonists and antagonists which are polypeptides may also be employed in accordance with the present invention by expression of such polypeptides in vivo, which is often referred to as "gene therapy."

Thus, for example, cells from a patient may be engineered with a polynucleotide (DNA or RNA) encoding a polypeptide ex vivo, with the engineered cells then being provided to a patient to be treated with the polypeptide. Such methods are well-known in the art and are apparent from the teachings herein. For example, cells may be engineered by the use of a retroviral plasmid vector containing RNA encoding a polypeptide of the present invention.

Similarly, cells may be engineered in vivo for expression of a polypeptide in vivo by, for example, procedures known in the art. For example, a packaging cell is transduced with a retroviral plasmid vector containing RNA encoding a polypeptide of the present invention such that the packaging cell now produces infectious viral particles containing the gene of interest. These producer cells may be administered to a patient for engineering cells in vivo and expression of the polypeptide in vivo. These and other methods for administering a polypeptide of the present invention by such method should be apparent to those skilled in the art from the teachings of the present invention.

Retroviruses from which the retroviral plasmid vectors hereinabove mentioned may be derived include, but are not limited to, Moloney Murine Leukemia Virus, spleen necrosis virus, retroviruses such as Rous Sarcoma Virus, Harvey Sarcoma Virus, avian leukosis virus, gibbon ape leukemia virus, human immunodeficiency virus, adenovirus, Myeloproliferative Sarcoma Virus, and mammary tumor virus. In one embodiment, the retroviral plasmid vector is derived from Moloney Murine Leukemia Virus.

The vector includes one or more promoters. Suitable promoters which may be employed include, but are not limited to, the retroviral LTR; the SV40 promoter; and the human cytomegalovirus (CMV) promoter described in Miller et al., *Biotechniques,* 7(9) :980–990 (1989), or any other promoter (e.g., cellular promoters such as eukaryotic cellular promoters including, but not limited to, the histone, pol III, and β-actin promoters). Other viral promoters which may be employed include, but are not limited to, adenovirus promoters, thymidine kinase (TK) promoters, and B19 parvovirus promoters. The selection of a suitable promoter will be apparent to those skilled in the art from the teachings contained herein.

The nucleic acid sequence encoding the polypeptide of the present invention is under the control of a suitable promoter. Suitable promoters which may be employed include, but are not limited to, adenoviral promoters, such as the adenoviral major late promoter; or heterologous promoters, such as the cytomegalovirus (CMV) promoter; the respiratory syncytial virus (RSV) promoter; inducible promoters, such as the MMT promoter, the metallothionein promoter; heat shock promoters; the albumin promoter; the ApoAI promoter; human globin promoters; viral thymidine kinase promoters, such as the Herpes Simplex thymidine kinase promoter; retroviral LTRs (including the modified retroviral LTRs hereinabove described); the β-actin promoter; and human growth hormone promoters. The promoter also may be the native promoter which controls the gene encoding the polypeptide.

The retroviral plasmid vector is employed to transduce packaging cell lines to form producer cell lines. Examples of packaging cells which may be transfected include, but are not limited to, the PES01, PA317, ψ-2, ψ-AM, PA12, T19-14X, VT-19-17-H2, ψCRE, ψCRIP, GP+E-86, GP+envAm12, and DAN cell lines as described in Miller, *Human Gene Therapy,* 1:5–14 (1990), which is incorporated herein by reference in its entirety. The vector may transduce the packaging cells through any means known in the art. Such means include, but are not limited to, electroporation, the use of liposomes, and CaPO$_4$ precipitation. In one alternative, the retroviral plasmid vector may be encapsulated into a liposome, or coupled to a lipid, and then administered to a host.

The producer cell line generates infectious retroviral vector particles which include the nucleic acid sequence(s) encoding the polypeptides. Such retroviral vector particles then may be employed, to transduce eukaryotic cells, either in vitro or in vivo. The transduced eukaryotic cells will express the nucleic acid sequence(s) encoding the polypeptide. Eukaryotic cells which may be transduced include, but are not limited to, embryonic stem cells, embryonic carcinoma cells, as well as hematopoietic stem cells, hepatocytes, fibroblasts, myoblasts, keratinocytes, endothelial cells, and bronchial epithelial cells.

This invention is also related to the use of the DNA (RNA) sequences diagnostically. Detection of a mutated form of sequences will allow a diagnosis of a disease or a susceptibility to a disease which results from underexpression of the protein.

Individuals carrying mutations in a human gene of the present invention may be detected at the DNA level by a variety of techniques. Nucleic acids for diagnosis may be obtained from a patient's cells, such as from blood, urine, saliva, tissue biopsy and autopsy material. The genomic DNA may be used directly for detection or may be amplified enzymatically by using PCR (Saiki et al., Nature, 324:163–166 (1986)) prior to analysis. RNA or cDNA may also be used for the same purpose. As an example, PCR primers complementary to the nucleic acid encoding the protein can be used to identify and analyze mutations. For example, deletions and insertions can be detected by a change in size of the amplified product in comparison to the normal genotype. Point mutations can be identified by hybridizing amplified DNA to radiolabeled RNA or alternatively, radiolabeled antisense DNA sequences. Perfectly matched sequences can be distinguished from mismatched duplexes by RNase A digestion or by differences in melting temperatures.

Sequence differences between the reference gene and genes having mutations may be revealed by the direct DNA sequencing method. In addition, cloned DNA segments may be employed as probes to detect specific DNA segments. The sensitivity of this method is greatly enhanced when combined with PCR. For example, a sequencing primer is used with double-stranded PCR product or a single-stranded template molecule generated by a modified PCR. The sequence determination is performed by conventional procedures with radiolabeled nucleotide or by automatic sequencing procedures with fluorescent-tags.

Genetic testing based on DNA sequence differences may be achieved by detection of alteration in electrophoretic mobility of DNA fragments in gels with or without denaturing agents. Small sequence deletions and insertions can be visualized by high resolution gel electrophoresis. DNA fragments of different sequences may be distinguished on denaturing formamide gradient gels in which the mobilities of different DNA fragments are retarded in the gel at different positions according to their specific melting or partial melting temperatures (see, e.g., Myers et al., Science, 230:1242 (1985)).

Sequence changes at specific locations may also be revealed by nuclease protection assays, such as RNase and S1 protection or the chemical cleavage method (e.g., Cotton et al., PNAS, USA, 85:4397–4401 (1985)).

Thus, the detection of a specific DNA sequence may be achieved by methods such as hybridization, RNase protection, chemical cleavage, direct DNA sequencing or the use of restriction enzymes, (e.g., Restriction Fragment Length Polymorphisms (RFLP)) and Southern blotting of genomic DNA.

In addition to more conventional gel-electrophoresis and DNA sequencing, mutations can also be detected by in situ analysis.

The present invention also relates to a diagnostic assay for detecting altered levels of the polypeptides of the present invention and soluble form of the receptor polypeptides of the present invention, in various tissues since an overexpression of the proteins compared to normal control tissue samples can detect the presence of a disease. Assays used to detect levels of protein in a sample derived from a host are well-known to those of skill in the art and include radioimmunoassays, competitive-binding assays, Western Blot analysis and preferably an ELISA assay. An ELISA assay initially comprises preparing an antibody specific to the antigen, preferably a monoclonal antibody. In addition a reporter antibody is prepared against the monoclonal antibody. To the reporter antibody is attached a detectable reagent such as radioactivity, fluorescence or in this example a horseradish peroxidase enzyme. A sample is now removed from a host and incubated on a solid support, e.g. a polystyrene dish, that binds the proteins in the sample. Any free protein binding sites on the dish are then covered by incubating with a non-specific protein such as bovine serum albumin. Next, the monoclonal antibody is incubated in the dish during which time the monoclonal antibodies attach to any proteins attached to the polystyrene dish. All unbound monoclonal antibody is washed out with buffer. The reporter antibody linked to horseradish peroxidase is now placed in the dish resulting in binding of the reporter antibody to any monoclonal antibody bound to the protein of interest. Unattached reporter antibody is then washed out. Peroxidase substrates are then added to the dish and the amount of color developed in a given time period is a measurement of the amount of protein present in a given volume of patient sample when compared against a standard curve.

A competition assay may be employed wherein antibodies specific to the protein is attached to a solid support and labeled protein and a sample derived from the host are passed over the solid support and the amount of label detected attached to the solid support can be correlated to a quantity of the protein in the sample.

The sequences of the present invention are also valuable for chromosome identification. The sequence is specifically targeted to and can hybridize with a particular location on an individual human chromosome. Moreover, there is a current need for identifying particular sites on the chromosome. Few chromosome marking reagents based on actual sequence data (repeat polymorphisms) are presently available for marking chromosomal location. The mapping of DNAs to chromosomes according to the present invention is an important first step in correlating those sequences with genes associated with disease.

Briefly, sequences can be mapped to chromosomes by preparing PCR primers (preferably 15–25 bp) from the cDNA. Computer analysis of the 3' untranslated region of the gene is used to rapidly select primers that do not span more than one exon in the genomic DNA, thus complicating the amplification process. These primers are then used for PCR screening of somatic cell hybrids containing individual human chromosomes. Only those hybrids containing the human gene corresponding to the primer will yield an amplified fragment.

PCR mapping of somatic cell hybrids is a rapid procedure for assigning a particular DNA to a particular chromosome. Using the present invention with the same oligonucleotide primers, sublocalization can be achieved with panels of fragments from specific chromosomes or pools of large genomic clones in an analogous manner. Other mapping strategies that can similarly be used to map to its chromosome include in situ hybridization, prescreening with labeled flow-sorted chromosomes and preselection by hybridization to construct chromosome specific-cDNA libraries.

Fluorescence in situ hybridization (FISH) of a cDNA clone to a metaphase chromosomal spread can be used to provide a precise chromosomal location in one step. This technique can be used with cDNA having at least 50 or 60 bases. For a review of this technique, see Verma et al., Human Chromosomes: a Manual of Basic Techniques, Pergamon Press, New York (1988).

Once a sequence has been mapped to a precise chromosomal location, the physical position of the sequence on the chromosome can be correlated with genetic map data. Such data are found, for example, in V. McKusick, Mendelian Inheritance in Man (available on line through Johns Hopkins University Welch Medical Library). The relationship between genes and diseases that have been mapped to the same chromosomal region are then identified through linkage analysis (coinheritance of physically adjacent genes).

Next, it is necessary to determine the differences in the cDNA or genomic sequence between affected and unaffected individuals. If a mutation is observed in some or all of the affected individuals but not in any normal individuals, then the mutation is likely to be the causative agent of the disease.

With current resolution of physical mapping and genetic mapping techniques, a cDNA precisely localized to a chromosomal region associated with the disease could be one of between 50 and 500 potential causative genes. (This assumes 1 megabase mapping resolution and one gene per 20 kb).

The polypeptides, their fragments or other derivatives, or analogs thereof, or cells expressing them can be used as an immunogen to produce antibodies thereto. These antibodies can be, for example, polyclonal or monoclonal antibodies. The present invention also includes chimeric, single chain, and humanized antibodies, as well as Fab fragments, or the product of an Fab expression library. Various procedures known in the art may be used for the production of such antibodies and fragments.

Antibodies generated against the polypeptides corresponding to a sequence of the present invention can be obtained by direct injection of the polypeptides into an animal or by administering the polypeptides to an animal, preferably a nonhuman. The antibody so obtained will then bind the polypeptides itself. In this manner, even a sequence encoding only a fragment of the polypeptides can be used to generate antibodies binding the whole native polypeptides. Such antibodies can then be used to isolate the polypeptide from tissue expressing that polypeptide.

For preparation of monoclonal antibodies, any technique which provides antibodies produced by continuous cell line cultures can be used. Examples include the hybridoma technique (Kohler and Milstein, Nature, 256:495–497, 1975), the trioma technique, the human B-cell hybridoma technique (Kozbor et al., Immunology Today 4:72, 1983), and the EBV-hybridoma technique to produce human monoclonal antibodies (Cole et al., 1985, in Monoclonal Antibodies and Cancer Therapy, Alan R. Liss, Inc., pp. 77–96).

Techniques described for the production of single chain antibodies (U.S. Pat. No. 4,946,778) can be adapted to produce single chain antibodies to immunogenic polypeptide products of this invention. Also, transgenic mice may be used to express humanized antibodies to immunogenic polypeptide products of this invention.

The present invention will be further described with reference to the following examples; however, it is to be understood that the present invention is not limited to such examples. All parts or amounts, unless otherwise specified, are by weight.

In order to facilitate understanding of the following examples certain frequently occurring methods and/or terms will be described.

"Plasmids" are designated by a lower case p preceded and/or followed by capital letters and/or numbers. The starting plasmids herein are either commercially available, publicly available on an unrestricted bases, or can be constructed from available plasmids in accord with published procedures. In addition, equivalent plasmids to those described are known in the art and will be apparent to the ordinarily skilled artisan.

"Digestion" of DNA refers to catalytic cleavage of the DNA with a restriction enzyme that acts only at certain sequences in the DNA. The various restriction enzymes used herein are commercially available and their reaction conditions, cofactors and other requirements were used as would be known to the ordinarily skilled artisan. For analytical purposes, typically 1 µg of plasmid or DNA fragment is used with about 2 units of enzyme in about 20 µl of buffer solution. For the purpose of isolating DNA fragments for plasmid construction, typically 5 to 50 µg of DNA are digested with 20 to 250 units of enzyme in a larger volume. Appropriate buffers and substrate amounts for particular restriction enzymes are specified by the manufacturer. Incubation times of about 1 hour at 37° C. are ordinarily used, but may vary in accordance with the supplier's instructions. After digestion the reaction is electrophoresed directly on a polyacrylamide gel to isolate the desired fragment.

Size separation of the cleaved fragments is performed using 8 percent polyacrylamide gel described by Goeddel, D. et al., Nucleic Acids Res., 8:4057 (1980).

"Oligonucleotides" refers to either a single stranded polydeoxynucleotide or two complementary polydeoxynucleotide strands which may be chemically synthesized. Such synthetic oligonucleotides have no 5' phosphate and thus will not ligate to another oligonucleotide without adding a phosphate with an ATP in the presence of a kinase. A synthetic oligonucleotide will ligate to a fragment that has not been dephosphorylated.

"Ligation" refers to the process of forming phosphodiester bonds between two double stranded nucleic acid fragments (Maniatis, T., et al., Id., p. 146). Unless otherwise provided, ligation may be accomplished using known buffers and conditions with 10 units of T4 DNA ligase ("ligase") per 0.5 µg of approximately equimolar amounts of the DNA fragments to be ligated.

Unless otherwise stated, transformation was performed as described in the method of Graham, F. and Van der Eb, A., Virology, 52:456–457 (1973).

EXAMPLE 1

Bacterial Expression and Purification of the Proteins

The DNA sequence encoding any of the proteins, is initially amplified using PCR oligonucleotide primers corresponding to the 5' sequences of the processed protein (minus the signal peptide sequence) and the vector sequences 3' to the gene. Additional nucleotides corresponding to the DNA sequence are added to the 5' and 3' sequences respectively. The 5' oligonucleotide primer may contain, for example, a restriction enzyme site followed by nucleotides of coding sequence starting from the presumed terminal amino acid of the processed protein. The 3' sequence may, for example, contain complementary sequences to a restriction enzyme site and also be followed by nucleotides of the nucleic acid sequence encoding the protein of interest. The restriction enzyme sites correspond to the restriction enzyme sites on a bacterial expression vector, for example, pQE-9 (Qiagen, Inc. Chatsworth, Calif.). pQE-9 encodes antibiotic resistance ($Amp^r$), a bacterial origin of replication (ori), an IPTG-regulatable promoter operator (P/O), a ribosome binding site (RBS), a 6-His tag and restriction enzyme sites. pQE-9 is then digested with the restriction enzymes corresponding to restriction enzyme sites contained in he primer sequences. The amplified sequences are ligated into pQE-9 and inserted in frame with the sequence encoding for the histidine tag and the RBS. The ligation mixture is then used to transform an *E. coli* strain, for example, M15/rep 4 (Qiagen) by the procedure described in Sambrook et al., Molecular Cloning: A Laboratory Manual, Cold Spring Laboratory Press, (1989). M15/rep4 contains multiple copies of the plasmid pREP4, which expresses the lacI repressor and also confers kanamycin resistance ($Kan^r$). Transformants are identified by their ability to grow on LB plates and ampicillin/kanamycin resistant colonies are selected. Plasmid DNA is isolated and confirmed by restriction analysis. Clones containing the desired constructs are grown overnight (O/N) in liquid culture in LB media supplemented with both Amp (100 ug/ml) and Kan (25 ug/ml). The O/N culture is used to inoculate a large culture at a ratio of 1:100 to 1:250. The cells are grown to an optical density 600 ($O.D.^{600}$) of between 0.4 and 0.6. IPTG ("Isopropyl-B-D-thiogalacto pyranoside") is then added to a final concentration of 1 mM. IPTG induces by inactivating the lacI repressor, clearing the P/O leading to increased gene expression. Cells are grown an extra 3 to 4 hours. Cells are then harvested by centrifugation. The cell pellet is solubilized in the chaotropic agent 6 Molar Guanidine HCl. After clarification, solubilized protein is purified from this solution by chromatography on a Nickel-Chelate column under conditions that allow for tight binding by proteins containing the 6-His tag (Hochuli, E. et al., J. Chromatography 411:177–184 (1984)). The protein is eluted from the column in 6 molar guanidine HCl pH 5.0 and for the purpose of renaturation adjusted to 3 molar guanidine HCl, 100 mM sodium phosphate, 10 mmolar glutathione (reduced) and 2 mmolar glutathione (oxidized). After incubation in this solution for 12 hours the protein is dialyzed to 10 mmolar sodium phosphate.

EXAMPLE 2

Cloning and Expression of the Proteins Using the Baculovirus Expression System The DNA sequence encoding one of the full length proteins, is amplified using PCR oligonucleotide primers corresponding to the 5' and 3' sequences of the gene.

The 5' primer may contain a restriction enzyme site and be followed by a number of nucleotides resembling an efficient signal for the initiation of translation in eukaryotic cells (Kozak, *J. Mol. Biol.,* 196:947–950 (1987) which is just behind the first few nucleotides of the gene of interest.

The 3' primer may also contain a restriction endonuclease and have extra nucleotides which are complementary to the 3' non-translated sequence of the gene. The amplified sequences are isolated from a 16 agarose gel using a commercially available kit ("Geneclean," BIO 101 Inc., La Jolla, Calif.). The fragment is then digested with the endonucleases and purified again on a 1% agarose gel. This fragment is designated F2.

A vector, for example, pA2 or pRG1 (modification of pVL941 vector, discussed below) may be used for the expression of the protein using the baculovirus expression system (for review see: Summers, M. D. and Smith, G. E. 1987, A manual of methods for baculovirus vectors and insect cell culture procedures, Texas Agricultural Experimental Station Bulletin No. 1555). These vectors contain the strong polyhedrin promoter of the *Autographa californica* nuclear polyhedrosis virus (AcMNPV) followed by the recognition sites for the respective restriction endonucleases. The polyadenylation site of the simian virus (SV)40 is used for efficient polyadenylation. For an easy selection of recombinant virus the beta-galactosidase gene from *E.coli* is inserted in the same orientation as the polyhedrin promoter followed by the polyadenylation signal of the polyhedrin gene. The polyhedrin sequences are flanked at both sides by viral sequences for the cell-mediated homologous recombination of co-transfected wild-type viral DNA. Many other baculovirus vectors could be used in place of pRG1 such as pAc373, pVL941 and pAcIM1 (Luckow, V. A. and Summers, M. D., *Virology,* 170:31–39).

The plasmid is digested with the restriction enzymes and dephosphorylated using calf intestinal phosphatase by procedures known in the art. The DNA is then isolated from a 1% agarose gel using the commercially available kit ("Geneclean" BIO 101 Inc., La Jolla, Calif.). This vector DNA is designated V2.

Fragment F2 and the dephosphorylated plasmid V2 are ligated with T4 DNA ligase. An E.coli strain, for example, HB101 cells are then transformed and bacteria which contain the recombinant plasmid are identified using the restriction enzymes. The sequence of the cloned fragment is confirmed by DNA sequencing.

5 $\mu$g of the plasmid is co-transfected with 1.0 $\mu$g of a commercially available linearized baculovirus ("BaculoGold™ baculovirus DNA", Pharmingen, San Diego, Calif.) using the lipofection method (Felgner et al. Proc. Natl. Acad. Sci. USA, 84:7413–7417 (1987)).

1 $\mu$g of BaculoGold™ virus DNA and 5 $\mu$g of the plasmid are mixed in a sterile well of a microtiter plate containing 50 $\mu$l of serum free Grace's medium (Life Technologies Inc., Gaithersburg, Md.). Afterwards 10 $\mu$l Lipofectin plus 90 $\mu$l Grace's medium are added, mixed and incubated for 15 minutes at room temperature. Then the transfection mixture is added drop-wise to the Sf9 insect cells (ATCC CRL 1711) seeded in a 35 mm tissue culture plate with 1 ml Grace's medium without serum. The plate is rocked back and forth to mix the newly added solution. The plate was then incubated for 5 hours at 27° C. After 5 hours the transfection solution is removed from the plate and 1 ml of Grace's insect medium supplemented with 10% fetal calf serum is added. The plate is put back into an incubator and cultivation continued at 27° C. for four days.

After four days the supernatant is collected and a plaque assay performed similar as described by Summers and Smith (supra). As a modification an agarose gel with "Blue Gal" (Life Technologies Inc., Gaithersburg) is used which allows an easy isolation of blue stained plaques. (A detailed description of a "plaque assay" can also be found in the user's guide for insect cell culture and baculovirology distributed by Life Technologies Inc., Gaithersburg, page 9–10).

Four days after the serial dilution the virus is added to the cells and blue stained plaques are picked with the tip of an Eppendorf pipette. The agar containing the recombinant viruses is then resuspended in an Eppendorf tube containing 200 $\mu$l of Grace's medium. The agar is removed by a brief centrifugation and the supernatant containing the recombinant baculovirus is used to infect Sf9 cells seeded in 35 mm dishes. Four days later the supernatants of these culture dishes are harvested and then stored at 4° C.

Sf9 cells are grown in Grace's medium supplemented with 10% heat-inactivated FBS. The cells are infected with the recombinant baculovirus at a multiplicity of infection (MOI) of 2. Six hours later the medium is removed and replaced with SF900 II medium minus methionine and cysteine (Life Technologies Inc., Gaithersburg). 42 hours later 5 μCi of $^{35}$S-methionine and 5 μCi $^{35}$S cysteine (Amersham) are added. The cells are further incubated for 16 hours before they are harvested by centrifugation and the labelled proteins visualized by SDS-PAGE and autoradiography.

EXAMPLE 3

Expression of Recombinant Protein in COS Cells

The expression of plasmid, protein-HA is derived from a vector pcDNAI/Amp (Invitrogen) containing: 1) SV40 origin of replication, 2) ampicillin resistance gene, 3) *E.coli* replication origin, 4) CMV promoter followed by a polylinker region, an SV40 intron and polyadenylation site. A DNA fragment encoding the entire precursor and a HA tag fused in frame to its 3' end is cloned into the polylinker region of the vector, therefore, the recombinant protein expression is directed under the CMV promoter. The HA tag corresponds to an epitope derived from the influenza hemagglutinin protein as previously described (I. Wilson, H. Niman, R. Heighten, A Cherenson, Connolly, and Lerner, *Cell* 37:767, (1984)). The infusion of HA tag to the target protein allows easy detection of the recombinant protein with an antibody that recognizes the HA epitope.

The DNA sequence encoding the protein is constructed by PCR using two primers, a 5' primer containing a restriction enzyme site followed by a number of nucleotides of the coding sequence starting from the initiation codon, and a 3' primer also containing complementary sequences to a restriction site, translation stop codon, HA tag and the last few nucleotides of the coding sequence (not including the stop codon). Therefore, the PCR product contains restriction enzyme sites, coding sequence followed by HA tag fused in frame, a translation termination stop codon next to the HA tag, and the other restriction enzyme site. The PCR amplified DNA fragment and the vector, pcDNAI/Amp, are digested with appropriate restriction enzymes and ligated. The ligation mixture is transformed into an *E. coli* strain, for example, SURE (Stratagene Cloning Systems, La Jolla, Calif.) and the transformed culture is plated on ampicillin media plates and resistant colonies are selected. Plasmid DNA is isolated from transformants and examined by restriction analysis for the presence of the correct fragment. For expression of the recombinant protein, COS cells are transfected with the expression vector by DEAE-DEXTRAN method (J. Sambrook, E. Fritsch, T. Maniatis, Molecular Cloning: A Laboratory Manual, Cold Spring Laboratory Press, (1989)). The expression of the HA protein is detected by radiolabelling and immunoprecipitation method (E. Harlow, D. Lane, Antibodies: A Laboratory Manual, Cold Spring Harbor Laboratory Press, (1988)). Cells are labelled for 8 hours with $^{35}$S-cysteine two days post transfection. Culture media is then collected and cells are lysed with detergent (RIPA buffer (150 mM NaCl, 1% NP-40, 0.1% SDS, 1% NP-40, 0.5% DOC, 50 mM Tris, pH 7.5) (Wilson, I. et al., Id. 37:767 (1984)). Both cell lysate and culture media are precipitated with an HA specific monoclonal antibody. Proteins precipitated are analyzed on 15% SDS-PAGE gels.

EXAMPLE 4

Isolation of A Selected Clone From the Deposited cDNA Library

Two approaches are used to isolate a particular gene out of the deposited cDNA library.

In the first, a clone is isolated directly by screening the library using an oligonucleotide probe. To isolate a particular gene, a specific oligonucleotide with 30–40 nucleotides is synthesized using an Applied Biosystems DNA synthesizer according to a fragment of the gene sequence. The oligonucleotide is labeled with $^{32}$p-ATP using T4 polynucleotide kinase and purified according to the standard protocol (Maniatis et al., Molecular Cloning: A Laboratory Manual, Cold Spring Harbor Press, Cold Spring, NY, 1982). The Lambda cDNA library deposited is plated on 1.5% agar plate to the density of 20,000–50,000 pfu/150 mm plate. These plates are screened using Nylon membranes according to the standard phage screening protocol (Stratagene, 1993). Specifically, the Nylon membrane with denatured and fixed phage DNA is prehybridized in 6×SSC, 20 mM NaH$_2$PO$_4$, 0.4% SDS, 5×Denhardt's 500 μg/ml denatured, sonicated salmon sperm DNA; and 6×SSC, 0.1% SDS. After one hour of prehybridization, the membrane is hybridized with hybridization buffer 6×SSC, 20 mM NaH$_2$PO$_4$, 0.4% SDS, 500 ug/ml denatured, sonicated salmon sperm DNA with 1×10$^6$ cpm/ml $^{32}$P-probe overnight at 42° C. The membrane is washed at 45–50° C. with washing buffer 6×SSC, 0.1% SDS for 20–30 minutes dried and exposed to Kodak X-ray film overnight. Positive clones are isolated and purified by secondary and tertiary screening. The purified clone is sequenced to verify its identity to the fragment sequence.

An alternative approach to screen the deposited cDNA library is to prepare a DNA probe corresponding to the entire sequence. To prepare a probe, two oligonucleotide primers of 17–20 nucleotides derived from both ends of the sequence are synthesized and purified. These two oligonucleotide are used to amplify the probe using the cDNA library template. The DNA template is prepared from the phage lysate of the deposited cDNA library according to the standard phage DNA preparation protocol (Maniatis et al.). The polymerase chain reaction is carried out in 25 μl of reaction mixture with 0.5 ug of the above cDNA template. The reaction mixture is 1.5–5 mM MgCl$_2$, 0.01% (w/v) gelatin, 20 μM each of dATP, dCTP, dGTP, dTTP, 25 pmol of each primer and 0.25 Unit of Taq polymerase. Thirty five cycles of PCR (denaturation at 94° C. for 1 min; annealing at 55° C. for 1 min; elongation at 72° C. for 1 min) are performed with the Perkin-Elmer Cetus automated thermal cycler. The amplified product is analyzed by agarose gel electrophoresis and the DNA band with expected molecular weight is excised and purified. The PCR product is verified to be the probe by subcloning and sequencing the DNA product. The probe is labeled with the Multiprime DNA Labelling System (Amersham) at a specific activity <1×10$^9$ dpm/μg. This probe is used to screen the deposited lambda cDNA library according to Stratagene's protocol. Hybridization is carried out with 5×TEN (20×TEN:0.3M Tris-HCl pH 8.0, 0.02M EDTA and 3M NaCl), 5× Denhardts, 0.5% sodium pyrophosphate, 0.1% SDS, 0.2mg/ml heat denatured salmon sperm DNA and 1×10$^6$ cpm/ml of [$^{32}$p]-labeled probe at 55° C. for 12 hours. The filters are washed in 0.5×TEN at room temperature for 20–30 min., then at 55° C. for 15 min. The filters are dried and autoradiographed at −70° C. using Kodak XAR-5 film. The positive clones are purified by secondary and tertiary screening. The sequence of the isolated clone are verified by DNA sequencing.

General procedures for obtaining complete sequences from probes are summarized as follows:
Procedure Selected human DNA from a probe corresponding to part of the human gene is purified e.g., by endonuclease digestion using EcoR1, gel electrophoresis, and isolation of the probe sequence by removal from low melting agarose gel. The isolated insert DNA, is radiolabeled e.g., with 32p labels, preferably by nick translation or random primer labeling. The labeled probe insert is used as a probe to screen a lambda phage cDNA library or a plasmid cDNA library. Colonies containing genes related to the probe cDNA are identified and purified by known purification methods. The ends of the newly purified genes are nucleotide sequenced to identify full length sequences. Complete sequencing of full length genes is then performed by Exonuclease III digestion or primer walking. Northern blots of the mRNA from various tissues using at least part of the EST clone as a probe can optionally be performed to check the size of the mRNA against that of the purported full length cDNA.

EXAMPLE 5

Expression via Gene Therapy

Fibroblasts are obtained from a subject by skin biopsy. The resulting tissue is placed in tissue-culture medium and separated into small pieces. Small chunks of the tissue are placed on a wet surface of a tissue culture flask, approximately ten pieces are placed in each flask. The flask is turned upside down, closed tight and left at room temperature over night. After 24 hours at room temperature, the flask is inverted and the chunks of tissue remain fixed to the bottom of the flask and fresh media (e.g., Ham's F12 media, with 10% FBS, penicillin and streptomycin, is added. This is then incubated at 37° C. for approximately one week. At this time, fresh media is added and subsequently changed every several days. After an additional two weeks in culture, a monolayer of fibroblasts emerge. The monolayer is trypsinized and scaled into larger flasks.

pMV-7 (Kirschmeier et al, *DNA*, 7:219–25 (1988) flanked by the long terminal repeats of the Moloney murine sarcoma virus, is digested with-EcoRI and HindIII and subsequently treated with calf intestinal phosphatase. The linear vector is fractionated on agarose gel and purified, using glass beads.

The cDNA encoding a polypeptide of the present invention is amplified using PCR primers which correspond to the 5' and 3' end sequences respectively. The S' primer containing an EcoRI site and the 3' primer further includes a HindIII site. Equal quantities of the Moloney murine sarcoma virus linear backbone and the amplified EcoRI and HindIII fragment are added together, in the presence of T4 DNA ligase. The resulting mixture is maintained under conditions appropriate for ligation of the two fragments. The ligation mixture is used to transform bacteria HB101, which are then plated onto agar-containing kanamycin for the purpose of confirming that the vector had the gene of interest properly inserted.

The amphotropic pA317 or GP+am12 packaging cells are grown in tissue culture to confluent density in Dulbecco's Modified Eagle's Medium (DMEM) with 10% calf serum (CS), penicillin and streptomycin. The MSV vector containing the gene is then added to the media and the packaging cells are transduced with the vector. The packaging cells now produce infectious viral particles containing the gene (the packaging cells are now referred to as producer cells).

Fresh media is added to the transduced producer cells, and subsequently, the media is harvested from a 10 cm plate of confluent producer cells. The spent media, containing the infectious viral particles, is filtered through a millipore filter to remove detached producer cells and this media is then used to infect fibroblast cells. Media is removed from a sub-confluent plate of fibroblasts and quickly replaced with the media from the producer cells. This media is removed and replaced with fresh media. If the titer of virus is high, then virtually all fibroblasts will be infected and no selection is required. If the titer is very low, then it is necessary to use a retroviral vector that has a selectable marker, such as neo or his.

The engineered fibroblasts are then injected into the host, either alone or after having been grown to confluence on cytodex 3 microcarrier beads. The fibroblasts now produce the protein product.

Numerous modifications and variations of the present invention are possible in light of the above teachings and, therefore, within the scope of the appended claims, the invention may be practiced otherwise than as particularly described.

TABLE 1

| CLONE NO. | PUTATIVE IDENTIFICATION | SEQ ID No. |
|---|---|---|
| HBGBA67 | amyloid-like protein present in breast | 1 |
| HE2CB95 | hADA2 | 2 |
| HTEAZ96 | TRF | 3 |
| HPTIK55 | hRPB11 | 4 |
| HARA063 | IRF3 | 5 |
| HLTAH80 | TM4SF | 6 |
| HNFBT92 | TNFR AF1, C1 | 7 |
| HTPBA27 | TM4SF, CD53 | 8 |
| HLHAR55 | Retinoid X Receptor | 9 |
| HSRDG78 | RBP-26 | 10 |
| HCCAA03 | Protein kinase C inhibitor protein | 11 |

TABLE 2

| CLONE NO. | PUTATIVE IDENTIFICATION | SEQ ID No. |
|---|---|---|
| HBGBA67 | amyloid-like protein present in breast | 12 |
| HE2CB95 | hADA2 | 13 |
| HTEAZ96 | TRF | 14 |
| HPTIK55 | hRPB11 | 15 |
| HARA063 | IRF3 | 16 |
| HLTAH80 | TM4SF | 17 |
| HNFBT92 | TNFR AF1, C1 | 18 |
| HTPBA27 | TM4SF, CD53 | 19 |
| HLHAR55 | Retinoid X Receptor | 20 |
| HSRDG78 | RBP-26 | 21 |
| HCCAA03 | Protein kinase C inhibitor protein | 22 |

I claim:

1. An isolated polynucleotide consisting of a nucleic acid sequence selected from the group consisting of:
   (a) a polynucleotide encoding amino acids 2–443 of SEQ ID NO:13;
   (b) a polynucleotide encoding amino acids 1–443 of SEQ ID NO:13;
   (c) a polynucleotide encoding the amino acid sequence encoded by the cDNA contained in ATCC Deposit No. 97242;
   (d) a polynucleotide encoding at least 30 contiguous amino acids of SEQ ID NO:13 or the cDNA clone contained in ATCC Deposit No. 97242;
   (e) a polynucleotide encoding at least 50 contiguous amino acids of SEQ ID NO:13 or the cDNA clone contained in ATCC Deposit No. 97242;
   (f) a polynucleotide of at least 30 contiguous nucleotides of SEQ ID NO:2 or the coding strand of the cDNA clone contained in ATCC Deposit No. 97242;
   (g) a polynucleotide of at least 40 contiguous nucleotides of SEQ ID NO:2 or the coding strand of the cDNA clone contained in ATCC Deposit No. 97242;
   (h) a polynucleotide of at least 50 contiguous nucleotides of SEQ ID NO:2 or the coding strand of the cDNA clone contained in ATCC Deposit No. 97242;
   (i) a polynucleotide of at least 60 contiguous nucleotides of SEQ ID NO:2 or the coding strand of the cDNA clone contained in ATCC Deposit No. 97242; and
   (j) the complement of (a), (b), (c), (d), (e), (f), (g), (h), or (i).

2. The isolated polynucleotide of claim 1, wherein said polynucleotide is (a).

3. The isolated polynucleotide of claim 2, which comprises nucleotides 124 to 1449 of SEQ ID NO:2.

4. The isolated polynucleotide of claim 1, wherein said polynucleotide is (b).

5. The isolated polynucleotide of claim 4, which comprises nucleotides 121 to 1449 of SEQ ID NO:2.

6. The isolated polynucleotide of claim 1 fused to a heterologous polynucleotide.

7. The isolated polynucleotide of claim 6, wherein the heterologous polynucleotide encodes for a heterologous polypeptide.

8. The isolated polynucleotide of claim 1, wherein the polynucleotide is double stranded.

9. A recombinant vector comprising the polynucleotide of claim 1.

10. A recombinant host comprising the polynucleotide of claim 1.

11. An isolated polynucleotide that hybridizes to SEQ ID NO:2 or the cDNA clone contained in ATCC Deposit No. 97272, wherein said hybridization takes place under hybridization conditions comprising hybridization in a buffer consisting of 5×TEN, 5×Denhardts, 0.5% Denhardts, 0.5% sodium pyrophosphate, 0.1% SDS, and 0.2 mg/ml heat denatured salmon sperm DNA for 12 hours at 55° C., and wash in a buffer consisting of 0.5×TEN for 15 minutes at 55° C.

12. An isolated polynucleotide comprising a nucleic acid sequence selected from the group consisting of:

(a) a polynucleotide encoding amino acids 2–443 of SEQ ID NO:13;

(b) a polynucleotide encoding amino acids 1–443 of SEQ ID NO:13;

(c) a polynucleotide encoding the amino acid sequence encoded by the cDNA contained in ATCC Deposit No. 97242;

(d) a polynucleotide encoding at least 30 contiguous amino acids of SEQ ID NO:13 or the cDNA clone contained in ATCC Deposit No. 97242;

(e) a polynucleotide encoding at least 50 contiguous amino acids of SEQ ID NO:13 or the cDNA clone contained in ATCC Deposit No. 97242;

(f) a polynucleotide of at least 30 contiguous nucleotides of SEQ ID NO:2 or the coding strand of the cDNA clone contained in ATCC Deposit No. 97242;

(g) a polynucleotide of at least 40 contiguous nucleotides of SEQ ID NO:2 or the coding strand of the cDNA clone contained in ATCC Deposit No. 97242;

(h) a polynucleotide of at least 50 contiguous nucleotides of SEQ ID NO:2 or the coding strand of the cDNA clone contained in ATCC Deposit No. 97242;

(i) a polynucleotide of at least 60 contiguous nucleotides of SEQ ID NO:2 or the coding strand of the cDNA clone contained in ATCC Deposit No. 97242; and (j) the complement of (a), (b), (c), (d), (e), (f), (g), (h), or (i).

13. The isolated polynucleotide of claim 12, wherein said polynucleotide is (a).

14. The isolated polynucleotide of claim 13, which comprises nucleotides 124 to 1449 of SEQ ID NO:2.

15. The isolated polynucleotide of claim 12, wherein said polynucleotide is (b).

16. The isolated polynucleotide of claim 15, which comprises nucleotides 121 to 1449 of SEQ ID NO:2.

17. The isolated polynucleotide of claim 12 fused to a heterologous polynucleotide.

18. The isolated polynucleotide of claim 17, wherein the heterologous polynucleotide encodes for a heterologous polypeptide.

19. The isolated polynucleotide of claim 12, wherein the polynucleotide is double stranded.

20. The isolated polynucleotide of claim 12, wherein said polynucleotide is (c).

21. The isolated polynucleotide of claim 12, wherein said polynucleotide is (d).

22. The isolated polynucleotide of claim 12, wherein said polynucleotide is (e).

23. The isolated polynucleotide of claim 12, wherein said polynucleotide is (f).

24. The isolated polynucleotide of claim 12, wherein said polynucleotide is (g).

25. The isolated polynucleotide of claim 12, wherein said polynucleotide is (h).

26. The isolated polynucleotide of claim 12, wherein said polynucleotide is (i).

27. The isolated polynucleotide of claim 12, wherein said polynucleotide is (j).

28. A vector comprising the polynucleotide of claim 13.

29. A vector comprising the polynucleotide of claim 15.

30. A vector comprising the polynucleotide of claim 20.

31. A vector comprising the polynucleotide of claim 21.

32. A vector comprising the polynucleotide of claim 22.

33. A vector comprising the polynucleotide of claim 23.

34. A vector comprising the polynucleotide of claim 24.

35. A vector comprising the polynucleotide of claim 25.

36. A vector comprising the polynucleotide of claim 26.

37. A vector comprising the polynucleotide of claim 27.

38. A host cell comprising the polynucleotide of claim 13, wherein said polynucleotide is operatively associated with a heterologous regulatory sequence.

39. A host cell comprising the polynucleotide of claim 15, wherein said polynucleotide is operatively associated with a heterologous regulatory sequence.

40. A host cell comprising the polynucleotide of claim 20, wherein said polynucleotide is operatively associated with a heterologous regulatory sequence.

41. A host cell comprising the polynucleotide of claim 21, wherein said polynucleotide is operatively associated with a heterologous regulatory sequence.

42. A host cell comprising the polynucleotide of claim 22, wherein said polynucleotide is operatively associated with a heterologous regulatory sequence.

43. A host cell comprising the polynucleotide of claim 23, wherein said polynucleotide is operatively associated with a heterologous regulatory sequence.

44. A host cell comprising the polynucleotide of claim 24, wherein said polynucleotide is operatively associated with a heterologous regulatory sequence.

45. A host cell comprising the polynucleotide of claim 25, wherein said polynucleotide is operatively associated with a heterologous regulatory sequence.

46. A host cell comprising the polynucleotide of claim 26, wherein said polynucleotide is operatively associated with a heterologous regulatory sequence.

47. A host cell comprising the polynucleotide of claim 27, wherein said polynucleotide is operatively associated with a heterologous regulatory sequence.

48. A method of producing a protein comprising: (a) culturing the host cell of claim 38 under conditions such that said protein is expressed; and (b) recovering said protein.

49. A method of producing a protein comprising: (a) culturing the host cell of claim 39 under conditions such that said protein is expressed; and (b) recovering said protein.

50. A method of producing a protein comprising: (a) culturing the host cell of claim 40 under conditions such that said protein is expressed; and (b) recovering said protein.

51. A method of producing a protein comprising: (a) culturing the host cell of claim 41 under conditions such that said protein is expressed; and (b) recovering said protein.

52. A method of producing a protein comprising: (a) culturing the host cell of claim 42 under conditions such that said protein is expressed; and (b) recovering said protein.

53. A method of producing a protein comprising: (a) culturing the host cell of claim 43 under conditions such that said protein is expressed; and (b) recovering said protein.

54. A method of producing a protein comprising: (a) culturing the host cell of claim 44 under conditions such that said protein is expressed; and (b) recovering said protein.

55. A method of producing a protein comprising: (a) culturing the host cell of claim 45 under conditions such that said protein is expressed; and (b) recovering said protein.

56. A method of producing a protein comprising: (a) culturing the host cell of claim 46 under conditions such that said protein is expressed; and (b) recovering said protein.

* * * * *

SEQUENCE LISTING (1) GENERAL INFORMATION:

(iii) NUMBER OF SEQUENCES: 22

(2) INFORMATION FOR SEQ ID NO:1:

(i) SEQUENCE CHARACTERISTICS:
        (A) LENGTH: 550 base pairs
        (B) TYPE: nucleic acid
        (C) STRANDEDNESS: single
        (D) TOPOLOGY: linear (ii) MOLECULE TYPE: DNA (xi) SEQUENCE DESCRIPTION: SEQ ID NO:1:

```
CACGAGCCAC C ATG GAT GTT TTC AAG AAG GGC TTC TCC ATC GCC AAG AAG      50
            Met Asp Val Phe Lys Lys Gly Phe Ser Ile Ala Lys Lys
              1               5                  10

GGC GTG GTG GGT GCG GTG GAA AAG ACC AAG CAG GGG GTG ACG GAA GCA       98
Gly Val Val Gly Ala Val Glu Lys Thr Lys Gln Gly Val Thr Glu Ala
 15                  20                  25

GCT GAG AAG ACC AAG GAG GGG GTC ATG TAT GTG GGA GCC AAG ACC AAG      146
Ala Glu Lys Thr Lys Glu Gly Val Met Tyr Val Gly Ala Lys Thr Lys
 30                  35                  40                  45

GAG AAT GTT GTA CAG AGC GTG ACC TCA GTG GCC GAG AAG ACC AAG GAG      194
Glu Asn Val Val Gln Ser Val Thr Ser Val Ala Glu Lys Thr Lys Glu
                 50                  55                  60

CAG GCC AAC GCC GTG AGC AAG GCT GTG GTG AGC AGC GTC AAC ACT GTG      242
Gln Ala Asn Ala Val Ser Lys Ala Val Val Ser Ser Val Asn Thr Val
             65                  70                  75

GCC ACC AAG ACC GTG GAG GAG GCG GAG AAC ATC GCG GTC ACC TCC GGG      290
Ala Thr Lys Thr Val Glu Glu Ala Glu Asn Ile Ala Val Thr Ser Gly
             80                  85                  90

GTG GTG CGC AAG GAG GAC TTG AGG CCA TCT GCC CCC CAA CAG GAG GGT      338
Val Val Arg Lys Glu Asp Leu Arg Pro Ser Ala Pro Gln Gln Glu Gly
 95                  100                 105

GAG GCA TCC AAA GAG AAA GAG GAA GTG GCA GAG GAG GCC CAG AGT GGG      386
Glu Ala Ser Lys Glu Lys Glu Glu Val Ala Glu Glu Ala Gln Ser Gly
110                 115                 120                 125

GGA GAC T AGAGGGCTAC AGGCCAGCGT GGATGACCTG AAGAGCGCTC CTCTGCCTTG     443
Gly Asp

GACACCATCC CCTCCTAGCA CAAGGAGTGC CCGCCTTGAG TGACATGCGG GTGCCCACGC    503

TCCTGCCCTC GTCTCCCTGG ACACCCTTGG CCTGTCCACC TGTGCTG                 550
```

(2) INFORMATION FOR SEQ ID NO:2:

(i) SEQUENCE CHARACTERISTICS:
        (A) LENGTH: 1720 base pairs
        (B) TYPE: nucleic acid
        (C) STRANDEDNESS: single
        (D) TOPOLOGY: linear (ii) MOLECULE TYPE: DNA (xi) SEQUENCE DESCRIPTION: SEQ ID NO:2:

```
AATTCCTGGG GGGTCTCGGC GAGGGAGTCA TCAAGCTTTG GTGTATGTGT TGGCCGGTTC     60

TGAAGTCTTG AAGAAGCTCT GCTGAGGAAG ACCAAAGCAG CACTCGTTGC CAATTAGGGA    120

ATG GAC CGT TTG GGT TCC TTT AGC AAT GAT CCC TCT GAT AAG CCA CCT      168
Met Asp Arg Leu Gly Ser Phe Ser Asn Asp Pro Ser Asp Lys Pro Pro
              5                  10                  15
```

| | | | | | | | | | | | | | | | | |
|---|---|---|---|---|---|---|---|---|---|---|---|---|---|---|---|---|
| TGC | CGA | GGC | TGC | TCC | TCC | TAC | CTC | ATG | GAG | CCT | TAT | ATC | AAG | TGT | GCT | 216 |
| Cys | Arg | Gly | Cys | Ser | Ser | Tyr | Leu | Met | Glu | Pro | Tyr | Ile | Lys | Cys | Ala | |
| | | | 20 | | | | | 25 | | | | | 30 | | | |
| GAA | TGT | GGG | CCA | CCT | CCT | TTT | TTC | CTC | TGC | TTG | CAG | TGT | TTC | ACT | CGA | 264 |
| Glu | Cys | Gly | Pro | Pro | Pro | Phe | Phe | Leu | Cys | Leu | Gln | Cys | Phe | Thr | Arg | |
| | | | 35 | | | | | 40 | | | | | 45 | | | |
| GGC | TTT | GAG | TAC | AAG | AAA | CAT | CAA | AGC | GAT | CAT | ACT | TAT | GAA | ATA | ATG | 312 |
| Gly | Phe | Glu | Tyr | Lys | Lys | His | Gln | Ser | Asp | His | Thr | Tyr | Glu | Ile | Met | |
| | 50 | | | | | 55 | | | | | 60 | | | | | |
| ACT | TCA | GAT | TTT | CCT | GTC | CTT | GAT | CCC | AGC | TGG | ACT | GCT | CAA | GAA | GAA | 360 |
| Thr | Ser | Asp | Phe | Pro | Val | Leu | Asp | Pro | Ser | Trp | Thr | Ala | Gln | Glu | Glu | |
| 65 | | | | | 70 | | | | | 75 | | | | | 80 | |
| ATG | GCC | CTT | TTA | GAA | GCT | GTG | ATG | GAC | TGT | GGC | TTT | GGA | AAT | TGG | CAG | 408 |
| Met | Ala | Leu | Leu | Glu | Ala | Val | Met | Asp | Cys | Gly | Phe | Gly | Asn | Trp | Gln | |
| | | | | 85 | | | | | 90 | | | | | 95 | | |
| GAT | GTA | GCC | AAT | CAA | ATG | TGC | ACC | AAG | ACC | AAG | GAG | GAG | TGT | GAG | AAG | 456 |
| Asp | Val | Ala | Asn | Gln | Met | Cys | Thr | Lys | Thr | Lys | Glu | Glu | Cys | Glu | Lys | |
| | | | 100 | | | | | 105 | | | | | 110 | | | |
| CAC | TAT | ATG | AAG | CAT | TTC | ATC | AAT | AAC | CCT | CTG | TTT | GCA | TCT | ACC | CTG | 504 |
| His | Tyr | Met | Lys | His | Phe | Ile | Asn | Asn | Pro | Leu | Phe | Ala | Ser | Thr | Leu | |
| | | | 115 | | | | | 120 | | | | | 125 | | | |
| CTG | AAC | CTG | AAA | CAA | GCA | GAG | GAA | GCA | AAA | ACT | GCT | GAC | ACA | GCC | ATT | 552 |
| Leu | Asn | Leu | Lys | Gln | Ala | Glu | Glu | Ala | Lys | Thr | Ala | Asp | Thr | Ala | Ile | |
| | | 130 | | | | | 135 | | | | | 140 | | | | |
| CCA | TTT | CAC | TCT | ACA | GAT | GAC | CCT | CCC | CGA | CCT | ACC | TTT | GAC | TCC | TTG | 600 |
| Pro | Phe | His | Ser | Thr | Asp | Asp | Pro | Pro | Arg | Pro | Thr | Phe | Asp | Ser | Leu | |
| 145 | | | | | 150 | | | | | 155 | | | | | 160 | |
| CTT | TCT | CGG | GAC | ATG | GCC | GGG | TAC | ATG | CCA | GCT | CGA | GCA | GAT | TTC | ATT | 648 |
| Leu | Ser | Arg | Asp | Met | Ala | Gly | Tyr | Met | Pro | Ala | Arg | Ala | Asp | Phe | Ile | |
| | | | | 165 | | | | | 170 | | | | | 175 | | |
| GAG | GAA | TTT | GAC | AAT | TAT | GCA | GAA | TGG | GAC | TTG | AGA | GAC | ATT | GAT | TTT | 696 |
| Glu | Glu | Phe | Asp | Asn | Tyr | Ala | Glu | Trp | Asp | Leu | Arg | Asp | Ile | Asp | Phe | |
| | | | 180 | | | | | 185 | | | | | 190 | | | |
| GTT | GAA | GAT | GAC | TCG | GAC | ATT | TTA | CAT | GCT | CTG | AAG | ATG | GCT | GTG | GTA | 744 |
| Val | Glu | Asp | Asp | Ser | Asp | Ile | Leu | His | Ala | Leu | Lys | Met | Ala | Val | Val | |
| | | 195 | | | | | 200 | | | | | 205 | | | | |
| GAT | ATC | TAT | CAT | TCC | AGG | TTA | AAG | GAG | AGA | CAA | AGA | CGA | AAA | AAA | ATT | 792 |
| Asp | Ile | Tyr | His | Ser | Arg | Leu | Lys | Glu | Arg | Gln | Arg | Arg | Lys | Lys | Ile | |
| | 210 | | | | | 215 | | | | | 220 | | | | | |
| ATA | AGA | GAC | CAT | GGA | TTA | ATC | AAC | CTT | AGA | AAG | TTT | CAA | TTA | ATG | GAA | 840 |
| Ile | Arg | Asp | His | Gly | Leu | Ile | Asn | Leu | Arg | Lys | Phe | Gln | Leu | Met | Glu | |
| 225 | | | | | 230 | | | | | 235 | | | | | 240 | |
| CGG | CGG | TAT | CCC | AAG | GAG | GTC | CAG | GAC | CTG | TAT | GAA | ACA | ATG | AGG | CGA | 888 |
| Arg | Arg | Tyr | Pro | Lys | Glu | Val | Gln | Asp | Leu | Tyr | Glu | Thr | Met | Arg | Arg | |
| | | | | 245 | | | | | 250 | | | | | 255 | | |
| TTT | GCA | AGA | ATT | GTG | GGG | CCA | GTG | GAA | CAT | GAC | AAA | TTC | ATT | GAA | AGC | 936 |
| Phe | Ala | Arg | Ile | Val | Gly | Pro | Val | Glu | His | Asp | Lys | Phe | Ile | Glu | Ser | |
| | | | 260 | | | | | 265 | | | | | 270 | | | |
| CAT | GCA | TTG | GAA | TTT | GAA | CTC | CGA | AGG | GAA | ATC | AAG | AGG | CTC | CAA | GAA | 984 |
| His | Ala | Leu | Glu | Phe | Glu | Leu | Arg | Arg | Glu | Ile | Lys | Arg | Leu | Gln | Glu | |
| | | | 275 | | | | | 280 | | | | | 285 | | | |
| TAC | AGG | ACA | GCA | GGC | ATT | ACC | AAT | TTT | TGT | AGT | GCC | AGA | ACC | TAC | GAT | 1032 |
| Tyr | Arg | Thr | Ala | Gly | Ile | Thr | Asn | Phe | Cys | Ser | Ala | Arg | Thr | Tyr | Asp | |
| | | 290 | | | | | 295 | | | | | 300 | | | | |
| CAC | CTC | AAG | AAG | ACA | CGG | GAG | GAA | GAG | CGC | CTT | AAA | CGC | ACT | ATG | CTC | 1080 |
| His | Leu | Lys | Lys | Thr | Arg | Glu | Glu | Glu | Arg | Leu | Lys | Arg | Thr | Met | Leu | |
| 305 | | | | | 310 | | | | | 315 | | | | | 320 | |
| TCA | GAA | GTT | CTC | CAG | TAT | ATC | CAG | GAC | AGT | AGT | GCT | TGC | CAG | CAG | TGG | 1128 |
| Ser | Glu | Val | Leu | Gln | Tyr | Ile | Gln | Asp | Ser | Ser | Ala | Cys | Gln | Gln | Trp | |

```
                 325                  330                   335
CTC CGC CGG CAA GCT GAC ATT GAT TCC GGC CTG AGT CCT TCC ATT CCA              1176
Leu Arg Arg Gln Ala Asp Ile Asp Ser Gly Leu Ser Pro Ser Ile Pro
                340                  345                   350

ATG GCT TCG AAT TCA GGT AGA CGG AGT GCA CCA CCC TTG AAC CTC ACT              1224
Met Ala Ser Asn Ser Gly Arg Arg Ser Ala Pro Pro Leu Asn Leu Thr
                355                  360                   365

GGC CTC CCT GGC ACA GAG AAG CTG AAT GAA AAA GAA AAG GAG CTC TGT              1272
Gly Leu Pro Gly Thr Glu Lys Leu Asn Glu Lys Glu Lys Glu Leu Cys
    370                  375                  380

CAG ATG GTG AGG TTG GTC CCT GGA GCC TAT TTA GAA TAC AAA TCT GCT              1320
Gln Met Val Arg Leu Val Pro Gly Ala Tyr Leu Glu Tyr Lys Ser Ala
385                  390                   395                  400

CTA TTG AAC GAA TGT AAC AAG CAA GGA GGC TTA AGA CTG GCG CAG GCA              1368
Leu Leu Asn Glu Cys Asn Lys Gln Gly Gly Leu Arg Leu Ala Gln Ala
                405                  410                   415

AGA GCA CTC ATC AAG ATA GAT GTG AAC AAA ACC CGG AAA ATC TAT GAT              1416
Arg Ala Leu Ile Lys Ile Asp Val Asn Lys Thr Arg Lys Ile Tyr Asp
                420                  425                   430

TTC CTC ATC AGA GAA GGA TAC ATC ACT AAA GGC T AAGGCTCCAA                     1460
Phe Leu Ile Arg Glu Gly Tyr Ile Thr Lys Gly
                435                  440

GAGCTTGGGA TCAGAAGTCA GAAGTTTGGA ATGTGGTGGG TCAAAGGACA ATATGGGTGG            1520

GCATTCTGGA GAGTTTGTTT TTCAGCTGAA TTCTCATGGT GAAAACAGGG GAAAGGACAA            1580

AGGAAACCTT AAGTTGTATT GTCTACTTTC TTCTCCATCC TGCTTTAAAA CACTCCTGTT            1640

GTTGGTATTA TGCTGCAGAG TTGTGTGCTA CATAAGCTAT TATTAAATGT GAGTGGGCAT            1700

TCAAAAAAAA AAAAAAAAA                                                        1720

(2) INFORMATION FOR SEQ ID NO:3:

(i) SEQUENCE CHARACTERISTICS:
        (A) LENGTH: 1537 base pairs
        (B) TYPE: nucleic acid
        (C) STRANDEDNESS: single
        (D) TOPOLOGY: linear (ii) MOLECULE TYPE: DNA (xi) SEQUENCE DESCRIPTION: SEQ ID NO:3:

GGCACGAGGC GCCCCCGGGG TCCCCCGGCC CCTGCAGGGC TACTTGGGCG CAGAGCCGCG              60

GAGGGTCTCC GTTCCTAGAG GTCCTCCTAT CCCGGGCTGC CTGAGTCCTC GCCAGCATCC             120

GCCCTCTCCC ACTCCCATCC TTCCTGGATC CGCCTCTCGG TTCCCGAGGG ACAGTCCCGA             180

CCGCAAACCC ACGTAGAGTA AGGAATGTGG GACAGGCGAC AGAAGTGGCA TACGGTCCTG             240

CGTTATCCCT CCGTCTCGCC ACACCTTGTG TCTCCATCTC TCCCCACTTC CTTCCCTCCG             300

TCTGTCATCT GTCATCCCCG GTCGCTCTAA GACCAGGATT CCAATTCGCC TAGTGAGGAA             360

TCTCACTAGG GGAATTTATC GCGACATCAT AAATTAACGG GTTCATTTTG ACTGAAAAGC             420

GAAGGACTTT TTTCAGGCAG AAAACAAGTC TCGTCTGGAC GGATGTGATC TTCGTGGTGG             480

AAAGCTAAAT TTTAAAACCA CCCCA ATG GAT GCA GAC AGT GAT GTT GCA TTG               532
                             Met Asp Ala Asp Ser Asp Val Ala Leu
                             1               5

GAC ATT CTA ATT ACA AAT GTA GTC TGT GTT TTT AGA ACA AGA TGT CAT               580
Asp Ile Leu Ile Thr Asn Val Val Cys Val Phe Arg Thr Arg Cys His
    10                  15                  20                  25

TTA AAC TTA AGG AAG ATT GCT TTG GAA GGA GCA AAT GTA ATT TAT AAA               628
Leu Asn Leu Arg Lys Ile Ala Leu Glu Gly Ala Asn Val Ile Tyr Lys
```

```
                    30                   35                    40
CGT GAT GTT GGA AAA GTA TTA ATG AAG CTT AGA AAA CCT AGA ATT ACA       676
Arg Asp Val Gly Lys Val Leu Met Lys Leu Arg Lys Pro Arg Ile Thr
                    45                  50                   55

GCT ACA ATT TGG TCC TCA GGA AAA ATT ATT TGC ACT GGA GCA ACA AGT       724
Ala Thr Ile Trp Ser Ser Gly Lys Ile Ile Cys Thr Gly Ala Thr Ser
                60                  65                  70

GAA GAA GAA GCT AAA TTT GGT GCC AGA CGC TTA GCC CGT AGT CTG CAG       772
Glu Glu Glu Ala Lys Phe Gly Ala Arg Arg Leu Ala Arg Ser Leu Gln
            75                  80                  85

AAA CTA GGT TTT CAG GTA ATA TTT ACA GAT TTT AAG GTT GTT AAC GTT       820
Lys Leu Gly Phe Gln Val Ile Phe Thr Asp Phe Lys Val Val Asn Val
        90                  95                 100                 105

CTG GCA GTG TGT AAC ATG CCA TTT GAA ATC CGT TTG CCA GAA TTC ACA       868
Leu Ala Val Cys Asn Met Pro Phe Glu Ile Arg Leu Pro Glu Phe Thr
                   110                 115                 120

AAG AAC AAT AGA CCT CAT GCC AGT TAC GAA CCT GAA CTT CAT CCT GCT       916
Lys Asn Asn Arg Pro His Ala Ser Tyr Glu Pro Glu Leu His Pro Ala
               125                 130                 135

GTG TGC TAT CGG ATA AAA TCT CTA AGA GCT ACA TTA CAG ATT TTT TCA       964
Val Cys Tyr Arg Ile Lys Ser Leu Arg Ala Thr Leu Gln Ile Phe Ser
           140                 145                 150

ACA GGA AGT ATC ACA GTA ACA GGG CCC AAT GTA AAG GCT GTT GCT ACT      1012
Thr Gly Ser Ile Thr Val Thr Gly Pro Asn Val Lys Ala Val Ala Thr
       155                 160                 165]

GCT GTG GAA CAG ATT TAC CCA TTT GTG TTT GAA AGC AGG AAA GAA ATT      1060
Ala Val Glu Gln Ile Tyr Pro Phe Val Phe Glu Ser Arg Lys Glu Ile
170                 175                 180                 185

TTA T AATTCACCAC TTAATTGGTT AGAATCTCTA ACTGAGCACC TTTTAAACCT         1114
Leu

GCTGCACATT GGACTCAAAA GGAAAACTGG ACCAACAATA ATTGAGGAAA TAGACTTTTT    1174

TATTCATTCA CGGCTACAGT GTAAGCTCCA GTCCCTTTGG ATTTTATTCC AAACCTTGCT    1234

GTAATATAAA AGGAAGTTTA CAAGACATGA TATTGCTGCT TTTACAAAAG GACATTCTAT    1294

TTATTTTCGC AGTAATTCTC ATGTCCCCAT AAGCAGAGCT GTCACAGTGT GCACTACCTT    1354

AGATTGTTTT ATTGTCGTCA TTGTTATTTT TTTCCATTTG GAGCTAATGT GTTTTATTTG    1414

TGAATAGTCT TTTACATTTT TGTATGCTGA ATATGGGCAC CAAAGAACCT GTAAAAGTTA    1474

TCTTTTTCAA TTGAATGTGC ACAAATAAAA GTTTGGAAAG AAAAAAAAAA AAAAAAAAA    1534

AAA                                                                  1537

(2) INFORMATION FOR SEQ ID NO:4:

(i) SEQUENCE CHARACTERISTICS:
        (A) LENGTH: 555 base pairs
        (B) TYPE: nucleic acid
        (C) STRANDEDNESS: single
        (D) TOPOLOGY: linear (ii) MOLECULE TYPE: DNA (xi) SEQUENCE DESCRIPTION: SEQ ID NO:4:

ACGAGCAACG GCGGCGGGAG C ATG AAC GCC CCT CCA GCC TTC GAG TCG TTC       51
                        Met Asn Ala Pro Pro Ala Phe Glu Ser Phe
                         1               5                  10

TTG CTC TTC GAG GGC GAG AAG AAG ATC ACC ATT AAC AAG GAC ACC AAG       99
Leu Leu Phe Glu Gly Glu Lys Lys Ile Thr Ile Asn Lys Asp Thr Lys
            15                  20                  25

GTA CCC AAT GCC TGT TTA TTC ACC ATC AAC AAA GAA GAC CAC ACA CTG      147
Val Pro Asn Ala Cys Leu Phe Thr Ile Asn Lys Glu Asp His Thr Leu
```

```
                    30                   35                   40
GGA AAC ATC ATT AAA TCA CAA CTC CTA AAA GAC CCG CAA GTG CTA TTT        195
Gly Asn Ile Ile Lys Ser Gln Leu Leu Lys Asp Pro Gln Val Leu Phe
             45                   50                   55

GCT GGC TAC AAA GTC CCC CAC CCC TTG GAG CAC AAG ATC ATC ATC CGA        243
Ala Gly Tyr Lys Val Pro His Pro Leu Glu His Lys Ile Ile Ile Arg
         60                   65                   70

GTG CAG ACC ACG CCG GAC TAC AGC CCC CAG GAA GCC TTT ACC AAC GCC        291
Val Gln Thr Thr Pro Asp Tyr Ser Pro Gln Glu Ala Phe Thr Asn Ala
 75                   80                   85                   90

ATC ACC GAC CTC ATC AGT GAG CTG TCC CTG CTG GAG GAG CGC TTT CGG        339
Ile Thr Asp Leu Ile Ser Glu Leu Ser Leu Leu Glu Glu Arg Phe Arg
                 95                  100                  105

GTG GCC ATA AAA GAC AAG CAG GAA GGA ATT GAG T AGGGGCCAGA               383
Val Ala Ile Lys Asp Lys Gln Glu Gly Ile Glu
             110                  115

GGGGGCTCTG CTCGGCCTGT GAGCCCCGTT CCTACCTGTG CCTGACCCTC CGCTCCAGGT      443

ACCACACCGA GGAGAGCGGC CAGTCCCAGC CATGGCCCGC CTTGTGGCCA CCCCTCACCC      503

TGACACCGAC GTGTCCTGTA CATAGATTAG GTTTTATATT CCTAATAAAG TA              555

(2) INFORMATION FOR SEQ ID NO:5:

(i) SEQUENCE CHARACTERISTICS:
        (A) LENGTH: 1426 base pairs
        (B) TYPE: nucleic acid
        (C) STRANDEDNESS: single
        (D) TOPOLOGY: linear (ii) MOLECULE TYPE: DNA (xi) SEQUENCE DESCRIPTION: SEQ ID NO:5:

GGTTCCAGCT GCCCGCACGC CCCGACCTTC CATCGTAGGC CGGACCATGG GAACCCCAAA        60

GCCACGGNTC CTGCCCTGGC TGGTGTCGCA GCTGGACCTG GGCAACTGG AGGGCGTGGC        120

CTGGGTGAAC AAGAGCCGCA CGCGCTTCCG CATCCCTTGG AAGCACGGCC TACGGCAGGA      180

TGCACAGCAG GAGGATTTCG GAATCTTCCA GGCCTGGGCC GAGGCCACTG GTGCATATGT      240

TCCCGGGAGG GATAAGCCAG ACCTGCCAAC CTGGAAGAGG AATTTCCGCT CTGCCCTCAA      300

CCGCAAAGAA GGGTTGCGTT TAGCAGAGGA CCGGAGCAAG GACCCTCACG ACCCACATAA      360

AATCTACGAG TTTGTGAACT CAGGAGTTGG GGACTTTTCC CAGCCAGACA CCTCTCCGGA      420

CACCAATGGT GGAGGCAGTA CTTCTGATAC CCAGGAAGAC ATTCTGGATG AGTTACTGGG      480

TAACATGGTG TTGGCCCCAC TCCCAGATCC GGGACCCCCA AGCCTGGCTG TAGCCCCTGA      540

GCCCTGCCCT CAGCCCCTGC GGAGCCCCAG CTTGGACAAT CCCACTCCCT TCCCAAACCT      600

GGGGCCCTCT GAGAACCCAC TGAAGCGGCT GTTGGTGCCG GGGGAAGAGT GGGAGTTCGA      660

GGTGACAGCC TTCTACCGGG GCCGCCAAGT CTTCCAGCAG ACCATCTCCT GCCCGGAGGG      720

CCTGCGGCTG GTGGGGTCCG AAGTGGGAGA CAGGACGCTG CCTGGATGGC CAGTCACACT      780

GCCAGACCCT GGCATGTCCC TGACAGACAG GGGAGTGATG AGCTACGTGA GGCATGTGCT      840

GAGCTGCCTG GGTGGGGGAC TGGCTCTCTG GCGGGCCGGG CAGTGGCTCT GGGCCCAGCG      900

GCTGGGGCAC TGCCACACAT ACTGGGCAGT GAGCGAGGAG CTGCTCCCCA ACAGCGGGCA      960

TGGGCCTGAT GGCGAGGTCC CCAAGGACAA GGAAGGAGGC GTGTTTGACC TGGGGCCCTT     1020

CATTGTAGAT CTGATTACCT TCACGGAAGG AAGCGGACGC TCACCACGCT ATGCCCTCTG     1080

GTTCTGTGTG GGGGAGTCAT GGCCCCAGGA CCAGCCGTGG ACCAAGAGGC TCGTGATGGT     1140
```

```
CAAGGTTGTG CCCACGTGCC TCAGGGCCTT GGTAGAAATG GCCCGGGTAG GGGGTGCCTC    1200

CTCCCTGGAG AATACTGTGG ACCTGCACAT TTCCAACAGC CACCCACTCT CCCTCACCTC    1260

CGACCAGTAC AAGGCCTACC TGCAGGACTT GGTGGAGGGC ATGGATTTCC AGGGCCCTGG    1320

GGAGAGCTGA GCCCTCGCTC CTCATGGTGT GCCTCCAACC CCCTGTTCC CCACCACCTC     1380

AACCAATAAA CTGGTTCCTG CTATGAAAAA AAAAAAAAA AAAAAA                    1426

(2) INFORMATION FOR SEQ ID NO:6:

(i) SEQUENCE CHARACTERISTICS:
        (A) LENGTH: 1001 base pairs
        (B) TYPE: nucleic acid
        (C) STRANDEDNESS: single
        (D) TOPOLOGY: linear (ii) MOLECULE TYPE: DNA (xi) SEQUENCE DESCRIPTION: SEQ ID NO:6:

AATTCGGCAG AGGCAGTTCC TAGCGAGGAG GCGCCGCGCA TTGCCGCTCT CTCGGTGAGC      60

GCAGCCCGCT CTCCGGGCCG GGCCTTCGCG GGCCACCGCG CC ATG GGC CAG TGC       114
                                              Met Gly Gln Cys
                                               1

GGC ATC ACC TCC TCC AAG ACC GTG CTG GTC TTT CTC AAC CTC ATC TTC      162
Gly Ile Thr Ser Ser Lys Thr Val Leu Val Phe Leu Asn Leu Ile Phe
  5                  10                  15                  20

TGG GGG GCA GCT GGC ATT TTA TGC TAT GTG GGA GCC TAT GTC TTC ATC      210
Trp Gly Ala Ala Gly Ile Leu Cys Tyr Val Gly Ala Tyr Val Phe Ile
                 25                  30                  35

ACT TAT GAT GAC TAT GAC CAC TTC TTT GAA GAT GTG TAC ACG CTC ATC      258
Thr Tyr Asp Asp Tyr Asp His Phe Phe Glu Asp Val Tyr Thr Leu Ile
             40                  45                  50

CCT GCT GTA GTG ATC ATA GCT GTA GGA GCC CTG CTT TTC ATC ATT GGG      306
Pro Ala Val Val Ile Ile Ala Val Gly Ala Leu Leu Phe Ile Ile Gly
         55                  60                  65

CTA ATT GGC TGC TGT GCC ACA ATC CGG GAA AGT CGC TGT GGA CTT GCC      354
Leu Ile Gly Cys Cys Ala Thr Ile Arg Glu Ser Arg Cys Gly Leu Ala
     70                  75                  80

ACG TTT GTC ATC ATC CTG CTC TTG GTT TTT GTC ACA GAA GTT GTT GTA      402
Thr Phe Val Ile Ile Leu Leu Leu Val Phe Val Thr Glu Val Val Val
 85                  90                  95                 100

GTG GTT TTG GGA TAT GTT TAC AGA GCA AAG GTG GAA AAT GAG GTT GAT      450
Val Val Leu Gly Tyr Val Tyr Arg Ala Lys Val Glu Asn Glu Val Asp
                105                 110                 115

CGC AGC ATT CAG AAA GTG TAT AAG ACC TAC AAT GGA ACC AAC CCT GAT      498
Arg Ser Ile Gln Lys Val Tyr Lys Thr Tyr Asn Gly Thr Asn Pro Asp
            120                 125                 130

GCT GCT AGC CGG GCT ATT GAT TAT GTA CAG AGA CAG CTG CAT TGT TGT      546
Ala Ala Ser Arg Ala Ile Asp Tyr Val Gln Arg Gln Leu His Cys Cys
        135                 140                 145

GGA ATT CAC AAC TAC TCA GAC TGG GAA AAT ACA GAT TGG TTC AAA GAA      594
Gly Ile His Asn Tyr Ser Asp Trp Glu Asn Thr Asp Trp Phe Lys Glu
    150                 155                 160

ACC AAA AAC CAG AGT GTC CCT CTT AGC TGC TGC AGA GAG ACT GCC AGC      642
Thr Lys Asn Gln Ser Val Pro Leu Ser Cys Cys Arg Glu Thr Ala Ser
165                 170                 175                 180

AAT TGT AAT GGC AGC TGG CCA CCC TTC CGA CTC TAT GCT GAG GGG TGT      690
Asn Cys Asn Gly Ser Trp Pro Pro Phe Arg Leu Tyr Ala Glu Gly Cys
                185                 190                 195

GAG GCT CTA GTT GTG AAG AAG CTA CAA GAA ATC ATG ATG CAT GTG ATC      738
Glu Ala Leu Val Val Lys Lys Leu Gln Glu Ile Met Met His Val Ile
```

```
                    200              205                 210
TGG GCC GCA CTG GCA TTT GCA GCT ATT CAG CTG CTG GGC ATG CTG TGT    786
Trp Ala Ala Leu Ala Phe Ala Ala Ile Gln Leu Leu Gly Met Leu Cys
        215                 220                 225

GCT TGC ATC GTG TTG TGC AGA AGG AGT AGA GAT CCT GCT TAC GAG CTC    834
Ala Cys Ile Val Leu Cys Arg Arg Ser Arg Asp Pro Ala Tyr Glu Leu
    230                 235                 240

CTC ATC ACT GGC GGA ACC TAT GCA TAG T TGACAACTCA AGCCTGAGCT        882
Leu Ile Thr Gly Gly Thr Tyr Ala
245                 250

TTTTGGTCTT GTTCTGATTT GGAAGGTGAA TTGAGCAGGT CTGCTGCTGT TGGCCTCTGG  942

AGTTCATCTA GTTAAAGCAC ATGTACACTG GTGTTGGACA GAGCAGCTTG GCTTTTCAT   1001

(2) INFORMATION FOR SEQ ID NO:7:

(i) SEQUENCE CHARACTERISTICS:
        (A) LENGTH: 2361 base pairs
        (B) TYPE: nucleic acid
        (C) STRANDEDNESS: single
        (D) TOPOLOGY: linear (ii) MOLECULE TYPE: DNA (xi) SEQUENCE DESCRIPTION: SEQ ID NO:7:

GAGCCAGGAC TCCACAAGGC TGGTCCCCTG CCCTGGAGCA ACTTAAACAG GCCCTCTGGC    60

CAGCCTGGAA CCCTGAG ATG GCC TCC AGC TCA GGC AGC AGT CCT CGC CCG      110
                    Met Ala Ser Ser Ser Gly Ser Ser Pro Arg Pro
                     1               5                  10

GCC CCT GAT GAG AAT GAG TTT CCC TTT GGG TGC CCT CCC ACC GTC TGC     158
Ala Pro Asp Glu Asn Glu Phe Pro Phe Gly Cys Pro Pro Thr Val Cys
            15                  20                  25

CAG GAC CCA AAG GAG CCC AGG GCT CTC TGC TGT GCA GGC TGT CTC TCT     206
Gln Asp Pro Lys Glu Pro Arg Ala Leu Cys Cys Ala Gly Cys Leu Ser
        30                  35                  40

GAG AAC CCG AGG AAT GGC GAG GAT CAG ATC TGC CCC AAA TGC AGA GGG     254
Glu Asn Pro Arg Asn Gly Glu Asp Gln Ile Cys Pro Lys Cys Arg Gly
    45                  50                  55

GAA GAC CTC CAG TCT ATA AGC CCA GGA AGC CGT CTT CGA ACT CAG GAG     302
Glu Asp Leu Gln Ser Ile Ser Pro Gly Ser Arg Leu Arg Thr Gln Glu
60                  65                  70                  75

AAG GTT CAG GCG GAG GTC GCT GAG GCT GGG ATT GGG TGC CCC TTT GCT     350
Lys Val Gln Ala Glu Val Ala Glu Ala Gly Ile Gly Cys Pro Phe Ala
                80                  85                  90

GTT GTC GGC TGC TCC TTC AAG GGA AGC CCA CAG TTT GTG GAA GAG CAT     398
Val Val Gly Cys Ser Phe Lys Gly Ser Pro Gln Phe Val Glu Glu His
            95                 100                 105

GAG GTC ACC TCC CAG ACC TCC CAC CTA AAC CTG CTG TTG GGG TTC ATG     446
Glu Val Thr Ser Gln Thr Ser His Leu Asn Leu Leu Leu Gly Phe Met
        110                 115                 120

AAA CAG TGG AAG GCC CGG CTG GGC TGT GGC CTG GAT TCT GGG CCC ATG     494
Lys Gln Trp Lys Ala Arg Leu Gly Cys Gly Leu Asp Ser Gly Pro Met
    125                 130                 135

GCC CTG GAG CAG AAC CTG TCA GAC CTG CAG CTG CAG GCA GCC GTG GAA     542
Ala Leu Glu Gln Asn Leu Ser Asp Leu Gln Leu Gln Ala Ala Val Glu
140                 145                 150                 155

GTG GCG GGG GAC CTG GAG GTC GAT TGC TAC CGG GCA CCC TGC TCC GAG     590
Val Ala Gly Asp Leu Glu Val Asp Cys Tyr Arg Ala Pro Cys Ser Glu
                160                 165                 170

AGC CAG GAG GAG CTG GCC CTG CAG CAC TTC ATG AAG GAG AAG CTT CTG     638
Ser Gln Glu Glu Leu Ala Leu Gln His Phe Met Lys Glu Lys Leu Leu
```

-continued

```
                       175                 180                 185
GCT GAG CTG GAG GGG AAG CTG CGT GTG TTT GAG AAC AAT GTT GCT GTC        686
Ala Glu Leu Glu Gly Lys Leu Arg Val Phe Glu Asn Asn Val Ala Val
                190                 195                 200

CTC AAC AAG GAG GTG GAG GCC TCC CAC CTG GCC CTG GCC ACC TCT ATC        734
Leu Asn Lys Glu Val Glu Ala Ser His Leu Ala Leu Ala Thr Ser Ile
            205                 210                 215

CAC CAG AGC CAG CTG GAC CGT GAG CGC ATC CTG AGC TTG GAG CAG AGG        782
His Gln Ser Gln Leu Asp Arg Glu Arg Ile Leu Ser Leu Glu Gln Arg
220                 225                 230                 235

GTG GTG CAG GTT CAG CAG ACC CTG GCC CAG AAA GAC CAG GCC CTG GGC        830
Val Val Gln Val Gln Gln Thr Leu Ala Gln Lys Asp Gln Ala Leu Gly
                240                 245                 250

AAG CTG GAG CAG AGC TTG CGC CTC ATG GAG GAG GCC TCC TTC GAT GGC        878
Lys Leu Glu Gln Ser Leu Arg Leu Met Glu Glu Ala Ser Phe Asp Gly
            255                 260                 265

ACT TTC CTG TGG AAG ATC ACC AGT GTC ACC AGG CGG TGC CAT GAG TCG        926
Thr Phe Leu Trp Lys Ile Thr Ser Val Thr Arg Arg Cys His Glu Ser
        270                 275                 280

GCC TGT GGC AGG ACC GTC AGC CTC TTC TCC CCA GCC TTC TAC ACT GCC        974
Ala Cys Gly Arg Thr Val Ser Leu Phe Ser Pro Ala Phe Tyr Thr Ala
    285                 290                 295

AAG TAT GGC TAC AAG TTG TGC CTG CGG CTG TAC CTG ATT GGA GAT GGC       1022
Lys Tyr Gly Tyr Lys Leu Cys Leu Arg Leu Tyr Leu Ile Gly Asp Gly
300                 305                 310                 315

ACT GGA AAG AGA ACC CAT CTT TCG CTC TTC ATC GTG ATC ATG AGA GGG       1070
Thr Gly Lys Arg Thr His Leu Ser Leu Phe Ile Val Ile Met Arg Gly
                320                 325                 330

GAG TAT GAT GCG CTG CTG CCG TGG CCT TTC CGG AAC AAG GTC ACC TTC       1118
Glu Tyr Asp Ala Leu Leu Pro Trp Pro Phe Arg Asn Lys Val Thr Phe
            335                 340                 345

ATG CTG CTG GAC CAG AAC AAC CGT GAG CAC GCC ATT GAC GCC TTC CGG       1166
Met Leu Leu Asp Gln Asn Asn Arg Glu His Ala Ile Asp Ala Phe Arg
        350                 355                 360

CCT GAC CTA AGC TCA GCG TCC TTC CAG AGG CCC CAG AGT GAA ACC AAC       1214
Pro Asp Leu Ser Ser Ala Ser Phe Gln Arg Pro Gln Ser Glu Thr Asn
    365                 370                 375

GTG GCC AGT GGA TGC CCA CTC TTC TTC CCC CTC AGC AAA CTG CAG TCA       1262
Val Ala Ser Gly Cys Pro Leu Phe Phe Pro Leu Ser Lys Leu Gln Ser
380                 385                 390                 395

CCC AAG CAC GCC TAC GTA AGG ACG ACA CAA TGT TCC TCA AGT GCA TTG       1310
Pro Lys His Ala Tyr Val Arg Thr Thr Gln Cys Ser Ser Ser Ala Leu
                400                 405                 410

TGG AGA CCA GCA CTT AGG GTGGGCGGGG CTCCTGAGGG AGTTCCAACT              1358
Trp Arg Pro Ala Leu Arg
            415

CAGAAGGGAG CTAGCCAGAG GACTGTGATG CCCTGCCCTT GGCACCCAAG AACTCAGGGC     1418

ACAAAGATGG GTGAAGGCTG GCATGATCCA AGCAAGATGA GGGGTCGATT CGGGTGGCCA     1478

TCTGGTTAGA TGGCAGGACG TGGGTGGGCC CACAAAGGCA AAGGGTCCAG AAGGAGACAG     1538

GCAGAGCTGC TCCCCTCTGC ACGGACCATG CGACACTGGG AGGCCAGTGA GCCACTCCGG     1598

CCCCGAATGT TGAGGTGGAC TCTCACCAAA TGAGAAGAAA ATGGAACCAG CTTGGAACC      1658

GTAGGACCCA AGCAGAGAAG CTCTCGGGCT AGGAAGATCT CTGCAGGGCC GCCAGGGAGA     1718

CCTGGACACA GGCCTGCTCT CTTTTTCTCC AGGGTCAGAA ACAGGACCGG GTGGAAGGGA     1778

TGGGGTGCCA GTTTGAATGC AGTCTGTCCA GGCTCGTCAT TGGAGGTGAA CAAGCAAACC    1838

CAGACGGCTC CACTAGGACT TCAAATTGGG GGTTGGATTT GAAGACTTTT AAGTTTCCTT    1898
```

```
CCAGCCCAGA AAGTCTCTCA TTCTAGCCTC CTGGCCCAGG TGAGTCCTAG AGCTACAGGG      1958

GTTCTGGAAA CATTCAGGAG CTTCCTGTCC TCCCAGCTCC TCACTCACCT TCAGTAACCC      2018

CCACTGGACT GACCTGGTCC ACAGGGCACC TGCCACCCTG GGCCTGGCAG CTCAGCTTCC      2078

CAACACGCAG GAGCACACCC AGCCCCCACA TCCTGTGCCT CCATCAGCTA AACACCACGT      2138

CACTTCATGC AGGTGAAACC CAGTCACTGT GAGCTCCCAG GTGCAGCCAG AGGCACCTCA      2198

AGAAGAAGAG GGGCATAAAC TTTCCTCTTC CTGCCTAGAG GCCCCACCTT GGTGCTTTC       2258

CAGAATCCCG TAACACCTGA TTAACTGAGG CATCCACTTC TTTCAGCAGA CTGATCAGGA      2318

CCTCCAAGCC ACTGAGCAAT GTATAACCCC AAAGGGAATT CAA                       2361

(2) INFORMATION FOR SEQ ID NO:8:

(i) SEQUENCE CHARACTERISTICS:
        (A) LENGTH: 1344 base pairs
        (B) TYPE: nucleic acid
        (C) STRANDEDNESS: single
        (D) TOPOLOGY: linear (ii) MOLECULE TYPE: DNA (xi) SEQUENCE DESCRIPTION: SEQ ID NO:8:

GGCGAGGCTG CTGGTGGCTG TGGAGAGCTT GGGGCTTCCT TGGTCGCACC CACCACCTGC      60

CTGCCCACTG GTCAGCCTTC AGGGAACCCT GAGCACCGCC TGGTCTCTTT CCTGTGGCCA     120

GCCCAGAACT GAAGCGCTGC GGC ATG GCG CGC GCC TGC CTC CAG GCC GTC         170
                         Met Ala Arg Ala Cys Leu Gln Ala Val
                          1               5

AAG TAC CTC ATG TTC GCC TTC AAC CTG CTC TTC TGG CTG GGA GGC TGT        218
Lys Tyr Leu Met Phe Ala Phe Asn Leu Leu Phe Trp Leu Gly Gly Cys
 10              15                  20                  25

GGC GTG CTG GGT GTC GGC ATC TGG CTG GCC GCA CAA CAG GGG AGC TTT        266
Gly Val Leu Gly Val Gly Ile Trp Leu Ala Ala Gln Gln Gly Ser Phe
                 30                  35                  40

GCC ACG CTG TCC TCT TCC TTC CCG TCC CTG TGG GCT GCC AAC CTG CTC        314
Ala Thr Leu Ser Ser Ser Phe Pro Ser Leu Trp Ala Ala Asn Leu Leu
             45                  50                  55

ATC ATC ACC GGC GCC TTT GTC ATG GCC ATC GGC TTC GTG GGC TGC CTG        362
Ile Ile Thr Gly Ala Phe Val Met Ala Ile Gly Phe Val Gly Cys Leu
         60                  65                  70

GGT GCC ATC AAG GAG AAC AAG TGC CTC CTG CTC ACT TTC TTC CTG CTG        410
Gly Ala Ile Lys Glu Asn Lys Cys Leu Leu Leu Thr Phe Phe Leu Leu
     75                  80                  85

CTG CTG CTG GTG TTC CTG CTG GAG GGC ACC ATC GCC ATC CTC TTC TTC        458
Leu Leu Leu Val Phe Leu Leu Glu Gly Thr Ile Ala Ile Leu Phe Phe
 90                  95                 100                 105

GCC TAC ACG GAC AAG ATT GAC AGG TAT GCC CAG CAA GAC CTG AAG AAA        506
Ala Tyr Thr Asp Lys Ile Asp Arg Tyr Ala Gln Gln Asp Leu Lys Lys
                110                 115                 120

GGC TTG CAC CTG TAC GGC ACG CAG GGC AAC GTG GGC CTC ACC AAC GCC        554
Gly Leu His Leu Tyr Gly Thr Gln Gly Asn Val Gly Leu Thr Asn Ala
            125                 130                 135

TGG AGC ATC ATC CAG ACC GAC TTC CGC TGC TGT GGC GTC TCC AAC TAC        602
Trp Ser Ile Ile Gln Thr Asp Phe Arg Cys Cys Gly Val Ser Asn Tyr
        140                 145                 150

ACT GAC TGG TTC GAG GTG TAC AAC GCC ACG CGG GTA CCT GAC TCC TGC        650
Thr Asp Trp Phe Glu Val Tyr Asn Ala Thr Arg Val Pro Asp Ser Cys
    155                 160                 165

TGC TTG GAG TTC AGT GAG AGC TGT GGG CTG CAC GCC CCG GCA CTG GTG        698
```

```
Cys Leu Glu Phe Ser Glu Ser Cys Gly Leu His Ala Pro Ala Leu Val
170                 175                 180                 185

GAG GGC CGT GCT ACG AGA GGT GAA GGT GTG GCT TCA GGA GAA CTG CTG        746
Glu Gly Arg Ala Thr Arg Gly Glu Gly Val Ala Ser Gly Glu Leu Leu
                    190                 195                 200

GCT GTG GGC ATC TTT GGG CTG TGC ACG GCG CTG GTG CAG ATC CTG GGC        794
Ala Val Gly Ile Phe Gly Leu Cys Thr Ala Leu Val Gln Ile Leu Gly
                205                 210                 215

CTG AAC TTC GCC ATG ACC ATG TAC TGG CAA GTG GTC AAG GCA GAC ACC        842
Leu Asn Phe Ala Met Thr Met Tyr Trp Gln Val Val Lys Ala Asp Thr
        220                 225                 230

TAC TGT GCG TAG G CCCCCCACCG CCCGCTTCTC TTTCAAAAGG ACGCCCACGG          895
Tyr Cys Ala
    235

GGAGATGGCC GCACCCACAG AGTGTCTTTC CCACCACCAG CCTCGGTGCT CTTTCCCATG      955

CTGGGAGGAG GGAGGGAGGG AAAGTTGCCT GGAGCCCCCG GAACCCTGTT TCTGGAAGGC     1015

CCTAGCTCAG GTGGCTTTCA GGGCCTCCGG ACCCCCCCTG GGAAGGGTGG CCACGTGCTG     1075

GCTTCGGAAC CCAGGGCAGG GGTGGGAGGG GCCTCCAGCA CTTTTTATAT TTACGTATTC     1135

TCCAAAACAG TGTTCACACG GGAGCCAACC TGTGGCCCCC AGCCTCCTGG AAAAAAGGTT     1195

GGCGCTGGAG GAACCGGGTC TTGGCATCCT GGAGGTGGCC CCACTGGTCC TGGTGCTCCA     1255

GGCGGGGCCG TGGACCCCTC ACCTACATTC CATAGTGGGC CCGTGGGGCT CCTGGTGCAT     1315

CTTAATAAAG TGTGAGCAGC AAAAAAAAA                                       1344

(2) INFORMATION FOR SEQ ID NO:9:

(i) SEQUENCE CHARACTERISTICS:
        (A) LENGTH: 1641 base pairs
        (B) TYPE: nucleic acid
        (C) STRANDEDNESS: single
        (D) TOPOLOGY: linear (ii) MOLECULE TYPE: DNA (xi) SEQUENCE DESCRIPTION: SEQ ID NO:9:

AGCCCAAGTT GAAGAAAGCC GGGCTGTGCC TGGAAGCCGA GAGAGGCGGT AATATTTAGA       60

AGCTGCACAG GAGAGGAACA TGAACTGACG AGTAAAC ATG TAT GGA AAT TAT TCT      115
                                        Met Tyr Gly Asn Tyr Ser
                                          1               5

CAC TTC ATG AAG TTT CCC GCA GGC TAT GGA GGC TCC CCT GGC CAC ACT        163
His Phe Met Lys Phe Pro Ala Gly Tyr Gly Gly Ser Pro Gly His Thr
            10                  15                  20

GGC TCT ACA TCC ATG AGC CCA TCA GCA GCC TTG TCC ACA GGG AAG CCA        211
Gly Ser Thr Ser Met Ser Pro Ser Ala Ala Leu Ser Thr Gly Lys Pro
        25                  30                  35

ATG GAC AGC CAC CCC AGC TAC ACA GAT ACC CCA GTG AGT GCC CCA CGG        259
Met Asp Ser His Pro Ser Tyr Thr Asp Thr Pro Val Ser Ala Pro Arg
    40                  45                  50

ACT CTG AGT GCA GTG GGG ACC CCC CTC AAT GCC CTG GGC TCT CCA TAT        307
Thr Leu Ser Ala Val Gly Thr Pro Leu Asn Ala Leu Gly Ser Pro Tyr
55                  60                  65                  70

CGA GTC ATC ACC TCT GCC ATG GGC CCA CCC TCA GGA GCA CTT GCA GCG        355
Arg Val Ile Thr Ser Ala Met Gly Pro Pro Ser Gly Ala Leu Ala Ala
                75                  80                  85

CCT CCA GGA ATC AAC TTG GTT GCC CCA CCC AGC TCT CAG CTA AAT GTG        403
Pro Pro Gly Ile Asn Leu Val Ala Pro Pro Ser Ser Gln Leu Asn Val
            90                  95                 100

GTC AAC AGT GTC AGC AGT TCA GAG GAC ATC AAG CCC TTA CCA GGG CTT        451
```

```
Val Asn Ser Val Ser Ser Glu Asp Ile Lys Pro Leu Pro Gly Leu
        105                 110                 115

CCC GGG ATT GGA AAC ATG AAC TAC CCA TCC ACC AGC CCC GGA TCT CTG        499
Pro Gly Ile Gly Asn Met Asn Tyr Pro Ser Thr Ser Pro Gly Ser Leu
    120                 125                 130

GTT AAA CAC ATC TGT GCT ATC TGT GGA GAC AGA TCC TCA GGA AAG CAC        547
Val Lys His Ile Cys Ala Ile Cys Gly Asp Arg Ser Ser Gly Lys His
135                 140                 145                 150

TAC GGG GTA TAC AGT TGT GAA GGC TGC AAA GGG TTC TTC AAG AGG ACG        595
Tyr Gly Val Tyr Ser Cys Glu Gly Cys Lys Gly Phe Phe Lys Arg Thr
                155                 160                 165

ATA AGG AAG GAC CTC ATC TAC ACG TGT CGG GAT AAT AAA GAC TGC CTC        643
Ile Arg Lys Asp Leu Ile Tyr Thr Cys Arg Asp Asn Lys Asp Cys Leu
            170                 175                 180

ATT GAC AAG CGT CAG CGC AAC CGC TGC CAG TAC TGT CGC TAT CAG AAG        691
Ile Asp Lys Arg Gln Arg Asn Arg Cys Gln Tyr Cys Arg Tyr Gln Lys
                185                 190                 195

TGC CTT GTC ATG GGC ATG AAG AGG GAA GCT TGT GCA AAG AAG GAA AGA        739
Cys Leu Val Met Gly Met Lys Arg Glu Ala Cys Ala Lys Lys Glu Arg
200                 205                 210

CAG AGG AGC CGA GAG CGA GCT GAG AGT GAG GCA GAA TGT GCT ACC AGT        787
Gln Arg Ser Arg Glu Arg Ala Glu Ser Glu Ala Glu Cys Ala Thr Ser
215                 220                 225                 230

GGT CAT GAA GAC ATG CCT GTG GAG AGG ATT CTA GAA GCT GAA CTT GCT        835
Gly His Glu Asp Met Pro Val Glu Arg Ile Leu Glu Ala Glu Leu Ala
                235                 240                 245

GTT GAC CCA AAG ACA GAA TCC TAT GGT GAC ATG AAT ATG GAG AAC TCG        883
Val Asp Pro Lys Thr Glu Ser Tyr Gly Asp Met Asn Met Glu Asn Ser
            250                 255                 260

ACA AAT GAC CCT GTT ACC AAC ATA TGT CAT GCT GCT GAC AAG CAG CTT        931
Thr Asn Asp Pro Val Thr Asn Ile Cys His Ala Ala Asp Lys Gln Leu
                265                 270                 275

CAC ACC CTC GGT GAA TGG GCC AAG CGT ATT CCC CAC TTC TCT GAC CTC        979
His Thr Leu Gly Glu Trp Ala Lys Arg Ile Pro His Phe Ser Asp Leu
        280                 285                 290

ACC TTG GAG GAC CAG GTC ATT GTG CTT CGG ACA GGG TGG AAT GAA TTG       1027
Thr Leu Glu Asp Gln Val Ile Val Leu Arg Thr Gly Trp Asn Glu Leu
295                 300                 305                 310

CTG ATT GCC TCT TTC TCC CAC CGC TCA GTT TCC GTG GAG GAT GGC ATC       1075
Leu Ile Ala Ser Phe Ser His Arg Ser Val Ser Val Glu Asp Gly Ile
                315                 320                 325

CCT CTG GCC ACG GGT TTA CAT GTC CAC CGG AGC AGT GCC CAC AG            1119
Pro Leu Ala Thr Gly Leu His Val His Arg Ser Ser Ala His
        330                 335                 340

TGCTGGGGTC GGCTCCATCT TTGACAGAGC TCTAACTGAG CTGGTTTCCA AACTGAAAGA     1179

CATGCAGGTG GACAAGTCGG AACTGGGATG CCTGCGAGCC ATTGTTCTCT TTCAACCCCA     1239

GATGCCCAAG GGCCTGCCCA CCCCCTTTGA GGTGGAGACT CTGCGAAAGA AGGTTTATGC     1299

CACCCTTGAG GCCCACCACC AAGCAGAATA TCCGGAACAG CCAGGCAAGG TTTGCCAAGC     1359

TGCTGTGCGC CTCCCAGCTC TGCGTTCCAT TGGCTTGAAA TGCCTGGAGC ACCTCTTCTT     1419

CTTCAAGCTC ATCGGGGACA CCCCCATTGA CACCTTCCTC ATGGAGATGT TGGAGACCCC     1479

GCTGCAGATC ACCTGAGCCC CACCAGCCAA AGCCTCCCCA CCCAGGATGA CCCCTGGGCA     1539

GGTGTGTGTG GACCCCCACC CTGCACTTTC CTCCACCTCC CACCCTGACC CCCTTCCTGT     1599

CCCCAAAATG TGATGCTTAT AATAAAGAAA ACCTTTCTAC AA                         1641
```

(2) INFORMATION FOR SEQ ID NO:10:

(i) SEQUENCE CHARACTERISTICS:
    (A) LENGTH: 1185 base pairs
    (B) TYPE: nucleic acid
    (C) STRANDEDNESS: single
    (D) TOPOLOGY: linear (ii) MOLECULE TYPE: DNA (xi) SEQUENCE DESCRIPTION: SEQ ID NO:10:

| | | | | | | | | | | | | | | | | |
|---|---|---|---|---|---|---|---|---|---|---|---|---|---|---|---|---|
| ATG | GCG | TTG | GAG | GTC | GGC | GAT | ATG | GAA | GAT | GGG | CAG | CTT | TCC | GAC | TCG | 48 |
| Met | Ala | Leu | Glu | Val | Gly | Asp | Met | Glu | Asp | Gly | Gln | Leu | Ser | Asp | Ser | |
| 1 | | | | 5 | | | | | 10 | | | | | 15 | | |
| GAT | TCC | GAC | ATG | ACG | GTC | GCA | CCC | AGC | GAC | AGG | CCG | CTG | CAA | TTG | CCA | 96 |
| Asp | Ser | Asp | Met | Thr | Val | Ala | Pro | Ser | Asp | Arg | Pro | Leu | Gln | Leu | Pro | |
| | | | 20 | | | | | 25 | | | | | 30 | | | |
| AAA | GTG | CTA | GGT | GGC | GAC | AGT | GCT | ATG | AGG | GCC | TTC | CAG | AAC | ACG | GCA | 144 |
| Lys | Val | Leu | Gly | Gly | Asp | Ser | Ala | Met | Arg | Ala | Phe | Gln | Asn | Thr | Ala | |
| | | 35 | | | | | 40 | | | | | 45 | | | | |
| ACT | GCA | TGT | GCA | CCA | GTA | TCA | CAT | TAT | CGA | GCT | GTT | GAA | AGT | GTG | GAT | 192 |
| Thr | Ala | Cys | Ala | Pro | Val | Ser | His | Tyr | Arg | Ala | Val | Glu | Ser | Val | Asp | |
| | 50 | | | | | 55 | | | | | 60 | | | | | |
| TCA | AGT | GAA | GAA | AGT | TTT | TCT | GAT | TCA | GAT | GAT | GAT | AGC | TGT | CTT | TGG | 240 |
| Ser | Ser | Glu | Glu | Ser | Phe | Ser | Asp | Ser | Asp | Asp | Asp | Ser | Cys | Leu | Trp | |
| 65 | | | | | 70 | | | | | 75 | | | | | 80 | |
| AAA | CGC | AAA | CGA | CAG | AAA | TGT | TTT | AAC | CCT | CCT | CCC | AAA | CCA | GAG | CCT | 288 |
| Lys | Arg | Lys | Arg | Gln | Lys | Cys | Phe | Asn | Pro | Pro | Pro | Lys | Pro | Glu | Pro | |
| | | | | 85 | | | | | 90 | | | | | 95 | | |
| TTT | CAG | TTT | GGC | CAG | AGC | AGT | CAG | AAA | CCA | CCT | GTT | GCT | GGA | GGA | AAG | 336 |
| Phe | Gln | Phe | Gly | Gln | Ser | Ser | Gln | Lys | Pro | Pro | Val | Ala | Gly | Gly | Lys | |
| | | | 100 | | | | | 105 | | | | | 110 | | | |
| AAG | ATT | AAC | AAC | ATA | TGG | GGT | GCT | GTG | CTG | CAG | GAA | CAG | AAT | CAA | GAT | 384 |
| Lys | Ile | Asn | Asn | Ile | Trp | Gly | Ala | Val | Leu | Gln | Glu | Gln | Asn | Gln | Asp | |
| | | 115 | | | | | 120 | | | | | 125 | | | | |
| GCA | GTG | GCC | ACT | GAA | CTT | GGT | ATC | TTG | GGA | ATG | GAG | GGC | ACT | ATT | GAC | 432 |
| Ala | Val | Ala | Thr | Glu | Leu | Gly | Ile | Leu | Gly | Met | Glu | Gly | Thr | Ile | Asp | |
| | 130 | | | | | 135 | | | | | 140 | | | | | |
| AGA | AGC | AGA | CAA | TCC | GAG | ACC | TAC | AAT | TAT | TTG | CTT | GCC | AAG | AAA | CTT | 480 |
| Arg | Ser | Arg | Gln | Ser | Glu | Thr | Tyr | Asn | Tyr | Leu | Leu | Ala | Lys | Lys | Leu | |
| 145 | | | | | 150 | | | | | 155 | | | | | 160 | |
| AGG | AAG | GAA | TCT | CAA | GAG | CAT | ACA | AAA | GAT | CTA | GAC | AAG | GAA | CTA | GAT | 528 |
| Arg | Lys | Glu | Ser | Gln | Glu | His | Thr | Lys | Asp | Leu | Asp | Lys | Glu | Leu | Asp | |
| | | | | 165 | | | | | 170 | | | | | 175 | | |
| GAA | TAT | ATG | CAT | GGT | GGC | AAA | AAA | ATG | GGA | TCA | AAG | GAA | GAG | GAA | AAT | 576 |
| Glu | Tyr | Met | His | Gly | Gly | Lys | Lys | Met | Gly | Ser | Lys | Glu | Glu | Glu | Asn | |
| | | | 180 | | | | | 185 | | | | | 190 | | | |
| GGG | CAA | GGT | CAT | CTC | AAA | AGG | AAA | CGA | CCT | GTC | AAA | GAC | AGG | CTA | GGG | 624 |
| Gly | Gln | Gly | His | Leu | Lys | Arg | Lys | Arg | Pro | Val | Lys | Asp | Arg | Leu | Gly | |
| | | 195 | | | | | 200 | | | | | 205 | | | | |
| AAC | AGA | CCA | GAA | ATG | AAC | TAT | AAA | GGT | CGA | TAC | GAG | ATC | ACA | GCG | GAA | 672 |
| Asn | Arg | Pro | Glu | Met | Asn | Tyr | Lys | Gly | Arg | Tyr | Glu | Ile | Thr | Ala | Glu | |
| | 210 | | | | | 215 | | | | | 220 | | | | | |
| GAT | TCT | CAA | GAG | AAA | GTG | GCT | GAT | GAA | ATT | TCA | TTC | AGG | TTA | CAG | GAA | 720 |
| Asp | Ser | Gln | Glu | Lys | Val | Ala | Asp | Glu | Ile | Ser | Phe | Arg | Leu | Gln | Glu | |
| 225 | | | | | 230 | | | | | 235 | | | | | 240 | |
| CCA | AAG | AAA | GAC | CTG | ATA | GCC | CGA | GTA | GTG | AGG | ATT | ATT | GGT | AAC | AAA | 768 |
| Pro | Lys | Lys | Asp | Leu | Ile | Ala | Arg | Val | Val | Arg | Ile | Ile | Gly | Asn | Lys | |
| | | | | 245 | | | | | 250 | | | | | 255 | | |
| AAG | GCA | ATT | GAA | CTT | CTG | ATG | GAA | ACC | GCT | GAA | GTT | GAA | CAA | AAT | GGT | 816 |
| Lys | Ala | Ile | Glu | Leu | Leu | Met | Glu | Thr | Ala | Glu | Val | Glu | Gln | Asn | Gly | |
| | | | 260 | | | | | 265 | | | | | 270 | | | |

```
GGT CTC TTT ATA ATG AAT GGT AGT CGA AGA AGA ACA CCA GGT GGA GTT          864
Gly Leu Phe Ile Met Asn Gly Ser Arg Arg Arg Thr Pro Gly Gly Val
        275                 280                 285

TTT CTG AAT CTC TTG AAA AAC ACT CCT AGT ATC AGC GAG GAA CAA ATT          912
Phe Leu Asn Leu Leu Lys Asn Thr Pro Ser Ile Ser Glu Glu Gln Ile
        290                 295                 300

AAG GAC ATT TTC TAC ATT GAA AAC CAA AAG GAA TAT GAA AAT AAA AAA          960
Lys Asp Ile Phe Tyr Ile Glu Asn Gln Lys Glu Tyr Glu Asn Lys Lys
305                 310                 315                 320

GCT GCT AGG AAG AGG AGA ACA CAA GTG TTG GGG AAA AAG ATG AAA CAA         1008
Ala Ala Arg Lys Arg Arg Thr Gln Val Leu Gly Lys Lys Met Lys Gln
            325                 330                 335

GCT ATT AAA AGT CTA AAT TTT CAA GAA GAT GAT GAT ACA TCA CGA GAA         1056
Ala Ile Lys Ser Leu Asn Phe Gln Glu Asp Asp Asp Thr Ser Arg Glu
        340                 345                 350

ACT TTT GCA AGT GAC ACG AAT GAG GCC TTG GCC TCT CTT GAT GAG TCA         1104
Thr Phe Ala Ser Asp Thr Asn Glu Ala Leu Ala Ser Leu Asp Glu Ser
        355                 360                 365

CAG GAA GGA CAT GCA GAA GCC AAG TTG GAG GCA GAG GAA GCC ATT GAA         1152
Gln Glu Gly His Ala Glu Ala Lys Leu Glu Ala Glu Glu Ala Ile Glu
        370                 375                 380

GTT GAT CAT TCT CAT GAT TTG GAC ATC TTT TAA                             1185
Val Asp His Ser His Asp Leu Asp Ile Phe
385                 390

(2) INFORMATION FOR SEQ ID NO:11:

(i) SEQUENCE CHARACTERISTICS:
        (A) LENGTH: 638 base pairs
        (B) TYPE: nucleic acid
        (C) STRANDEDNESS: single
        (D) TOPOLOGY: linear (ii) MOLECULE TYPE: DNA (xi) SEQUENCE DESCRIPTION: SEQ ID NO:11:

CACCTGCGCA GGCTTGGCTG CGCCTCTCGC GCCGCACGCT CTGGGGTTCC TCCCTTCTTC         60

CGAGCCTCTC CTCTGGCCGC CGCGCGGGAG AGAGGCCGAG ATG GCA GAT GAG ATT        115
                                              Met Ala Asp Glu Ile
                                                1               5

GCC AAG GCT CAG GTC GCT CGG CCT GGT GGC GAC ACG ATC TTT GGG AAG        163
Ala Lys Ala Gln Val Ala Arg Pro Gly Gly Asp Thr Ile Phe Gly Lys
            10                  15                  20

ATC ATC CGC AAG GAA ATA CCA GCC AAA ATC ATT TTT GAG GAT GAC CGG        211
Ile Ile Arg Lys Glu Ile Pro Ala Lys Ile Ile Phe Glu Asp Asp Arg
            25                  30                  35

TGC CTT GCT TTC CAT GAC ATT TCC CCT CAA GCA CCA ACA CAT TTT CTG        259
Cys Leu Ala Phe His Asp Ile Ser Pro Gln Ala Pro Thr His Phe Leu
        40                  45                  50

GTG ATA CCC AAG AAA CAT ATA TCC CAG ATT TCT GTG GCA GAA GAT GAT        307
Val Ile Pro Lys Lys His Ile Ser Gln Ile Ser Val Ala Glu Asp Asp
        55                  60                  65

GAT GAA AGT CTT CTT GGA CAC TTA ATG ATT GTT GGC AAG AAA TGT GCT        355
Asp Glu Ser Leu Leu Gly His Leu Met Ile Val Gly Lys Lys Cys Ala
70                  75                  80                  85

GCT GAT CTG GGC CTG AAT AAG GGT TAT CGA ATG GTG GTG AAT GAA GGT        403
Ala Asp Leu Gly Leu Asn Lys Gly Tyr Arg Met Val Val Asn Glu Gly
            90                  95                 100

TCA GAT GGT GGA CAG TCT GTC TAT CAC GTT CAT CTC CAT GTT CTT GGA        451
Ser Asp Gly Gly Gln Ser Val Tyr His Val His Leu His Val Leu Gly
            105                 110                 115
```

```
GGT CGG CAA ATG CAT TGG CCT CCT GGT TAA GCACGTTTTG GGGATAATTT          501
Gly Arg Gln Met His Trp Pro Pro Gly
        120                 125

TCTCTTCTTT AGGCAATGAT TAAGTTAGGC AATTTCCAGT ATGTTAAGTA ACACCTTATT     561

TTTGCCTGTG TATGGAGAGA TTCAAGAAAT AATTTTAAAA CCGCATACAT AATAAAAGAC     621

ATTGTTGCAT GGCTTAT                                                    638

(2) INFORMATION FOR SEQ ID NO:12:

(i) SEQUENCE CHARACTERISTICS:
        (A) LENGTH: 127 amino acids
        (B) TYPE: amino acid
        (D) TOPOLOGY: linear (ii) MOLECULE TYPE: protein (xi) SEQUENCE DESCRIPTION: SEQ ID NO:12:

Met Asp Val Phe Lys Lys Gly Phe Ser Ile Ala Lys Lys Gly Val
              5                  10                     15

Val Gly Ala Val Glu Lys Thr Lys Gln Gly Val Thr Glu Ala Ala
             20                  25                     30

Glu Lys Thr Lys Glu Gly Val Met Tyr Val Gly Ala Lys Thr Lys
             35                  40                     45

Glu Asn Val Val Gln Ser Val Thr Ser Val Ala Glu Lys Thr Lys
             50                  55                     60

Glu Gln Ala Asn Ala Val Ser Lys Ala Val Val Ser Ser Val Asn
             65                  70                     75

Thr Val Ala Thr Lys Thr Val Glu Glu Ala Glu Asn Ile Ala Val
             80                  85                     90

Thr Ser Gly Val Val Arg Lys Glu Asp Leu Arg Pro Ser Ala Pro
             95                 100                    105

Gln Gln Glu Gly Glu Ala Ser Lys Glu Lys Glu Glu Val Ala Glu
            110                 115                    120

Glu Ala Gln Ser Gly Gly Asp
            125

(2) INFORMATION FOR SEQ ID NO:13:

(i) SEQUENCE CHARACTERISTICS:
        (A) LENGTH: 443 amino acids
        (B) TYPE: amino acid
        (D) TOPOLOGY: linear (ii) MOLECULE TYPE: protein (xi) SEQUENCE DESCRIPTION: SEQ ID NO:13:

Met Asp Arg Leu Gly Ser Phe Ser Asn Asp Pro Ser Asp Lys Pro
              5                  10                     15

Pro Cys Arg Gly Cys Ser Ser Tyr Leu Met Glu Pro Tyr Ile Lys
             20                  25                     30

Cys Ala Glu Cys Gly Pro Pro Phe Phe Leu Cys Leu Gln Cys
             35                  40                     45

Phe Thr Arg Gly Phe Glu Tyr Lys Lys His Gln Ser Asp His Thr
             50                  55                     60

Tyr Glu Ile Met Thr Ser Asp Phe Pro Val Leu Asp Pro Ser Trp
             65                  70                     75

Thr Ala Gln Glu Glu Met Ala Leu Leu Glu Ala Val Met Asp Cys
             80                  85                     90
```

```
Gly Phe Gly Asn Trp Gln Asp Val Ala Asn Gln Met Cys Thr Lys
                 95                 100                 105

Thr Lys Glu Glu Cys Glu Lys His Tyr Met Lys His Phe Ile Asn
            110                 115                 120

Asn Pro Leu Phe Ala Ser Thr Leu Leu Asn Leu Lys Gln Ala Glu
            125                 130                 135

Glu Ala Lys Thr Ala Asp Thr Ala Ile Pro Phe His Ser Thr Asp
            140                 145                 150

Asp Pro Pro Arg Pro Thr Phe Asp Ser Leu Leu Ser Arg Asp Met
            155                 160                 165

Ala Gly Tyr Met Pro Ala Arg Ala Asp Phe Ile Glu Glu Phe Asp
            170                 175                 180

Asn Tyr Ala Glu Trp Asp Leu Arg Asp Ile Asp Phe Val Glu Asp
            185                 190                 195

Asp Ser Asp Ile Leu His Ala Leu Lys Met Ala Val Val Asp Ile
            200                 205                 210

Tyr His Ser Arg Leu Lys Glu Arg Gln Arg Arg Lys Lys Ile Ile
            215                 220                 225

Arg Asp His Gly Leu Ile Asn Leu Arg Lys Phe Gln Leu Met Glu
            230                 235                 240

Arg Arg Tyr Pro Lys Glu Val Gln Asp Leu Tyr Glu Thr Met Arg
            245                 250                 255

Arg Phe Ala Arg Ile Val Gly Pro Val Glu His Asp Lys Phe Ile
            260                 265                 270

Glu Ser His Ala Leu Glu Phe Glu Leu Arg Arg Glu Ile Lys Arg
            275                 280                 285

Leu Gln Glu Tyr Arg Thr Ala Gly Ile Thr Asn Phe Cys Ser Ala
            290                 295                 300

Arg Thr Tyr Asp His Leu Lys Lys Thr Arg Glu Glu Glu Arg Leu
            305                 310                 315

Lys Arg Thr Met Leu Ser Glu Val Leu Gln Tyr Ile Gln Asp Ser
            320                 325                 330

Ser Ala Cys Gln Gln Trp Leu Arg Arg Gln Ala Asp Ile Asp Ser
            335                 340                 345

Gly Leu Ser Pro Ser Ile Pro Met Ala Ser Asn Ser Gly Arg Arg
            350                 355                 360

Ser Ala Pro Pro Leu Asn Leu Thr Gly Leu Pro Gly Thr Glu Lys
            365                 370                 375

Leu Asn Glu Lys Glu Lys Glu Leu Cys Gln Met Val Arg Leu Val
            380                 385                 390

Pro Gly Ala Tyr Leu Glu Tyr Lys Ser Ala Leu Leu Asn Glu Cys
            395                 400                 405

Asn Lys Gln Gly Gly Leu Arg Leu Ala Gln Ala Arg Ala Leu Ile
            410                 415                 420

Lys Ile Asp Val Asn Lys Thr Arg Lys Ile Tyr Asp Phe Leu Ile
            425                 430                 435

Arg Glu Gly Tyr Ile Thr Lys Gly
            440

(2) INFORMATION FOR SEQ ID NO:14:

(i) SEQUENCE CHARACTERISTICS:
        (A) LENGTH: 186 amino acids
        (B) TYPE: amino acid
```

(D) TOPOLOGY: linear (ii) MOLECULE TYPE: protein (xi) SEQUENCE DESCRIPTION: SEQ ID NO:14:

Met Asp Ala Asp Ser Asp Val Ala Leu Asp Ile Leu Ile Thr Asn
                 5                  10                  15

Val Val Cys Val Phe Arg Thr Arg Cys His Leu Asn Leu Arg Lys
             20                  25                  30

Ile Ala Leu Glu Gly Ala Asn Val Ile Tyr Lys Arg Asp Val Gly
             35                  40                  45

Lys Val Leu Met Lys Leu Arg Lys Pro Arg Ile Thr Ala Thr Ile
             50                  55                  60

Trp Ser Ser Gly Lys Ile Ile Cys Thr Gly Ala Thr Ser Glu Glu
             65                  70                  75

Glu Ala Lys Phe Gly Ala Arg Arg Leu Ala Arg Ser Leu Gln Lys
             80                  85                  90

Leu Gly Phe Gln Val Ile Phe Thr Asp Phe Lys Val Val Asn Val
             95                 100                 105

Leu Ala Val Cys Asn Met Pro Phe Glu Ile Arg Leu Pro Glu Phe
            110                 115                 120

Thr Lys Asn Asn Arg Pro His Ala Ser Tyr Glu Pro Glu Leu His
            125                 130                 135

Pro Ala Val Cys Tyr Arg Ile Lys Ser Leu Arg Ala Thr Leu Gln
            140                 145                 150

Ile Phe Ser Thr Gly Ser Ile Thr Val Thr Gly Pro Asn Val Lys
            155                 160                 165

Ala Val Ala Thr Ala Val Glu Gln Ile Tyr Pro Phe Val Phe Glu
            170                 175                 180

Ser Arg Lys Glu Ile Leu
            185

(2) INFORMATION FOR SEQ ID NO:15:

(i) SEQUENCE CHARACTERISTICS:
        (A) LENGTH: 117 amino acids
        (B) TYPE: amino acid
        (D) TOPOLOGY: linear (ii) MOLECULE TYPE: protein (xi) SEQUENCE DESCRIPTION: SEQ ID NO:15:

Met Asn Ala Pro Pro Ala Phe Glu Ser Phe Leu Leu Phe Glu Gly
                 5                  10                  15

Glu Lys Lys Ile Thr Ile Asn Lys Asp Thr Lys Val Pro Asn Ala
             20                  25                  30

Cys Leu Phe Thr Ile Asn Lys Glu Asp His Thr Leu Gly Asn Ile
             35                  40                  45

Ile Lys Ser Gln Leu Leu Lys Asp Pro Gln Val Leu Phe Ala Gly
             50                  55                  60

Tyr Lys Val Pro His Pro Leu Glu His Lys Ile Ile Ile Arg Val
             65                  70                  75

Gln Thr Thr Pro Asp Tyr Ser Pro Gln Glu Ala Phe Thr Asn Ala
             80                  85                  90

Ile Thr Asp Leu Ile Ser Glu Leu Ser Leu Leu Glu Glu Arg Phe
             95                 100                 105

Arg Val Ala Ile Lys Asp Lys Gln Glu Gly Ile Glu

-continued

```
                110                 115

(2) INFORMATION FOR SEQ ID NO:16:

(i) SEQUENCE CHARACTERISTICS:
        (A) LENGTH: 427 amino acids
        (B) TYPE: amino acid
        (D) TOPOLOGY: linear (ii) MOLECULE TYPE: protein (xi) SEQUENCE DESCRIPTION: SEQ ID NO:16:

Met Gly Thr Pro Lys Pro Arg Xaa Leu Pro Trp Leu Val Ser Gln
                  5                  10                  15

Leu Asp Leu Gly Gln Leu Glu Gly Val Ala Trp Val Asn Lys Ser
                 20                  25                  30

Arg Thr Arg Phe Arg Ile Pro Trp Lys His Gly Leu Arg Gln Asp
                 35                  40                  45

Ala Gln Gln Glu Asp Phe Gly Ile Phe Gln Ala Trp Ala Glu Ala
                 50                  55                  60

Thr Gly Ala Tyr Val Pro Gly Arg Asp Lys Pro Asp Leu Pro Thr
                 65                  70                  75

Trp Lys Arg Asn Phe Arg Ser Ala Leu Asn Arg Lys Glu Gly Leu
                 80                  85                  90

Arg Leu Ala Glu Asp Arg Ser Lys Asp Pro His Asp Pro His Lys
                 95                 100                 105

Ile Tyr Glu Phe Val Asn Ser Gly Val Gly Asp Phe Ser Gln Pro
                110                 115                 120

Asp Thr Ser Pro Asp Thr Asn Gly Gly Gly Ser Thr Ser Asp Thr
                125                 130                 135

Gln Glu Asp Ile Leu Asp Glu Leu Leu Gly Asn Met Val Leu Ala
                140                 145                 150

Pro Leu Pro Asp Pro Gly Pro Pro Ser Leu Ala Val Ala Pro Glu
                155                 160                 165

Pro Cys Pro Gln Pro Leu Arg Ser Pro Ser Leu Asp Asn Pro Thr
                170                 175                 180

Pro Phe Pro Asn Leu Gly Pro Ser Glu Asn Pro Leu Lys Arg Leu
                185                 190                 195

Leu Val Pro Gly Glu Glu Trp Glu Phe Glu Val Thr Ala Phe Tyr
                200                 205                 210

Arg Gly Arg Gln Val Phe Gln Gln Thr Ile Ser Cys Pro Glu Gly
                215                 220                 225

Leu Arg Leu Val Gly Ser Glu Val Gly Asp Arg Thr Leu Pro Gly
                230                 235                 240

Trp Pro Val Thr Leu Pro Asp Pro Gly Met Ser Leu Thr Asp Arg
                245                 250                 255

Gly Val Met Ser Tyr Val Arg His Val Leu Ser Cys Leu Gly Gly
                260                 265                 270

Gly Leu Ala Leu Trp Arg Ala Gly Gln Trp Leu Trp Ala Gln Arg
                275                 280                 285

Leu Gly His Cys His Thr Tyr Trp Ala Val Ser Glu Glu Leu Leu
                290                 295                 300

Pro Asn Ser Gly His Gly Pro Asp Gly Glu Val Pro Lys Asp Lys
                305                 310                 315

Glu Gly Gly Val Phe Asp Leu Gly Pro Phe Ile Val Asp Leu Ile
                320                 325                 330
```

```
Thr Phe Thr Glu Gly Ser Gly Arg Ser Pro Arg Tyr Ala Leu Trp
             335                 340                 345

Phe Cys Val Gly Glu Ser Trp Pro Gln Asp Gln Pro Trp Thr Lys
             350                 355                 360

Arg Leu Val Met Val Lys Val Pro Thr Cys Leu Arg Ala Leu
             365                 370                 375

Val Glu Met Ala Arg Val Gly Ala Ser Ser Leu Glu Asn Thr
             380                 385                 390

Val Asp Leu His Ile Ser Asn Ser His Pro Leu Ser Leu Thr Ser
             395                 400                 405

Asp Gln Tyr Lys Ala Tyr Leu Gln Asp Leu Val Glu Gly Met Asp
             410                 415                 420

Phe Gln Gly Pro Gly Glu Ser
             425

(2) INFORMATION FOR SEQ ID NO:17:

(i) SEQUENCE CHARACTERISTICS:
        (A) LENGTH: 252 amino acids
        (B) TYPE: amino acid
        (D) TOPOLOGY: linear (ii) MOLECULE TYPE: protein (xi) SEQUENCE DESCRIPTION: SEQ ID NO:17:

Met Gly Gln Cys Gly Ile Thr Ser Ser Lys Thr Val Leu Val Phe
             5                   10                  15

Leu Asn Leu Ile Phe Trp Gly Ala Ala Gly Ile Leu Cys Tyr Val
             20                  25                  30

Gly Ala Tyr Val Phe Ile Thr Tyr Asp Asp Tyr Asp His Phe Phe
             35                  40                  45

Glu Asp Val Tyr Thr Leu Ile Pro Ala Val Val Ile Ala Val
             50                  55                  60

Gly Ala Leu Leu Phe Ile Ile Gly Leu Ile Gly Cys Cys Ala Thr
             65                  70                  75

Ile Arg Glu Ser Arg Cys Gly Leu Ala Thr Phe Val Ile Ile Leu
             80                  85                  90

Leu Leu Val Phe Val Thr Glu Val Val Val Val Val Leu Gly Tyr
             95                  100                 105

Val Tyr Arg Ala Lys Val Glu Asn Glu Val Asp Arg Ser Ile Gln
             110                 115                 120

Lys Val Tyr Lys Thr Tyr Asn Gly Thr Asn Pro Asp Ala Ala Ser
             125                 130                 135

Arg Ala Ile Asp Tyr Val Gln Arg Gln Leu His Cys Cys Gly Ile
             140                 145                 150

His Asn Tyr Ser Asp Trp Glu Asn Thr Asp Trp Phe Lys Glu Thr
             155                 160                 165

Lys Asn Gln Ser Val Pro Leu Ser Cys Cys Arg Glu Thr Ala Ser
             170                 175                 180

Asn Cys Asn Gly Ser Trp Pro Pro Phe Arg Leu Tyr Ala Glu Gly
             185                 190                 195

Cys Glu Ala Leu Val Val Lys Lys Leu Gln Glu Ile Met Met His
             200                 205                 210

Val Ile Trp Ala Ala Leu Ala Phe Ala Ala Ile Gln Leu Leu Gly
             215                 220                 225
```

```
Met Leu Cys Ala Cys Ile Val Leu Cys Arg Arg Ser Arg Asp Pro
            230                 235                 240

Ala Tyr Glu Leu Leu Ile Thr Gly Gly Thr Tyr Ala
            245                 250
```

(2) INFORMATION FOR SEQ ID NO:18:

(i) SEQUENCE CHARACTERISTICS:
        (A) LENGTH: 417 amino acids
        (B) TYPE: amino acid
        (D) TOPOLOGY: linear (ii) MOLECULE TYPE: protein (xi) SEQUENCE DESCRIPTION: SEQ ID NO:18:

```
Met Ala Ser Ser Ser Gly Ser Ser Pro Arg Pro Ala Pro Asp Glu
              5                  10                  15

Asn Glu Phe Pro Phe Gly Cys Pro Pro Thr Val Cys Gln Asp Pro
             20                  25                  30

Lys Glu Pro Arg Ala Leu Cys Cys Ala Gly Cys Leu Ser Glu Asn
             35                  40                  45

Pro Arg Asn Gly Glu Asp Gln Ile Cys Pro Lys Cys Arg Gly Glu
             50                  55                  60

Asp Leu Gln Ser Ile Ser Pro Gly Ser Arg Leu Arg Thr Gln Glu
             65                  70                  75

Lys Val Gln Ala Glu Val Ala Glu Ala Gly Ile Gly Cys Pro Phe
             80                  85                  90

Ala Val Val Gly Cys Ser Phe Lys Gly Ser Pro Gln Phe Val Glu
             95                 100                 105

Glu His Glu Val Thr Ser Gln Thr Ser His Leu Asn Leu Leu Leu
            110                 115                 120

Gly Phe Met Lys Gln Trp Lys Ala Arg Leu Gly Cys Gly Leu Asp
            125                 130                 135

Ser Gly Pro Met Ala Leu Glu Gln Asn Leu Ser Asp Leu Gln Leu
            140                 145                 150

Gln Ala Ala Val Glu Val Ala Gly Asp Leu Glu Val Asp Cys Tyr
            155                 160                 165

Arg Ala Pro Cys Ser Glu Ser Gln Glu Glu Leu Ala Leu Gln His
            170                 175                 180

Phe Met Lys Glu Lys Leu Leu Ala Glu Leu Glu Gly Lys Leu Arg
            185                 190                 195

Val Phe Glu Asn Asn Val Ala Val Leu Asn Lys Glu Val Glu Ala
            200                 205                 210

Ser His Leu Ala Leu Ala Thr Ser Ile His Gln Ser Gln Leu Asp
            215                 220                 225

Arg Glu Arg Ile Leu Ser Leu Glu Gln Arg Val Val Gln Val Gln
            230                 235                 240

Gln Thr Leu Ala Gln Lys Asp Gln Ala Leu Gly Lys Leu Glu Gln
            245                 250                 255

Ser Leu Arg Leu Met Glu Glu Ala Ser Phe Asp Gly Thr Phe Leu
            260                 265                 270

Trp Lys Ile Thr Ser Val Thr Arg Arg Cys His Glu Ser Ala Cys
            275                 280                 285

Gly Arg Thr Val Ser Leu Phe Ser Pro Ala Phe Tyr Thr Ala Lys
            290                 295                 300

Tyr Gly Tyr Lys Leu Cys Leu Arg Leu Tyr Leu Ile Gly Asp Gly
```

```
                   305                 310                 315
Thr Gly Lys Arg Thr His Leu Ser Leu Phe Ile Val Ile Met Arg
                320                 325                 330

Gly Glu Tyr Asp Ala Leu Leu Pro Trp Pro Phe Arg Asn Lys Val
                335                 340                 345

Thr Phe Met Leu Leu Asp Gln Asn Asn Arg Glu His Ala Ile Asp
                350                 355                 360

Ala Phe Arg Pro Asp Leu Ser Ser Ala Ser Phe Gln Arg Pro Gln
                365                 370                 375

Ser Glu Thr Asn Val Ala Ser Gly Cys Pro Leu Phe Phe Pro Leu
                380                 385                 390

Ser Lys Leu Gln Ser Pro Lys His Ala Tyr Val Arg Thr Thr Gln
                395                 400                 405

Cys Ser Ser Ser Ala Leu Trp Arg Pro Ala Leu Arg
                410                 415

(2) INFORMATION FOR SEQ ID NO:19:

(i) SEQUENCE CHARACTERISTICS:
        (A) LENGTH: 236 amino acids
        (B) TYPE: amino acid
        (D) TOPOLOGY: linear (ii) MOLECULE TYPE: protein (xi) SEQUENCE DESCRIPTION: SEQ ID NO:19:

Met Ala Arg Ala Cys Leu Gln Ala Val Lys Tyr Leu Met Phe Ala
                  5                  10                  15

Phe Asn Leu Leu Phe Trp Leu Gly Gly Cys Gly Val Leu Gly Val
                 20                  25                  30

Gly Ile Trp Leu Ala Ala Gln Gln Gly Ser Phe Ala Thr Leu Ser
                 35                  40                  45

Ser Ser Phe Pro Ser Leu Trp Ala Ala Asn Leu Leu Ile Ile Thr
                 50                  55                  60

Gly Ala Phe Val Met Ala Ile Gly Phe Val Gly Cys Leu Gly Ala
                 65                  70                  75

Ile Lys Glu Asn Lys Cys Leu Leu Leu Thr Phe Phe Leu Leu Leu
                 80                  85                  90

Leu Leu Val Phe Leu Leu Glu Gly Thr Ile Ala Ile Leu Phe Phe
                 95                 100                 105

Ala Tyr Thr Asp Lys Ile Asp Arg Tyr Ala Gln Gln Asp Leu Lys
                110                 115                 120

Lys Gly Leu His Leu Tyr Gly Thr Gln Gly Asn Val Gly Leu Thr
                125                 130                 135

Asn Ala Trp Ser Ile Ile Gln Thr Asp Phe Arg Cys Cys Gly Val
                140                 145                 150

Ser Asn Tyr Thr Asp Trp Phe Glu Val Tyr Asn Ala Thr Arg Val
                155                 160                 165

Pro Asp Ser Cys Cys Leu Glu Phe Ser Glu Ser Cys Gly Leu His
                170                 175                 180

Ala Pro Ala Leu Val Glu Gly Arg Ala Thr Arg Gly Glu Gly Val
                185                 190                 195

Ala Ser Gly Glu Leu Leu Ala Val Gly Ile Phe Gly Leu Cys Thr
                200                 205                 210

Ala Leu Val Gln Ile Leu Gly Leu Asn Phe Ala Met Thr Met Tyr
                215                 220                 225
```

```
Trp Gln Val Val Lys Ala Asp Thr Tyr Cys Ala
                230                 235
```

(2) INFORMATION FOR SEQ ID NO:20:

(i) SEQUENCE CHARACTERISTICS:
        (A) LENGTH: 340 amino acids
        (B) TYPE: amino acid
        (D) TOPOLOGY: linear (ii) MOLECULE TYPE: protein (xi) SEQUENCE DESCRIPTION: SEQ ID NO:20:

```
Met Tyr Gly Asn Tyr Ser His Phe Met Lys Phe Pro Ala Gly Tyr
                  5                  10                  15

Gly Gly Ser Pro Gly His Thr Gly Ser Thr Ser Met Ser Pro Ser
                 20                  25                  30

Ala Ala Leu Ser Thr Gly Lys Pro Met Asp Ser His Pro Ser Tyr
                 35                  40                  45

Thr Asp Thr Pro Val Ser Ala Pro Arg Thr Leu Ser Ala Val Gly
                 50                  55                  60

Thr Pro Leu Asn Ala Leu Gly Ser Pro Tyr Arg Val Ile Thr Ser
                 65                  70                  75

Ala Met Gly Pro Pro Ser Gly Ala Leu Ala Ala Pro Pro Gly Ile
                 80                  85                  90

Asn Leu Val Ala Pro Pro Ser Ser Gln Leu Asn Val Val Asn Ser
                 95                 100                 105

Val Ser Ser Ser Glu Asp Ile Lys Pro Leu Pro Gly Leu Pro Gly
                110                 115                 120

Ile Gly Asn Met Asn Tyr Pro Ser Thr Ser Pro Gly Ser Leu Val
                125                 130                 135

Lys His Ile Cys Ala Ile Cys Gly Asp Arg Ser Ser Gly Lys His
                140                 145                 150

Tyr Gly Val Tyr Ser Cys Glu Gly Cys Lys Gly Phe Phe Lys Arg
                155                 160                 165

Thr Ile Arg Lys Asp Leu Ile Tyr Thr Cys Arg Asp Asn Lys Asp
                170                 175                 180

Cys Leu Ile Asp Lys Arg Gln Arg Asn Arg Cys Gln Tyr Cys Arg
                185                 190                 195

Tyr Gln Lys Cys Leu Val Met Gly Met Lys Arg Glu Ala Cys Ala
                200                 205                 210

Lys Lys Glu Arg Gln Arg Ser Arg Glu Arg Ala Glu Ser Glu Ala
                215                 220                 225

Glu Cys Ala Thr Ser Gly His Glu Asp Met Pro Val Glu Arg Ile
                230                 235                 240

Leu Glu Ala Glu Leu Ala Val Asp Pro Lys Thr Glu Ser Tyr Gly
                245                 250                 255

Asp Met Asn Met Glu Asn Ser Thr Asn Asp Pro Val Thr Asn Ile
                260                 265                 270

Cys His Ala Ala Asp Lys Gln Leu His Thr Leu Gly Glu Trp Ala
                275                 280                 285

Lys Arg Ile Pro His Phe Ser Asp Leu Thr Leu Glu Asp Gln Val
                290                 295                 300

Ile Val Leu Arg Thr Gly Trp Asn Glu Leu Leu Ile Ala Ser Phe
                305                 310                 315
```

-continued

Ser His Arg Ser Val Ser Val Glu Asp Gly Ile Pro Leu Ala Thr
                320                 325                 330

Gly Leu His Val His Arg Ser Ser Ala His
                335                 340

(2) INFORMATION FOR SEQ ID NO:21:

(i) SEQUENCE CHARACTERISTICS:
        (A) LENGTH: 394 amino acids
        (B) TYPE: amino acid
        (D) TOPOLOGY: linear (ii) MOLECULE TYPE: protein (xi) SEQUENCE DESCRIPTION: SEQ ID NO:21:

Met Ala Leu Glu Val Gly Asp Met Glu Asp Gly Gln Leu Ser Asp
                  5                  10                  15

Ser Asp Ser Asp Met Thr Val Ala Pro Ser Asp Arg Pro Leu Gln
                 20                  25                  30

Leu Pro Lys Val Leu Gly Gly Asp Ser Ala Met Arg Ala Phe Gln
                 35                  40                  45

Asn Thr Ala Thr Ala Cys Ala Pro Val Ser His Tyr Arg Ala Val
                 50                  55                  60

Glu Ser Val Asp Ser Ser Glu Glu Ser Phe Ser Asp Ser Asp Asp
                 65                  70                  75

Asp Ser Cys Leu Trp Lys Arg Lys Arg Gln Lys Cys Phe Asn Pro
                 80                  85                  90

Pro Pro Lys Pro Glu Pro Phe Gln Phe Gly Gln Ser Ser Gln Lys
                 95                 100                 105

Pro Pro Val Ala Gly Gly Lys Lys Ile Asn Asn Ile Trp Gly Ala
                110                 115                 120

Val Leu Gln Glu Gln Asn Gln Asp Ala Val Ala Thr Glu Leu Gly
                125                 130                 135

Ile Leu Gly Met Glu Gly Thr Ile Asp Arg Ser Arg Gln Ser Glu
                140                 145                 150

Thr Tyr Asn Tyr Leu Leu Ala Lys Lys Leu Arg Lys Glu Ser Gln
                155                 160                 165

Glu His Thr Lys Asp Leu Asp Lys Glu Leu Asp Glu Tyr Met His
                170                 175                 180

Gly Gly Lys Lys Met Gly Ser Lys Glu Glu Asn Gly Gln Gly
                185                 190                 195

His Leu Lys Arg Lys Arg Pro Val Lys Asp Arg Leu Gly Asn Arg
                200                 205                 210

Pro Glu Met Asn Tyr Lys Gly Arg Tyr Glu Ile Thr Ala Glu Asp
                215                 220                 225

Ser Gln Glu Lys Val Ala Asp Glu Ile Ser Phe Arg Leu Gln Glu
                230                 235                 240

Pro Lys Lys Asp Leu Ile Ala Arg Val Arg Ile Ile Gly Asn
                245                 250                 255

Lys Lys Ala Ile Glu Leu Leu Met Glu Thr Ala Glu Val Glu Gln
                260                 265                 270

Asn Gly Gly Leu Phe Ile Met Asn Gly Ser Arg Arg Arg Thr Pro
                275                 280                 285

Gly Gly Val Phe Leu Asn Leu Leu Lys Asn Thr Pro Ser Ile Ser
                290                 295                 300

Glu Glu Gln Ile Lys Asp Ile Phe Tyr Ile Glu Asn Gln Lys Glu

```
                        305                 310                 315
Tyr Glu Asn Lys Lys Ala Ala Arg Lys Arg Arg Thr Gln Val Leu
                320                 325                 330
Gly Lys Lys Met Lys Gln Ala Ile Lys Ser Leu Asn Phe Gln Glu
                335                 340                 345
Asp Asp Asp Thr Ser Arg Glu Thr Phe Ala Ser Asp Thr Asn Glu
                350                 355                 360
Ala Leu Ala Ser Leu Asp Glu Ser Gln Glu Gly His Ala Glu Ala
                365                 370                 375
Lys Leu Glu Ala Glu Ala Ile Glu Val Asp His Ser His Asp
                380                 385                 390
Leu Asp Ile Phe (2) INFORMATION FOR SEQ ID NO:22:

(i) SEQUENCE CHARACTERISTICS:
        (A) LENGTH:  126 AMINO ACIDS
        (B) TYPE:  AMINO ACID
        (C) STRANDEDNESS:
        (D) TOPOLOGY:  LINEAR (ii) MOLECULE TYPE:  PROTEIN (xi) SEQUENCE DESCRIPTION:  SEQ ID NO:22:

Met Ala Asp Glu Ile Ala Lys Ala Gln Val Ala Arg Pro Gly Gly
                 5                  10                  15
Asp Thr Ile Phe Gly Lys Ile Ile Arg Lys Glu Ile Pro Ala Lys
                20                  25                  30
Ile Ile Phe Glu Asp Asp Arg Cys Leu Ala Phe His Asp Ile Ser
                35                  40                  45
Pro Gln Ala Pro Thr His Phe Leu Val Ile Pro Lys Lys His Ile
                50                  55                  60
Ser Gln Ile Ser Val Ala Glu Asp Asp Glu Ser Leu Leu Gly
                65                  70                  75
His Leu Met Ile Val Gly Lys Lys Cys Ala Ala Asp Leu Gly Leu
                80                  85                  90
Asn Lys Gly Tyr Arg Met Val Val Asn Glu Gly Ser Asp Gly Gly
                95                  100                 105
Gln Ser Val Tyr His Val His Leu His Val Leu Gly Gly Arg Gln
                110                 115                 120
Met His Trp Pro Pro Gly
                125
```